US011898165B2

(12) United States Patent
Van Dijk et al.

(10) Patent No.: US 11,898,165 B2
(45) Date of Patent: Feb. 13, 2024

(54) ENGINEERED HOST CELLS AND METHODS OF USE THEREOF

(71) Applicant: MiNk Therapeutics, Inc., New York, NY (US)

(72) Inventors: Marc Van Dijk, Cambridge (GB); Volker Seibert, Lörrach (DE); Robert Benjamin Stein, Brooklyn, NY (US)

(73) Assignee: MiNK Therapeutics, Inc., New York, NY (US)

( * ) Notice: Subject to any disclaimer, the term of this patent is extended or adjusted under 35 U.S.C. 154(b) by 1657 days.

(21) Appl. No.: 15/759,007

(22) PCT Filed: Sep. 9, 2016

(86) PCT No.: PCT/US2016/050850
§ 371 (c)(1),
(2) Date: Mar. 9, 2018

(87) PCT Pub. No.: WO2017/044672
PCT Pub. Date: Mar. 16, 2017

(65) Prior Publication Data
US 2020/0263133 A1     Aug. 20, 2020

Related U.S. Application Data

(60) Provisional application No. 62/217,677, filed on Sep. 11, 2015.

(51) Int. Cl.
| | |
|---|---|
| *C07K 14/725* | (2006.01) |
| *C07K 14/705* | (2006.01) |
| *C12N 15/86* | (2006.01) |
| *G01N 33/50* | (2006.01) |
| *C12N 5/0783* | (2010.01) |
| *C12N 15/10* | (2006.01) |

(52) U.S. Cl.
CPC ........ *C12N 5/0646* (2013.01); *C07K 14/7051* (2013.01); *C07K 14/70517* (2013.01); *C07K 14/70521* (2013.01); *C07K 14/70578* (2013.01); *C12N 15/1037* (2013.01); *C12N 15/86* (2013.01); *G01N 33/5005* (2013.01); *C07K 2319/00* (2013.01); *C12N 2740/10043* (2013.01)

(58) Field of Classification Search
CPC .............. C12N 5/0646; C07K 14/7051; C07K 14/70517; C07K 2319/00
See application file for complete search history.

(56) References Cited

U.S. PATENT DOCUMENTS

| | | | | |
|---|---|---|---|---|
| 2003/0093818 | A1* | 5/2003 | Belmont | ............ A01K 67/0276 800/14 |
| 2014/0245466 | A1* | 8/2014 | Macdonald | ...... C07K 14/70517 800/13 |

FOREIGN PATENT DOCUMENTS

| | | |
|---|---|---|
| EP | 1 188 825 A1 | 3/2002 |
| WO | WO 2012/031744 A1 | 3/2012 |
| WO | WO-2013074916 A1 * | 5/2013 ............. A61K 35/17 |

OTHER PUBLICATIONS

Wen et al. A Subset of CD8ab+ Invariant NKT Cells in a Humanized Mouse Model. J Immunol 2015; 195:1459-1469 (Year: 2015).*
Hooijberg et al. NFAT-controlled expression of GFP permits visualization and isolation of antigen-stimulated primary human T cells. Blood, Jul. 15, 2000 x vol. 96, No. 2 (Year: 2000).*
International Search Report and Written Opinion for Application No. PCT/US2016/050850, dated Nov. 18, 2016.
International Preliminary Report on Patentability for Application No. PCT/US2016/050850, dated Mar. 22, 2018.
Figueroa et al., Chimeric antigen receptor engineering: a right step in the evolution of adoptive cellular immunotherapy. Int Rev Immunol. Mar. 2015;34(2):154-87. doi: 10.3109/08830185.2015. 1018419.

* cited by examiner

*Primary Examiner* — Amy E Juedes
*Assistant Examiner* — Brian Hartnett
(74) *Attorney, Agent, or Firm* — Wolf, Greenfield & Sacks, P.C.

(57) ABSTRACT

Provided herein are engineered host cells suitable for expression of functional T cell receptors (TCR) and methods of using these cells to identify TCRs that specifically bind to a desired peptide-major histocompatibility complex (MHC) complex.

12 Claims, 13 Drawing Sheets

Specification includes a Sequence Listing.

AK-D10 IL-2-(NFAT)$_3$-EGFP+ chiDMF4+ incubated with anti-CD3 antibody

AK-D10 IL-2-(NFAT)$_3$-EGFP+ chiDMF4+ incubated without anti-CD3 antibody

AK-D10 IL-2-(NFAT)$_3$-EGFP+ incubated with anti-CD3 antibody

ENGINEERED HOST CELLS AND METHODS OF USE THEREOF

RELATED APPLICATIONS

This application is a 35 U.S.C. § 371 filing of International Patent Application No. PCT/US2016/050850, filed Sep. 9, 2016, which claims the benefit of U.S. Provisional Patent Application Ser. No. 62/217,677, filed Sep. 11, 2015, the entire contents of which are hereby incorporated herein in their entirety.

FIELD OF THE INVENTION

The present disclosure provides engineered host cells suitable for expression of functional T cell receptors (TCR) and methods of using these cells to identify TCRs that specifically bind to a desired peptide-major histocompatibility complex (MHC) complex.

BACKGROUND

In mammals, the acquired immune system comprises two major components: the humoral immune response, involving antibodies, and the cellular immune response, involving T cells. T cells are the major mediators of adaptive cellular immunity and exert their action through the TCR-mediated recognition of a peptide epitope bound to a major histocompatibility complex (MHC) molecule. The immune system contains a large number of T cells that encompass a broad range of peptide-MHC specificities. However, negative and positive selection processes in the thymus result in a restriction on T cell diversity, limiting the spectrum of in vivo T cell reactivity. For example, negative selection leads to the removal of the high affinity T cell repertoire specific for self-antigens, and this includes T cells with desirable specificities, such as for self-antigens expressed on tumor tissues.

Cancer immunotherapy, the enhancement of a patient's immune response to cancerous cells, holds great promise. Active immunotherapy is carried out by stimulation of the endogenous immune system of tumor-bearing patients. Passive, or adoptive, immunotherapy involves the transfer of immune-competent cells into the patient. One approach to adoptive therapy is the use of gene therapy techniques to introduce TCRs specific for known cancer-specific peptide-MHC complexes into the T cells of cancer patients. However, this approach is reliant upon obtaining TCRs that bind specifically to cancer-specific peptide-MHC complexes with suitable affinity.

Accordingly, there is a need in the art for novel TCRs that specifically bind to a desired peptide-MHC complex (e.g., a peptide-MHC complex comprising a cancer-specific peptide antigen), and for technologies to discover such TCRs.

BRIEF SUMMARY OF THE INVENTION

Provided herein are engineered host cells suitable for expression of functional TCRs and methods of using these cells to identify TCRs that specifically bind to a desired peptide-MHC complex.

In one aspect, the disclosure provides a cell (e.g., an isolated cell) derived from a lymphocyte comprising a first polynucleotide encoding a recombinant co-receptor, or a first chain thereof, wherein the cell expresses CD3 but does not express an endogenous TCR on the cell surface. In certain embodiments, the CD3 is endogenous CD3. In certain embodiments, the CD3 is recombinant CD3. In certain embodiments, the cell expresses the recombinant co-receptor, or a first chain thereof, on the cell surface, and/or the cell expresses the recombinant co-receptor, or a first chain thereof, on the cell surface in a regulatable manner, and/or the cell does not express an endogenous co-receptor on the cell surface, and/or the endogenous co-receptor is CD8 or CD4.

In another aspect, the disclosure also provides a cell (e.g., an isolated cell) derived from a lymphocyte comprising a first polynucleotide encoding a recombinant co-receptor, or a first chain thereof, wherein the lymphocyte is an invariant NKT (iNKT) cell or a diverse NKT (dNKT) cell. In certain embodiments, the cell expresses the recombinant co-receptor, or a first chain thereof, on the cell surface. In certain embodiments, the cell does not express an endogenous co-receptor on the cell surface, and/or the endogenous co-receptor is CD8 or CD4.

In another aspect, the disclosure provides a cell (e.g., an isolated cell) derived from a lymphocyte comprising a first polynucleotide encoding a recombinant co-receptor, or a first chain thereof, wherein the cell is capable of expressing the recombinant co-receptor, or a first chain thereof, on the cell surface in a regulatable manner. In certain embodiments, the cell expresses the recombinant co-receptor, or a first chain thereof, on the cell surface in a regulatable manner. In certain embodiments, the cell does not express an endogenous co-receptor on the cell surface. In certain embodiments, the endogenous co-receptor is CD8 or CD4.

Each of the following embodiments apply to the cells of the invention described herein.

In certain embodiments, the recombinant co-receptor, or a first chain thereof, comprises an extracellular region, a transmembrane region, and a cytoplasmic region, wherein the extracellular region is linked to the transmembrane region, and the transmembrane region is linked to the cytoplasmic region.

In certain embodiments, the amino acid sequence of the cytoplasmic region of the recombinant co-receptor, or a first chain thereof, can be at least 90% identical, optionally 91, 92, 93, 94, 95, 96, 97, 98, 99, or 100% identical, to the amino acid sequence of a corresponding cytoplasmic region of a naturally occurring co-receptor, or a first chain thereof, from the same species as the lymphocyte.

In certain embodiments, the amino acid sequence of the transmembrane region and cytoplasmic region together of the recombinant co-receptor, or a first chain thereof, can be at least 90% identical, optionally 91, 92, 93, 94, 95, 96, 97, 98, 99, or 100% identical, to the amino acid sequence of a corresponding transmembrane region and cytoplasmic region together of a naturally occurring co-receptor, or a first chain thereof, from the same species as the lymphocyte.

In certain embodiments, the amino acid sequence of the extracellular region of the recombinant co-receptor, or a first chain thereof, is at least 90% identical, optionally 91, 92, 93, 94, 95, 96, 97, 98, 99, or 100% identical, to the amino acid sequence of a corresponding extracellular region of a naturally occurring co-receptor, or a first chain thereof, from a different species than the lymphocyte. In certain embodiments, the naturally occurring co-receptor, or a first chain thereof, from a different species than the lymphocyte is human.

In certain embodiments, the cytoplasmic region of the recombinant co-receptor, or a first chain thereof, is at least 90% identical, optionally 91, 92, 93, 94, 95, 96, 97, 98, 99, or 100% identical, to the amino acid sequence of a corresponding cytoplasmic region of a naturally occurring co-receptor, or a first chain thereof, from the same species as the lymphocyte, and/or the amino acid sequence of the transmembrane region and cytoplasmic region together of the recombinant co-receptor, or a first chain thereof, can be at least 90% identical, optionally 91, 92, 93, 94, 95, 96, 97, 98, 99, or 100% identical, to the amino acid sequence of a corresponding transmembrane region and cytoplasmic region together of a naturally occurring co-receptor, or a first chain thereof, from the same species as the lymphocyte, and, the amino acid sequence of the extracellular region of the recombinant co-receptor, or a first chain thereof, is at least 90% identical, optionally 91, 92, 93, 94, 95, 96, 97, 98, 99, or 100% identical, to the amino acid sequence of a corresponding extracellular region of a naturally occurring co-receptor, or a first chain thereof, from a different species than the lymphocyte. In one embodiment, the naturally occurring co-receptor, or a first chain thereof, from a different species than the lymphocyte is human.

In certain embodiments, the recombinant co-receptor is CD8 or CD4.

In certain embodiments, the cell as disclosed herein further comprises a second polynucleotide encoding a second chain of the recombinant co-receptor, wherein the second chain comprises an extracellular region, a transmembrane region, and a cytoplasmic region, wherein the extracellular region of the second chain is linked to the transmembrane region of the second chain, and the transmembrane region of the second chain is linked to the cytoplasmic region of the second chain. In certain embodiments, the amino acid sequence of the cytoplasmic region of the second chain is at least 90% identical, optionally 91, 92, 93, 94, 95, 96, 97, 98, 99, or 100% identical, to the amino acid sequence of a corresponding cytoplasmic region of a naturally occurring co-receptor chain from the same species as the lymphocyte. In certain embodiments, the amino acid sequence of the transmembrane region and cytoplasmic region together of the second chain is at least 90% identical, optionally 91, 92, 93, 94, 95, 96, 97, 98, 99, or 100% identical, to the amino acid sequence of a corresponding transmembrane region and cytoplasmic region together of a naturally occurring co-receptor chain from the same species as the lymphocyte. In certain embodiments, the amino acid sequence of the extracellular region of the second chain is at least 90% identical, optionally 91, 92, 93, 94, 95, 96, 97, 98, 99, or 100% identical, to the amino acid sequence of a corresponding extracellular region of a naturally occurring co-receptor chain from a different species than the lymphocyte. The naturally occurring co-receptor chain can be from a different species than the lymphocyte is human.

Therefore, in certain embodiments, the amino acid sequence of the cytoplasmic region of the second chain is at least 90% identical, optionally 91, 92, 93, 94, 95, 96, 97, 98, 99, or 100% identical, to the amino acid sequence of a corresponding cytoplasmic region of a naturally occurring co-receptor chain from the same species as the lymphocyte, and/or the amino acid sequence of the transmembrane region and cytoplasmic region together of the second chain is at least 90% identical, optionally 91, 92, 93, 94, 95, 96, 97, 98, 99, or 100% identical, to the amino acid sequence of a corresponding transmembrane region and cytoplasmic region together of a naturally occurring co-receptor chain from the same species as the lymphocyte, and the amino acid sequence of the extracellular region of the second chain is at least 90% identical, optionally 91, 92, 93, 94, 95, 96, 97, 98, 99, or 100% identical, to the amino acid sequence of a corresponding extracellular region of a naturally occurring co-receptor chain from a different species than the lymphocyte. In one embodiment, the naturally occurring co-receptor chain from a different species than the lymphocyte is human.

In certain embodiments, the recombinant co-receptor is CD8. In certain embodiments, the cytoplasmic region of the first chain of the recombinant co-receptor comprises the amino acid sequence of residues 183-212 of SEQ ID NO: 1. In certain embodiments, the transmembrane region and the cytoplasmic region of the first chain of the recombinant co-receptor together comprise the amino acid sequence of residues 162-212 of SEQ ID NO: 1. In certain embodiments, the extracellular region of the first chain of the recombinant co-receptor comprises the amino acid sequence of residues 1-161 of SEQ ID NO: 1. In certain embodiments, the cytoplasmic region of the second chain of the recombinant co-receptor comprises the amino acid sequence of residues 171-187 of SEQ ID NO: 2. In certain embodiments, the transmembrane region and the cytoplasmic region of the second chain of the recombinant co-receptor together comprise the amino acid sequence of residues 150-187 of SEQ ID NO: 2. In certain embodiments, the extracellular region of the second chain of the recombinant co-receptor comprises the amino acid sequence of residues 1-149 of SEQ ID NO: 2. Therefore, in certain embodiments, the cytoplasmic region of the first chain of the recombinant co-receptor comprises the amino acid sequence of residues 183-212 of SEQ ID NO: 1, and/or the transmembrane region and the cytoplasmic region of the first chain of the recombinant co-receptor together comprise the amino acid sequence of residues 162-212 of SEQ ID NO: 1, for example, wherein the extracellular region of the first chain of the recombinant co-receptor comprises the amino acid sequence of residues 1-161 of SEQ ID NO: 1. In one embodiment, the cytoplasmic region of the second chain of the recombinant co-receptor comprises the amino acid sequence of residues 171-187 of SEQ ID NO: 2, and/or the transmembrane region and the cytoplasmic region of the second chain of the recombinant co-receptor together comprise the amino acid sequence of residues 150-187 of SEQ ID NO: 2. In one embodiment, the extracellular region of the second chain of the recombinant co-receptor comprises the amino acid sequence of residues 1-149 of SEQ ID NO: 2.

In certain embodiments, the recombinant co-receptor is a chimeric CD8 comprising: a) a chimeric CD8α chain comprising an extracellular region of human CD8α and transmembrane and cytoplasmic regions of mouse CD8α, and b) a chimeric CD8β chain comprising an extracellular region of human CD8β and transmembrane and cytoplasmic regions of mouse CD8β. In one embodiment, the chimeric CD8α chain comprises the amino acid sequence of SEQ ID NO: 1, and the chimeric CD8β chain comprises the amino acid sequence of SEQ ID NO: 2, for example, wherein the amino acid sequence of the chimeric CD8α chain consists of the amino acid sequence of SEQ ID NO: 1, and the amino acid sequence of the chimeric CD8β chain consists of the amino acid sequence of SEQ ID NO: 2.

In another aspect, the disclosure also provides an isolated cell derived from a mouse lymphocyte, the cell comprising: a) a first polynucleotide encoding a chimeric CD8α chain comprising an extracellular region of human CD8α and transmembrane and cytoplasmic regions of mouse CD8α, and b) a second polynucleotide encoding a chimeric CD8β chain comprising an extracellular region of human CD8β and transmembrane and cytoplasmic regions of mouse CD8β, wherein the cell expresses CD3 but does not express endogenous TCR on the cell surface. In certain embodiments, the chimeric CD8α chain comprises the amino acid sequence of SEQ ID NO: 1, and the chimeric CD8β chain comprises the amino acid sequence of SEQ ID NO: 2. In certain embodiments, the amino acid sequence of the chimeric CD8α chain consists of the amino acid sequence of SEQ ID NO: 1, and the amino acid sequence of the chimeric CD8β chain consists of the amino acid sequence of SEQ ID NO: 2.

In certain embodiments, the surface expression of the recombinant co-receptor or chain thereof is regulatable.

In certain embodiments, the first polynucleotide is flanked by a first pair of compatible site-specific recombination sequences.

In certain embodiments, the second polynucleotide is flanked by a second pair of compatible site-specific recombination sequences.

In certain embodiments, a portion of the first polynucleotide, the portion encoding the transmembrane region and/or the cytoplasmic region, is flanked by a first pair of compatible site-specific recombination sequences.

In certain embodiments, a portion of the second polynucleotide, the portion encoding the transmembrane region and/or the cytoplasmic region, is flanked by a second pair of compatible site-specific recombination sequences.

In certain embodiments, the first pair of compatible site-specific recombination sequences does not cross-react with the second pair of compatible site-specific recombination sequences.

In certain embodiments, the surface expression of the recombinant co-receptor, or chain thereof, can be attenuated by contacting the first polynucleotide and/or the second polynucleotide with a cognate site-specific recombinase that recognizes the first pair of compatible site-specific recombination sequences of the first polynucleotide and/or the second pair of compatible site-specific recombination sequences of the second polynucleotide.

In certain embodiments, the surface expression of the recombinant co-receptor, or chain thereof, can be abrogated by contacting the first polynucleotide and/or the second polynucleotide with a cognate site-specific recombinase that recognizes the first pair of compatible site-specific recombination sequences of the first polynucleotide and/or the second pair of compatible site-specific recombination sequences of the second polynucleotide.

Therefore, in certain embodiments, the first pair of compatible site-specific recombination sequences does not cross-react with the second pair of compatible site-specific recombination sequences, for example, wherein the surface expression of the recombinant co-receptor, or chain thereof, can be attenuated by contacting the first polynucleotide and/or the second polynucleotide with a cognate site-specific recombinase that recognizes the first pair of compatible site-specific recombination sequences of the first polynucleotide and/or the second pair of compatible site-specific recombination sequences of the second polynucleotide, or wherein the surface expression of the recombinant co-receptor, or chain thereof, can be abrogated by contacting the first polynucleotide and/or the second polynucleotide with a cognate site-specific recombinase that recognizes the first pair of compatible site-specific recombination sequences of the first polynucleotide and/or the second pair of compatible site-specific recombination sequences of the second polynucleotide.

In certain embodiments, the cell further comprises a third polynucleotide encoding a cognate site-specific recombinase that recognizes the first and/or the second pair of compatible site-specific recombination sequences. In certain embodiments, the transcription of the third polynucleotide is regulated by an inducible promoter.

In certain embodiments, the first and second pairs of site-specific recombination sequences are compatible pairs of lox sites and the cognate site-specific recombinase is a Cre recombinase.

In certain embodiments, the compatible pairs of lox sites are compatible pairs of loxP sites. Therefore, in one embodiment, the first and second pairs of site-specific recombination sequences are compatible pairs of lox sites and the cognate site-specific recombinase is a Cre recombinase, for example, wherein the compatible pairs of lox sites are compatible pairs of loxP sites.

In certain embodiments, the recombinant co-receptor is CD8. In certain embodiments, the first polynucleotide comprises the polynucleotide sequence of residues 1-675 of SEQ ID NO: 3. In certain embodiments, the first polynucleotide comprises the polynucleotide sequence of SEQ ID NO: 3. In certain embodiments, the second polynucleotide comprises the polynucleotide sequence of residues 1-600 of SEQ ID NO: 4. In certain embodiments, the second polynucleotide comprises the polynucleotide sequence of SEQ ID NO: 4. In certain embodiments, the first chain of the recombinant co-receptor comprises the amino acid sequence of SEQ ID NO: 25. In certain embodiments, the first chain of the recombinant co-receptor comprises the amino acid sequence of SEQ ID NO: 5. In certain embodiments, the second chain of the recombinant co-receptor comprises the amino acid sequence of SEQ ID NO: 26. In certain embodiments, the second chain of the recombinant co-receptor comprises the amino acid sequence of SEQ ID NO: 6. Therefore, in one embodiment of the present invention, the recombinant co-receptor is CD8, for example, wherein the first polynucleotide comprises the polynucleotide sequence of residues 1-675 of SEQ ID NO: 3 or the first polynucleotide comprises the polynucleotide sequence of SEQ ID NO: 3, and/or wherein the second polynucleotide comprises the polynucleotide sequence of residues 1-600 of SEQ ID NO: 4 or the second polynucleotide comprises the polynucleotide sequence of SEQ ID NO: 4. In another embodiment, the recombinant co-receptor is CD8, and the first chain of the recombinant co-receptor comprises the amino acid sequence of SEQ ID NO: 25 or SEQ ID NO: 5, and/or the second chain of the recombinant co-receptor comprises the amino acid sequence of SEQ ID NO: 26 or SEQ ID NO: 6.

In certain embodiments, the transcription of the first polynucleotide is regulated by an inducible promoter, and/or the transcription of the second polynucleotide is regulated by an inducible promoter.

In certain embodiments, the cell further comprises one or more reporter systems. In certain embodiments, the one or more reporter systems provide an indication of one or more activities of the cell selected from the group consisting of nuclear factor of activated T-cell (NFAT) signaling, activator protein-1 (AP1) signaling, NFκB/Rel signaling, and calcium flux. In certain embodiments, the one or more reporter systems comprise a polynucleotide comprising a promoter region operably linked to a polynucleotide sequence encoding a detectable marker. In certain embodiments, the promoter region comprises one or more transcriptional response elements selected from the group consisting of nuclear factor of activated T-cell (NFAT) response elements, activator protein-1 (AP1) response elements, and NFκB/Rel response elements. In certain embodiments, the detectable marker is selected from the group consisting of a fluorescent protein, a cell surface marker, and an antibiotic selection marker. In certain embodiments, the promoter region is an IL-2 promoter. In certain embodiments, the IL-2 promoter is a minimal IL-2 promoter. In certain embodiments, the IL-2 promoter comprises one or more NFAT binding sites. In certain embodiments, the IL-2 promoter comprises three NFAT binding sites. In certain embodiments, the detectable marker is enhanced green fluorescent protein (EGFP). In certain embodiments, the promoter region is an IL-2 promoter comprising three NFAT binding sites and the detectable marker is enhanced green fluorescent protein (EGFP).

In certain embodiments, the cell is derived from a single cell, wherein when the cell is expanded to a plurality of cells of at least $10^5$ and transduced or transfected with separate polynucleotide vectors encoding a TCR α chain and a TCR β chain to express a recombinant TCR comprising the TCR α chain and the TCR β chain under conditions that maximize transduction or transfection efficiency, at least 20% of the plurality of cells express the recombinant TCR on the cell surface. In certain embodiments, the cell has previously been subjected to one or more rounds of transduction or transfection.

In certain embodiments, the lymphocyte is a T cell, B cell, or an NK cell. In certain embodiments, the lymphocyte is a T cell that is selected from the group consisting of a CD8+ cytotoxic T cell, a CD8+ regulatory T cell, a CD4+ cytotoxic T cell, a CD4+ helper T cell and a CD4+ regulatory T cell. In certain embodiments, the lymphocyte is a mammalian lymphocyte. In certain embodiments, the lymphocyte is a murine lymphocyte. In certain embodiments, the lymphocyte is selected from the group consisting of a RAG1 or RAG2 knockout murine cell, an immature murine T cell, a mouse DO-11.10.7 58 α− β− (58−/−) cell, and a mouse Bw5147 cell. In certain embodiments, the lymphocyte is a mouse lymphocyte. Therefore, in another embodiment of a cell of the present invention, the lymphocyte is a T cell, B cell, or an NK cell, for example, the lymphocyte is a T cell that is selected from the group consisting of a CD8+ cytotoxic T cell, a CD8+ regulatory T cell, a CD4+ cytotoxic T cell, a CD4+ helper T cell and a CD4+ regulatory T cell, and/or wherein the lymphocyte is a mammalian lymphocyte, for example, a murine lymphocyte, such as a lymphocyte selected from the group consisting of a RAG1 or RAG2 knockout murine lymphocyte, an immature murine T cell, a mouse DO-11.10.7 58 α− β− (58−/−) cell, and a mouse Bw5147 cell. In one embodiment, the lymphocyte is a mouse lymphocyte.

In certain embodiments, the cell further expresses a recombinant TCR on the cell surface, the recombinant TCR comprising a TCR α chain and a TCR β chain, wherein the TCR α chain and the TCR β chain each comprises a variable region and a non-variable region, each non-variable region comprising a constant region, a transmembrane region, and a cytoplasmic region, wherein for each chain, the variable region is linked to the constant region, the constant region is linked to the transmembrane region, and the transmembrane region is linked to the cytoplasmic region. In certain embodiments, for each of the TCR α chain and the TCR β chain, the amino acid sequence of the cytoplasmic region is at least 60% identical, optionally 70, 80, 90, or 100% identical, to the amino acid sequence of a corresponding cytoplasmic region of a naturally occurring TCR chain from the same species as the lymphocyte. In certain embodiments, for each of the TCR α chain and the TCR β chain, the amino acid sequence of the transmembrane region and the cytoplasmic region, together, is at least 90% identical, optionally 91, 92, 93, 94, 95, 96, 97, 98, 99, or 100% identical, to the amino acid sequence of a corresponding region of a naturally occurring TCR chain from the same species as the lymphocyte. In certain embodiments, the amino acid sequence of the transmembrane region and the cytoplasmic region of the TCR α chain, together, comprises the amino acid sequence of SEQ ID NO: 14. In certain embodiments, the amino acid sequence of the transmembrane region and the cytoplasmic region of the TCR β chain, together, comprises the amino acid sequence selected from the group consisting of SEQ ID NOs: 16, 18 and 20. In certain embodiments, for each of the TCR α chain and the TCR β chain, the amino acid sequence of the non-variable region is at least 90% identical, optionally 91, 92, 93, 94, 95, 96, 97, 98, 99, or 100% identical, to the amino acid sequence of a corresponding non-variable region of a naturally occurring TCR chain from the same species as the lymphocyte. In certain embodiments, the non-variable region of the TCR α chain comprises the amino acid sequence of SEQ ID NO: 13. In certain embodiments, the non-variable region of the TCR β chain comprises the amino acid sequence selected from the group consisting of SEQ ID NOs: 15, 17, and 19.

Therefore, in certain embodiments, the cell further expresses a recombinant TCR on the cell surface, the recombinant TCR comprising a TCR α chain and a TCR β chain, wherein the TCR α chain and the TCR β chain each comprises a variable region and a non-variable region, each non-variable region comprising a constant region, a transmembrane region, and a cytoplasmic region, wherein for each chain, the variable region is linked to the constant region, the constant region is linked to the transmembrane region, and the transmembrane region is linked to the cytoplasmic region. In one embodiment, for each of the TCR α chain and the TCR β chain, the amino acid sequence of the cytoplasmic region is at least 60% identical, optionally 70, 80, 90, or 100% identical, to the amino acid sequence of a corresponding cytoplasmic region of a naturally occurring TCR chain from the same species as the lymphocyte. In another embodiment, for each of the TCR α chain and the TCR β chain, the amino acid sequence of the transmembrane region and the cytoplasmic region, together, is at least 90% identical, optionally 91, 92, 93, 94, 95, 96, 97, 98, 99, or 100% identical, to the amino acid sequence of a corresponding region of a naturally occurring TCR chain from the same species as the lymphocyte, for example, wherein the amino acid sequence of the transmembrane region and the cytoplasmic region of the TCR α chain, together, comprises the amino acid sequence of SEQ ID NO: 14, and/or wherein the amino acid sequence of the transmembrane region and the cytoplasmic region of the TCR β chain, together, comprises the amino acid sequence selected from the group consisting of SEQ ID NOs: 16, 18 and 20. In another embodiment, for each of the TCR α chain and the TCR β chain, the amino acid sequence of the non-variable region is at least 90% identical, optionally 91, 92, 93, 94, 95, 96, 97, 98, 99, or 100% identical, to the amino acid sequence of a corresponding non-variable region of a naturally occurring TCR chain from the same species as the lymphocyte, for example, wherein the non-variable region of the TCR α chain comprises the amino acid sequence of SEQ ID NO: 13, and/or the non-variable region of the TCR β chain comprises the amino acid sequence selected from the group consisting of SEQ ID NOs: 15, 17, and 19.

In certain embodiments, the amino acid sequence of each variable region is derived from a corresponding variable region of a TCR chain from a different species than the lymphocyte. In one embodiment, the TCR from a different species than the lymphocyte is human.

In certain embodiments, the amino acid sequence of each variable region is derived from a corresponding variable region of a TCR chain from a different species than the lymphocyte, for example, wherein for each of the TCR α chain and the TCR β chain, the amino acid sequence of the variable region and the constant region, together, is derived from a corresponding region of a TCR chain from a different species than the lymphocyte. In one embodiment, the TCR from a different species than the lymphocyte is human.

In certain embodiments, the recombinant TCR is a fusion molecule comprising a co-stimulatory signaling region. In certain embodiments, the co-stimulatory signaling region is fused to the cytoplasmic region of the TCR α chain or the cytoplasmic region of the TCR β chain. In certain embodiments, the co-stimulatory signaling region comprises the signaling region of a co-stimulatory molecule selected from the group consisting of CD27, CD28, 4-1BB, OX40, CD30, CD40, ICOS, lymphocyte function-associated antigen-1 (LFA-1), CD2, CD7, LIGHT, NKG2C, NKG2D, B7-H3, and a ligand that specifically binds CD83. In certain embodiments, the co-stimulatory signaling region comprises the signaling region of CD28, the signaling region of 4-1BB, or a combination thereof. In certain embodiments, the fusion molecule further comprises a CD3ζ signaling region.

Therefore, in certain embodiments, the recombinant TCR is a fusion molecule comprising a co-stimulatory signaling region, for example, wherein the co-stimulatory signaling region is fused to the cytoplasmic region of the TCR α chain or the cytoplasmic region of the TCR β chain, and/or wherein the co-stimulatory signaling region comprises the signaling region of a co-stimulatory molecule selected from the group consisting of CD27, CD28, 4-1BB, OX40, CD30, CD40, ICOS, lymphocyte function-associated antigen-1 (LFA-1), CD2, CD7, LIGHT, NKG2C, NKG2D, B7-H3, and a ligand that specifically binds CD8β. In one embodiment, the co-stimulatory signaling region comprises the signaling region of CD28, the signaling region of 4-1BB, or a combination thereof, and/or the fusion molecule further comprises a CD3ζ signaling region.

In certain embodiments, the expression of the recombinant TCR is coupled to the expression of (1) at least one antibiotic selection marker; (2) at least one screening marker; or (3) a combination thereof, for example, wherein the at least one screening marker is a fluorescent protein or a cell surface marker.

In certain embodiments, the recombinant TCR is derived from a source selected from the group consisting of fetal thymus, cord blood, tumor infiltrating lymphocytes (TILs) isolated from a cancer patient, a vaccinated subject, a subject naturally exposed to an antigen of interest, a healthy subject, and a synthetic library, for example, wherein the vaccinated subject is a human who has received an HPV vaccine, an EBV vaccine, or a cancer vaccine, or the vaccinated subject is a transgenic mouse expressing human major histocompatibility complex (MHC) that has been immunized with an antigen of interest, and/or wherein the vaccinated subject is a transgenic mouse expressing HLA-A2 that has been immunized with an antigen of interest.

In certain embodiments of the present invention described above, the cell expresses (1) a recombinant TCR α chain and a recombinant TCR β chain, (2) a recombinant TCR α chain and multiple different recombinant TCR β chains, (3) a recombinant TCR β chain and multiple different recombinant TCR α chains, or (4) multiple different recombinant TCR α chains and multiple different recombinant TCR β chains.

In another aspect, the disclosure also provides a cellular library comprising a plurality of any one of the cells disclosed herein. In certain embodiments, the cellular library has a TCR diversity of at least $10^7$, $10^8$, or $10^9$. In another aspect, the present invention relates to a cellular library comprising a plurality of any one of the cells of the invention, wherein the cell further expresses a cellular TCR on the cell surface. The embodiments disclosed herein for a cell of the invention also apply to a cellular library of the invention.

In another aspect, the disclosure also provides a method for the isolation and identification of a TCR with a desired characteristic comprising subjecting a plurality of any one of the cells or the cellular libraries disclosed herein to a selection process comprising selecting for the desired characteristic in the presence of a desired peptide-MHC complex, isolating a cell that expresses a TCR, and determining that the TCR of the isolated cell has the desired characteristic. The embodiments disclosed herein for a cell of the invention wherein the cell further expresses a cellular TCR on the cell surface and the embodiments disclosed herein for a cellular library of the invention also apply to the method of the invention.

In another aspect, the disclosure also provides a method for the identification of at least one polynucleotide encoding a TCR with a desired characteristic, comprising: (a) providing a plurality of any one of the cells disclosed, (b) transducing or transfecting the cells with a plurality of expression constructs encoding a plurality of TCRs, (c) expressing the TCRs on the surface of the cells, (d) selecting cells expressing the TCRs for the desired characteristic in the presence of a desired peptide-MHC complex, (e) isolating the at least one polynucleotide encoding the TCR with the desired characteristic from the selected cells, and (f) identifying the at least one polynucleotide encoding the TCR with the desired characteristic isolated in step (e). The embodiments disclosed herein for a cell of the invention also apply to the method of the invention. Preferably, the method is an in vitro method.

In another aspect, the disclosure also provides a method for the identification of at least one polynucleotide encoding a TCR with a desired characteristic, comprising: (a) providing a plurality of any one of the cells disclosed herein; (b) transducing or transfecting the cells with a plurality of expression constructs encoding a plurality of TCRs, (c) expressing the TCRs on the surface of the cells, (d) selecting cells expressing the TCRs for the desired characteristic in the presence of a desired peptide-MHC complex, (e) modulating an activity of the recombinant co-receptor or chain thereof in the cells selected in step (d), (f) further selecting cells expressing the TCRs produced by step (e) for the desired characteristic in the presence of the desired peptide-MHC complex, (g) isolating the at least one polynucleotide encoding the TCR with the desired characteristic from the cells selected in step (f), and (h) identifying the at least one polynucleotide encoding the TCR with the desired characteristic isolated in step (g). The embodiments disclosed herein for a cell of the invention also apply to the method of the invention. Preferably, the method is an in vitro method.

In certain embodiments, step (d) is performed in the presence of surface expression of the recombinant co-receptor or chain thereof, and step (e) comprises abrogation of cell surface expression of the recombinant co-receptor or chain thereof.

In certain embodiments, the plurality of cells of step (a) comprise the any one of cells disclosed herein, and in step (e), the cell surface expression of the recombinant co-receptor or chain thereof is abrogated by contacting the site-specific recombination sequences in the first and/or second polynucleotide with a cognate site-specific recombinase. In certain embodiments, the cognate site-specific recombinase is expressed in the cells under the control of an inducible promoter. In certain embodiments, the cognate site-specific recombinase is introduced into the cells selected in step (d) prior to step (e). In certain embodiments, the cognate site-specific recombinase is introduced by transfecting or transducing the cells selected in step (d) with an expression construct encoding the site-specific recombinase. In certain embodiments, the cognate site-specific recombinase is introduced as a protein. In certain embodiments, the site-specific recombination sequences are lox sites and the cognate site-specific recombinase is a Cre recombinase. In certain embodiments, the site-specific recombination sequences are lox sites and the cognate site-specific recombinase is a Cre recombinase fusion protein comprising a protein transduction domain. In certain embodiments, the protein transduction domain is from HIV Tat. Therefore, in certain embodiments of the methods of the invention, step (d) is performed in the presence of surface expression of the recombinant co-receptor or chain thereof, and step (e) comprises abrogation of cell surface expression of the recombinant co-receptor or chain thereof, for example, wherein the plurality of cells of step (a) comprise the any one of cells disclosed herein, and wherein in step (e), the cell surface expression of the recombinant co-receptor or chain thereof is abrogated by contacting the site-specific recombination sequences in the first and/or second polynucleotide with a cognate site-specific recombinase, and/or wherein the cognate site-specific recombinase is expressed in the cells under the control of an inducible promoter. In another embodiment, the cognate site-specific recombinase is introduced into the cells selected in step (d) prior to step (e), in particular, wherein the cognate site-specific recombinase is introduced by transfecting or transducing the cells selected in step (d) with an expression construct encoding the site-specific recombinase, or wherein the cognate site-specific recombinase is introduced as a protein. In one embodiment, the site-specific recombination sequences are lox sites and the cognate site-specific recombinase is a Cre recombinase, for example, wherein the site-specific recombination sequences are lox sites and the cognate site-specific recombinase is a Cre recombinase fusion protein comprising a protein transduction domain, in particular wherein the protein transduction domain is from HIV Tat.

In another aspect, the disclosure also provides a method for the identification of at least one polynucleotide encoding a TCR with a desired characteristic, comprising: (a) providing a plurality of cells any one of the cells disclosed herein, (b) transducing or transfecting the cells with a plurality of expression constructs encoding a plurality of TCRs, (c) expressing the TCRs on the surface of the cells, (d) selecting cells expressing the TCRs for the desired characteristic in the presence of an MHC molecule complexed with a peptide of interest, wherein the MHC molecule is a variant of a wild type MHC molecule, wherein the variant MHC molecule binds to a co-receptor with reduced affinity compared to the affinity of the wild type MHC molecule for the co-receptor, (e) isolating the at least one polynucleotide encoding the TCR with the desired characteristic from the cells selected in step (d), and (f) identifying the at least one polynucleotide encoding the TCR with the desired characteristic isolated in step (e). The embodiments disclosed herein for a cell of the invention also apply to the method of the invention. Preferably, the method is an in vitro method.

In certain embodiments of any of the methods described above, the co-receptor is CD8 and the variant MHC molecule is a variant MHC class I molecule comprising an $\alpha$ chain that is a variant of a wild type MHC class I $\alpha$ chain, for example, wherein the co-receptor is human CD8 and the variant MHC class I molecule is a variant HLA-A2 comprising an $\alpha$ chain that is a variant of wild type HLA-A2 $\alpha$ chain, and/or wherein the variant HLA-A2 $\alpha$ chain comprises an A245V mutation or a D227K/T228A mutation, numbered according to the mature protein sequence.

In certain embodiments of any of the methods described above, the desired characteristic is selected from the group consisting of high selectivity for the desired peptide-MHC complex, high affinity for the desired peptide-MHC complex, and demonstration of a positive functional readout in the presence of the desired peptide-MHC complex. In certain embodiments, the functional readout is selected from the group consisting of expression of activation marker, triggering of signaling pathway, production of cytokine, calcium flux, proliferation, and activation of reporter system. In certain embodiments, the activation marker is CD69 or CD137. In certain embodiments, the signaling pathway is NFAT signaling, IL-2 signaling, activator protein-1 signaling, or NFκB/Rel signaling. In certain embodiments, the cytokine is IL-2, TNF-$\alpha$, or IFN-$\gamma$. In certain embodiments, the proliferation is proliferation of T cells. In certain embodiments, the functional readout is the activation of one or more reporter systems in the cells. In certain embodiments, the reporter system is IL-2-EGFP reporter system. Therefore, certain embodiments of any of the methods of the invention described above, the desired characteristic is selected from the group consisting of high selectivity for the desired peptide-MHC complex, high affinity for the desired peptide-MHC complex, and demonstration of a positive functional readout in the presence of the desired peptide-MHC complex, for example, wherein the functional readout is selected from the group consisting of expression of activation marker, triggering of signaling pathway, production of cytokine, calcium flux, proliferation, and activation of reporter system, in particular a reporter system as described above for a cell of the invention, for example, wherein the activation marker is CD69 or CD137. In one embodiment, the signaling pathway is NFAT signaling, IL-2 signaling, activator protein-1 signaling, or NFκB/Rel signaling. In one embodiment, the cytokine is IL-2, TNF-$\alpha$, or IFN-$\gamma$. In one embodiment, the proliferation is proliferation of T cells. In one embodiment, the functional readout is the activation of one or more reporter systems in the cells. In one embodiment, the reporter system is IL-2-EGFP reporter system.

In certain embodiments of any of the methods described above, the plurality of expression constructs encode (i) a TCR $\alpha$ chain and a TCR $\beta$ chain, (ii) a TCR $\alpha$ chain and multiple different TCR $\beta$ chains, (iii) a TCR $\beta$ chain and multiple different TCR $\alpha$ chains, or (iv) multiple different TCR $\alpha$ chains and multiple different TCR $\beta$ chains.

In certain embodiments of any of the methods described above, the desired peptide-MHC complex comprises an MHC class I or MHC class II molecule. In certain embodiments, the desired peptide-MHC complex is a cell free peptide-MHC complex. In certain embodiments, the desired peptide-MHC complex comprises a dimer, a tetramer, or a multimer of MHC molecules. In certain embodiments, the desired peptide-MHC complex is displayed on the surface of a cell. In a exemplary embodiment of any of the methods of the invention described above, the desired peptide-MHC complex is displayed on the surface of a cell, for example, wherein the cell is a mammalian cell, a yeast cell, or an insect cell, or the cell is a T2 cell or an antigen-presenting cell. In certain embodiments, the cell is a mammalian cell, a yeast cell, or an insect cell. In certain embodiments, the cell is a T2 cell or an antigen-presenting cell. Therefore, in one embodiment of any of the methods of the invention described above, the desired peptide-MHC complex comprises an MHC class I or MHC class II molecule, and/or the desired peptide-MHC complex is a cell free peptide-MHC complex, in particular wherein the desired peptide-MHC complex comprises a dimer, a tetramer, or a multimer of MHC molecules.

In certain embodiments of any of the methods described above, the peptide is a phosphopeptide or a phosphopeptide mimetic.

In certain embodiments of any of the methods described above, in step (b), the plurality of expression constructs encoding a plurality of TCRs is transduced into the cells using retroviral vector particles comprising an envelope of PVC-211 murine leukemia virus, wherein the retroviral vector particle comprises a retroviral expression construct encoding the TCR α chain or the TCR β chain.

In certain embodiments of any of the methods described above, each TCR comprises a TCR α chain and a TCR β chain, wherein the TCR α chain and the TCR β chain are encoded by separate expression constructs.

BRIEF DESCRIPTION OF THE FIGURES

FIG. 2A is a set of flow cytometry plots showing the co-staining of PE-labeled HLA-A*0201 Mart-1 tetramer and APC-labeled anti-TCR β chain antibody on AK-D10 cells, AK-D10 cells expressing chimeric DMF4 (AK-D10 chiDMF4), and AK-D10 cells expressing chimeric DMF5 (AK-D10 chiDMF5). The percentage of tetramer+ TCR+ cells is indicated in each plot. The rightmost plot shows an overlay of the AK-D10 chiDMF4 cells and the AK-D10 chiDMF5 cells. FIGS. 2B and 2C are bar graphs showing relative IL-2 production measured by ELISA following overnight incubation of the AK-D10 chiDMF4 cells (FIG. 2B) or the AK-D10 chiDMF5 cells (FIG. 2C) with DimerX loaded with a Mart-1 peptide ELAGIGILTV (SEQ ID NO: 30) (DimerX/Mart-1) or DimerX alone without any peptide (DimerX) at indicated concentrations. The y axis shows optical density (OD) signal. FIGS. 2D and 2E are bar graphs showing results from intracellular staining of IL-2 and TNFα, respectively, of AK-D10 cells expressing chimeric TCR following overnight incubation with non-loaded DimerX (grey bars) or DimerX loaded with a Mart-1 peptide ELAGIGILTV (SEQ ID NO: 30) (for AK-D10 chiDMF4 and AK-D10 chiDMF5) or a NY-ESO-1 peptide SLLMWITQV (SEQ ID NO: 31) (for AK-D10 chiC58) (black bars). The y-axis shows the percentage (%) of TCR+IL-2+(FIG. 2D) or TCR+ TNFα+(FIG. 2E) cells.

FIGS. 4A and 4B are a set of flow cytometry plots showing BB8 cells expressing chimeric DMF4 either transduced to express a Cre recombinase (bottom) or not transduced (top). The pairs of parameters shown on the X and Y axes are indicated in the figures. FIG. 4C is a bar graph showing binding of HLA-A*02:01 Mart-1 tetramer to BB8 cells expressing chimeric DMF4 or DMF5. The cells were either transduced to express a Cre recombinase (marked as "CD8−") or not transduced (marked as "CD8+"). The y-axis shows median fluorescence intensity (MFI) detected for tetramer binding as measured by flow cytometry.

DETAILED DESCRIPTION

Figure 1:
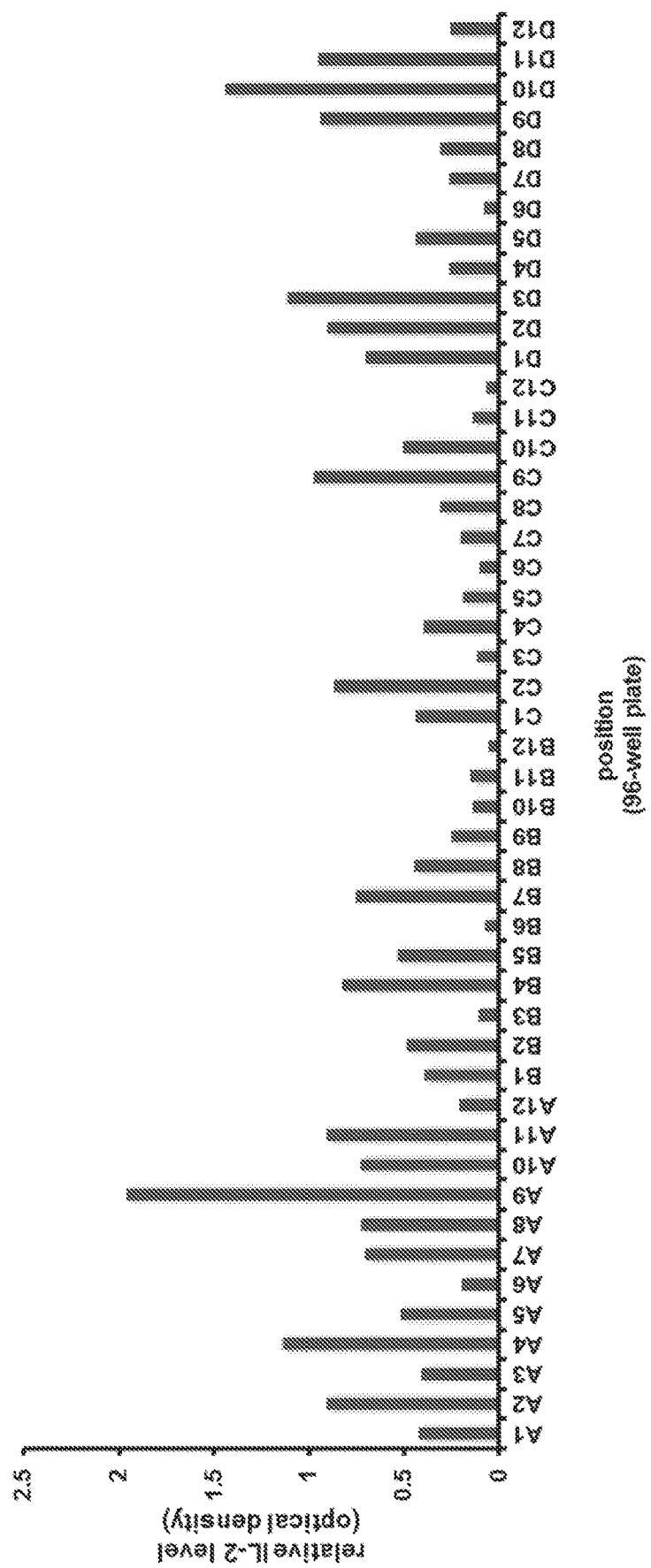
FIG. 1 is a bar graph showing relative IL-2 levels in culture supernatant measured by ELISA after overnight co-incubation of MTCD8 mCD8αβ− chiCD8αβ+ chiC58αβ+ cells with anti-CD3 and anti-CD28 antibodies. The y-axis shows optical density (OD) signal.

Disclosed herein are methods for the generation and screening of highly diversified T cell receptor (TCR) cellular libraries, allowing for the rapid identification and isolation of antigen-reactive therapeutic TCRs for immune therapy applications.

In a preferred embodiment of the present invention, a cell according to the present invention is not a human embryonic cell.

All instances of "isolated cells" described herein are additionally contemplated as cells that may be, but need not be, isolated. All instances of "isolated polynucleotides" described herein are additionally contemplated as polynucleotides that may be, but need not be, isolated. All instances of "cells" described herein are additionally contemplated as cells that may be, but need not be, isolated. All instances of "polynucleotides" described herein are additionally contemplated as polynucleotides that may be, but need not be, isolated.

I. DEFINITIONS

Unless otherwise defined herein, scientific and technical terms used herein have the meanings that are commonly understood by those of ordinary skill in the art. In the event of any latent ambiguity, definitions provided herein take precedence over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

It is noted here that as used in this specification and the appended claims, the singular forms "a", "an", and "the" also include plural reference, unless the context clearly dictates otherwise.

The term "about" or "approximately" means within 10%, and more preferably within 5% (or 1% or less) of a given value or range.

As used herein, the term "isolated cell" refers to a cell that has been removed from its in-vivo location.

As used herein, the terms "T cell receptor" and "TCR" are used interchangeably and refer to full length heterodimeric αβ or γδ TCRs, antigen-binding fragments of TCRs, and molecules comprising TCR CDRs or variable regions. Examples of TCRs include, but are not limited to, full-length TCRs, antigen-binding fragments of TCRs, soluble TCRs lacking transmembrane and cytoplasmic regions, single-chain TCRs containing variable regions of TCRs attached by a flexible linker, TCR chains linked by an engineered disulfide bond, monospecific TCRs, multi-specific TCRs (including bispecific TCRs), TCR fusions, human TCRs, humanized TCRs, chimeric TCRs, recombinantly produced TCRs, and synthetic TCRs. The term encompasses wild-type TCRs and genetically engineered TCRs (e.g., a chimeric TCR comprising a chimeric TCR chain which includes a first portion from a TCR of a first species and a second portion from a TCR of a second species).

As used herein, the term "TCR variable region" is understood to encompass amino acids of a given TCR which are not included within the non-variable region as encoded by the TRAC gene for TCR α chains and either the TRBC1 or TRBC2 genes for TCR β chains. In some embodiments, a TCR variable region encompasses all amino acids of a given TCR which are encoded by a TRAV gene or a TRAJ gene for a TCR α chain or a TRBV gene, a TRBD gene, or a TRBJ gene for a TCR β chain (see, e.g., T cell receptor Factsbook, (2001) LeFranc and LeFranc, Academic Press, ISBN 0-12-441352-8, which is incorporated by reference herein in its entirety).

As used herein, the term "constant region" with respect to a TCR refers to the extracellular portion of a TCR that is encoded by the TRAC gene for TCR α chains and either the TRBC1 or TRBC2 genes for TCR β chains. The term constant region does not include a TCR variable region encoded by a TRAV gene or a TRAJ gene for a TCR α chain or a TRBV gene, a TRBD gene, or a TRBJ gene for a TCR β chain (see, e.g., T cell receptor Factsbook, (2001) LeFranc and LeFranc, Academic Press, ISBN 0-12-441352-8, which is incorporated by reference herein in its entirety).

As used herein, the term a "recombinant" molecule refers to a molecule that is not naturally present in the cell in which it is expressed. In certain embodiments, the recombinant molecule, e.g., co-receptor or chain thereof, is from a different species than the cell in which it is expressed.

As used herein, the term an "endogenous" molecule refers to a molecule that is naturally present in the cell in which it is expressed.

As used herein, the term "co-stimulatory signaling region" refers to the intracellular portion of a co-stimulatory molecule that is responsible for mediating intracellular signaling events.

As used herein, the term "extracellular" with respect to a recombinant protein refers to the portion or portions of a recombinant transmembrane protein that are located outside of a cell.

As used herein, the term "transmembrane" with respect to a recombinant protein refers to the portion or portions of a recombinant transmembrane protein that are embedded in the plasma membrane of a cell.

As used herein, the term "cytoplasmic" with respect to a recombinant protein refers to the portion or portions of a recombinant protein that are located in the cytoplasm of a cell.

As used herein, the term "chimeric" protein refers to a recombinant protein in which a first region of a first recombinant protein is fused in frame, optionally with a peptide linker, with a second region of a second recombinant protein. In one embodiment, the first and second recombinant proteins are from the same species and the first region is different from the second region. In another embodiment, the first and second recombinant proteins are from different species.

As used herein, the term "CD3" refers to "cluster of differentiation 3", or functional portion thereof. An example of CD3 includes, but is not limited to, a complex comprising six polypeptides forming three dimers: CD3ε/CD3γ, CD3ε/CD3δ, and CD3ζ/CD3ζ.

As used herein, the term "CD8" refers to "cluster of differentiation 8", a co-receptor for TCR, or functional portion thereof. Examples of CD8 include, but are not limited to, a CD8α/CD8β heterodimer, a CD8α/CD8α homodimer, and a CD8β/CD8β homodimer. The term encompasses wild-type CD8 and genetically engineered CD8 (e.g., a chimeric CD8 comprising a chimeric CD8 chain which includes a first portion from a CD8 of a first species and a second portion from a CD8 of a second species).

As used herein, the term "CD4" refers to "cluster of differentiation 4", a co-receptor for TCR, or functional portion thereof. The term encompasses wild-type CD4 and genetically engineered CD4 (e.g., a chimeric CD4 comprising a first portion from a CD4 of a first species and a second portion from a CD4 of a second species).

As used herein, the term "co-receptor" refers to a cell surface molecule that binds to a peptide-MHC complex together with a TCR and potentiates T cell activation. Examples of co-receptors include, without limitation, CD4 and CD8.

As used herein, the term "internal ribosomal entry site (IRES) element" refers to a structure to which a ribosome can bind that does not need to be at the 5' end of the mRNA. It can therefore direct a ribosome to initiate translation at a second initiation codon within an mRNA, allowing more than one polypeptide to be produced from a single mRNA. Exemplary IRES elements include, but are not limited to, IRES elements isolated from poliovirus, rhinovirus, encephalomyocarditis virus, foot-and-mouth disease virus, hepatitis A and hepatitis C virus (see, for example, Mokrejs et al. (2006) Nucleic Acids Res. 34 (Database issue): D125-30, which is incorporated by reference herein in its entirety).

As used herein, the term "TCR engagement" refers to the binding of a TCR to its ligand. In certain embodiments, the ligand is a peptide-MHC complex.

As used herein, the terms "major histocompatibility complex" and "MHC" are used interchangeably and refer to an MHC class I molecule and/or an MHC class II molecule.

As used herein, the term "MHC class I" refers to a dimer of an MHC class I α chain and a β2-microglobulin chain and the term "MHC class II" refers to a dimer of an MHC class II α chain and an MHC class II β chain.

As used herein, the term "soluble MHC" refers to an MHC molecule lacking transmembrane and cytoplasmic regions.

As used herein, the term "peptide-MHC complex" refers to an MHC molecule (MHC class I or MHC class II) with a peptide bound in the art-recognized peptide binding pocket of the MHC.

As used herein, the terms "DO-11.10.7 58 α-β-cell" and "58−/− cell" are used interchangeably and refer to a mouse T cell hybridoma cell line as described in Letourneur and Malissen Eur J Immunol. 1989; 19(12):2269-74, which is incorporated by reference herein in its entirety.

As used herein, the term "T2 cell" refers to a human lymphoblast cell line as described in Salter R D, et al. Genes regulating HLA class I antigen expression in T-B lymphoblast hybrids. Immunogenetics 21: 235-246, 1985, which is incorporated by reference herein in its entirety.

As used herein, the term "Bw5147 cell" refers to a mouse T lymphocyte cell line as described in Ralph P. Retention of lymphocyte characteristics by myelomas and theta$^+$-lymphomas: sensitivity to cortisol and phytohemagglutinin. J. Immunol. 110: 1470-1475, 1973, which is incorporated by reference herein in its entirety.

As used herein the term "site-specific recombination" refers to a recombination event that is effected between two compatible sequence-specific recombination sites on a single nucleic acid molecule by a cognate site-specific recombinase. A pair of site-specific recombination sites are said to be "compatible" if the members of the pair can direct the recombination between the site-specific recombination sites by a cognate site-specific recombinase. In one embodiment, the recombination event results in the excision of the intervening nucleotide sequences between the site-specific recombination sites. Pairs of compatible site-specific recombination sites are said to be "non-cross-reactive" if any one pair of compatible site-specific recombination sites is unable to recombine with any other pair of compatible site-specific recombination sites.

As used herein the term "site-specific recombinase" refers to an enzyme that mediates site-specific recombination. Examples of site-specific recombinase include, without limitation, Cre recombinase and FLP recombinase. A "cognate" site-specific recombinase refers to a recombinase that can recognize and effectuate recombination between a pair of compatible sequence-specific recombination sites. For example, bacteriophage P1 Cre recombinase recognizes lox recombination sites whereas yeast FLP recombinase recognizes FRT recombination sites.

As used herein, the term "Cre recombinase" refers to a protein that is able to mediate site-specific recombinase activity of the Cre protein of bacteriophage P1 (Hamilton, D. L., et al., J. Mol. Biol. 178:481-486 (1984), which is incorporated by reference herein in its entirety). The Cre protein of bacteriophage P1 mediates site-specific recombination between specialized recombination sequences, known as "loxP" sequences. See, e.g., Hoess et al., Proc. Natl. Acad. Sci. USA 79:3398-3402 (1982) and Sauer, B. L., U.S. Pat. No. 4,959,317, which are incorporated by reference herein in their entireties. The term encompasses any derivatives of a naturally occurring Cre recombinase that retain the ability to effectuate recombination between two compatible lox sites.

Recombination products are dependent on the location and relative orientation of the lox sites. When two lox sequences having an identical orientation exist within the same DNA molecule, a DNA sequence flanked by the two lox sequences is excised by the Cre recombinase to form a circular molecule (excision reaction). Conversely, when two lox sequences exist in different DNA molecules, one of which is a circular DNA, the circular DNA is inserted into the other DNA molecule via the lox sequences (insertion reaction). In another embodiment, the Cre recombinase can be an optimized Cre recombinase. See, for example, International Patent Application Publication No. WO 2014158593, which is incorporated by reference herein in its entirety. In one embodiment, the Tat-Cre recombinase includes a nuclear localization signal.

As used herein, the term "FLP recombinase" refers to a protein having the site-specific recombinase activity of yeast FLP (*Saccharomyces cerevisiae*). The FLP protein encoded by yeast 2 μ DNA mediates site-specific recombination between a pair of compatible FRT recombination sites. See, for example, Babineau et al., J. Biol. Chem., 260, 12313-12319 (1985), which is incorporated by reference herein in its entirety. The term encompasses any derivatives of a naturally occurring FLP recombinase that retain the ability to effectuate recombination between two compatible FRT sites. Recombination products are dependent on the location and relative orientation of the FRT sites. When two FRT sequences having an identical orientation exist within the same DNA molecule, a DNA sequence flanked by the two FRT sequences is excised by the FLP recombinase to form a circular molecule (excision reaction). Conversely, when two FRT sequences exist in different DNA molecules, one of which is a circular DNA, the circular DNA is inserted into the other DNA molecule via the FRT sequences (insertion reaction). In one embodiment, the FLP recombinase can be an optimized FLP recombinase. See, for example, U.S. Patent Application Publication No. 2010/0050279, which is incorporated by reference herein in its entirety.

In one embodiment, the term "site-specific recombinase" refers to a Cre:FLP fusion protein that is able to recombine pair of compatible FRT or lox recombination sites. See, for example, Djukanovic et al. Plant Biotechnol J. 2008 October; 6(8):770-81, which is incorporated by reference herein in its entirety.

As used herein, the term "recombinase fusion protein comprising a protein transduction domain" refers to a fusion protein comprising a site-specific DNA recombinase domain (such as Cre or FLP), a protein transduction domain (e.g., derived from TAT, VP22, FGF or Antp) and a nuclear localization domain. See, for example, International Patent Application Publication No. WO 2003076561, which is incorporated by reference herein in its entirety. In one embodiment, the recombinase fusion protein is a "TAT-Cre" fusion protein comprising a Cre DNA recombinase domain fused to the basic membrane translocation peptide of HIV Tat protein, or cell penetrating fragments thereof. Recombinant TAT-Cre protein is commercially available, e.g. from Excellgen (Cat. No.: EG-1001) or EMD-Millipore (Cat. No.: SCR508).

As used herein, the term "lox site" refers to any art-recognized lox recombination site, or variant thereof, which includes the 34 base pair loxP site in bacteriophage P1 as well as a number of variant lox sites including, but not limited to, Lox 511, Lox 5171, Lox 2272, M2, M3, M7, M11, Lox71 and Lox66 (Missirlis et al. BMC Genomics 7: 73. 1471-2164, which is incorporated by reference herein in its entirety). Examples of non-cross-reactive compatible pairs of mutant lox sites are disclosed in U.S. Pat. Nos. 7,696,335; 7,060,499 and 7,696,335, which are incorporated herein by reference in their entireties.

As used herein, the term "FRT site" refers to any art-recognized yeast FRT recombination site, or variant thereof, which includes a 34 base pair FRT site, in which a spacer region of 8 base pairs is flanked by two inverted repeats of 13 base pairs. See, for example, Jayaram et al., Proc. Natl. Acad. Sci. 82, 5875-5879 (1985); Umlauf S. W. et al., EMBO Journal, 7, 1845-1852 (1988); Lee J. et al., EMBO Journal, 18, 784-791, 1999, which are incorporated by reference herein in their entireties. Examples of non-cross-reactive compatible pairs of mutant FRT sites are disclosed, for example, in U.S. Pat. Nos. 7,476,539 and 7,736,897, which are incorporated herein by reference in their entireties.

As used herein, the term "transduction" or "transduced" refers to introduction of a polynucleotide into a host cell genome using a retrovirus.

As used herein, the term "stably expressing" refers to expression of a gene from a polynucleotide introduced into a host cell genome.

As used herein, the term "promoter" refers to a regulatory region of DNA that is in operable linkage with a nucleotide sequence, e.g., a protein coding sequence. The promoter contains specific DNA sequences and response elements that are recognized by proteins known as transcription factors. These factors bind to and recruit RNA polymerase II to the promoter thereby facilitating transcription of the downstream nucleotide sequence. The transcribed mRNA comprising a protein coding sequence is then translated to produce the expressed protein.

As used herein, the term "operable linkage" refers to the configuration between a promoter sequence and a protein coding region that allows for the transcription of the protein coding region in a host cell.

As used herein, the term "regulatable" means that the transcription of a protein coding region can be activated in a negative manner, or "down-regulated"; or in a positive manner, or "up-regulated". In one embodiment, the expression of a protein coding sequence can be regulated by an inducible promoter. In another embodiment, the surface expression of a protein coding sequence can be down regulated by site-specific recombination after excision of at least a portion of the protein coding sequence.

As used herein, the term "mutagenizing conditions" refers to conditions that result in the genetic alteration of a polynucleotide (e.g., a polynucleotide encoding a TCR) in a cell. Non-limiting mutagenizing conditions include cells that have been engineered to express an activation-induced (cytidine) deaminase (AID) gene.

As used herein, the term "specifically binds to" refers to the ability of a TCR to bind to an antigen (e.g., a peptide-MHC complex) as such binding is understood by one skilled in the art. For example, a TCR that specifically binds to an antigen can bind to other antigens, generally with lower affinity as determined by, e.g., immunoassays, BIAcore®, or other assays known in the art (see, e.g., Savage et al., Immunity. 1999, 10(4):485-92, which is incorporated by reference herein in its entirety). In a specific embodiment, a TCR that specifically binds to an antigen binds to the antigen with an association constant ($K_a$) that is at least 2-fold, 5-fold, 10-fold, 50-fold, 100-fold, 500-fold, 1,000-fold, 5,000-fold, or 10,000-fold greater than the $K_a$ when the TCR binds to another antigen.

As used herein, the term "high affinity" refers to the ability of a TCR to bind to an antigen (e.g., a peptide-MHC complex) with an association constant ($K_a$) of at least $10^4$ $M^{-1}$, e.g., at least $10^5$ $M^{-1}$, at least $10^6$ $M^{-1}$, at least $10^7$ $M^{-1}$, at least $10^8$ $M^{-1}$, at least $10^9$ $M^{-1}$, at least $10^{10}$ $M^{-1}$, at least $10^{11}$ $M^{-1}$, or at least $10^{12}$ $M^{-1}$.

As used herein, the term "high selectivity" refers to a TCR that specifically binds to a desired antigen (e.g., a desired peptide-MHC complex) with an association constant (Ka) that is at least 5-fold, 10-fold, 50-fold, 100-fold, 500-fold, 1,000-fold, 5,000-fold, or 10,000-fold greater than the Ka when the TCR binds to another antigen (e.g., a peptide-MHC complex).

As used herein, the term "mimetic" refers to a molecule that biologically mimics the action or activity of some other molecule. An example of a mimetic molecule is a phosphomimetic molecule, which mimics the action or activity of a phosphorylated molecule; thus, a phosphopeptide mimetic is a peptide that mimics the action or activity of a phosphorylated peptide by, e.g., replacing a phosphorylated amino acid residue in the phosphorylated peptide with a phosphomimetic residue. Non-limiting examples of phosphomimetic groups or residues include O-boranophospho, borono, O-dithiophospho, phosphoramide, H-phosphonate, alkylphosphonate, phosphorothiolate, phosphodithiolate and phosphorofluoridate, any of which may be derivatized on Tyr, Thr, Ser, Arg, Lys, or His residues. In certain embodiments, an Asp or Glu residue is used as a phosphomimetic. The Asp or Glu residue can substitute for a phospho-Tyr, phospho-Thr, phospho-Ser, phospho-Arg, phospho-Lys and/or phospho-His residue in a peptide.

As used herein, a cell "does not express" endogenous TCR if the expression of the endogenous TCR in this cell is not detectable using art-recognized methods, e.g., RT-PCR or flow cytometry analysis. As used herein, a cell "does not express" endogenous CD4 or CD8 if the expression level of the endogenous CD4 or CD8 in this cell is not detectable using art-recognized methods, e.g., RT-PCR or flow cytometry analysis.

As used herein, the surface expression of a protein is "abrogated" if 85%, 86%, 87%, 88%, 89%, 90%, 91%, 92%, 93%, 94%, 95%, 96%, 97%, 98%, or 99% of the cells that previously expressed the protein on the cell surface no longer express the protein on the cell surface and/or if the surface expression level of the protein on a given cell is reduced by at least 85%, 86%, 87%, 88%, 89%, 90%, 91%, 92%, 93%, 94%, 95%, 96%, 97%, 98%, or 99%.

As used herein, the term "TCR diversity" of a TCR cellular library refers to the number of TCRs expressed on the cell surface that include distinct combinations of TCR α chain amino acid sequence and TCR β chain amino acid sequence.

In the following, preferred embodiments of a cell, cellular library and/or method of the invention are provided.

II. GENERATION OF HOST CELL LINES SUITABLE FOR TCR DISPLAY

1) Selection of a Host Cell Line for TCR Gene Library Expression and Cell Surface Display The TCR display technology disclosed herein employs a host cell line that provides a suitable environment for the expression and proper assembly of functional T cell receptors on the host cell surface. In addition, e.g., to high transduction efficiency and rapid doubling time, it is advantageous for the selected host cell line to faithfully reproduce protein trafficking to cellular compartments where post-translational modification (e.g., glycosylation, palmitoylation, and/or phosphorylation) occurs and where the interaction with chaperone proteins ensures proper folding of the nascent polypeptides. Accessory membrane proteins then facilitate membrane deposition where CD3 stabilizes the assembly of the expressed TCR on the cell surface. In addition, the peptide-MHC complex recognition and signaling activity of the assembled TCR protein is dependent on co-receptors, surface expressed CD3 as well as adhesion and accessory proteins, for example, CD2 and LFA-1.

In one embodiment, the host cell is a vertebrate cell, preferably from a mammal, including but not limited to, a mouse or human. In another embodiment, the host cell is derived from a lymphocyte, for example a cell of the T or B lymphocyte lineage. In one embodiment, the host cell can be derived from a T cell progenitor, a developing T cell or a mature T lymphocyte.

In one embodiment, the host cell of the T cell lineage is isolated from fetal liver, embryonic thymus, adult thymus or a thymoma. A T lymphocyte can also be derived from T cells resulting from the differentiation of a pluripotent stem cell, including but not limited to, embryonic stem cells, induced pluripotent stem (iPS) cells, adult stem cells or $CD34^+$ hematopoietic stem cells.

In another embodiment, the host cell can originate from a T lymphocyte of a genetically engineered animal, such as a knockout mouse in which the disruption of a regulatory gene leads to the accumulation of T cell progenitors that are blocked at a defined stage of T cell development (Bradley et al. Mamm. Genome 2012 October; 23(9-10):580-6, which is incorporated by reference herein in its entirety). Examples of mutant mice with arrested T cell development include, but are not limited to, SCID mice as well as null mutations of GATA3, RAG1, RAG2, ku80, TCR β, CD3epsilon, Lck/Fyn double knockout, ZAP-70/Syk double knockout, LAT, SLP-76, GADS, VAV1/2/3 triple knock out, TCRα, CD3δ, RAG1/RAG2 double knockout or ZAP-70 (Miosge and Goodnow, *Immunology and Cell Biology* (2005) 83, 318-335, which is incorporated by reference herein in its entirety).

In one embodiment, a host cell can be, e.g., a $CD8^+$ cytotoxic T cell, a $CD8^+$ regulatory T cell, a $CD4^+$ cytotoxic T cell, a $CD4^+$ helper T (including $T_H1$, $T_H2$, $T_H3$, $T_H17$, Th9, or $T_{FH}$ subtypes), a $CD4^+$ regulatory T cell, or an invariant NKT (iNKT) cell. In other embodiments, a host cell can be a B cell or an NK cell.

The host cells listed above that are primary cells can be immortalized into cell lines by retroviral transfection with Telomerase Reverse Transcriptase (Barsov, E. V., Methods Mol Biol. 2009; 511:143-58, which is incorporated by reference herein in its entirety) as well as other techniques that are well known in the art (see, for example, published U.S. Patent Application Nos. 2005/0123521, 2010/0279401 and International PCT application PCT/US1989/001526, or Robek, M. D. and Ratner, L., Virology, 1999, 73: 4856-4865, each of which is incorporated by reference herein in its entirety). Immortalized host cell lines that retain the requisite properties summarized above are then selected based on doubling time, retroviral transduction efficiency and the amount of IL-2 secretion or reporter activity after TCR activation, as disclosed herein.

In one embodiment, the host cell can be derived from murine pre-B 1624-5 cell lines that possess the intracellular components needed to assemble and express T cell receptors (see, for example, U.S. Pat. No. 8,748,353, which is incorporated herein by reference in its entirety).

In another embodiment, the host cell can be derived from the DO-11.10.7 mouse T cell hybridoma, 58 alpha–beta– (58–/–), which does not express functional T cell receptor alpha/beta chains on the cell surface, but does express CD3 on its cell surface (see, e.g., Letourneur and Malissen Eur J Immunol. 1989; 19(12):2269-74, which is incorporated herein by reference in its entirety).

In another embodiment, the host cell can be derived from the murine thymoma cell line Bw5147 that does not express functional T cell receptor alpha/beta chains.

2) Genetic Disruption of Endogenous Gene Expression in the Host Cell Line

Depending on the particular experimental design of the TCR cellular library screen, the expression of one or more endogenous host cell genes involved in TCR activity and antigen-MHC recognition is abolished to avoid interference with a transduced T cell receptor library and/or co-receptors (e.g., CD4 and/or CD8).

Gene silencing in the host cell can be achieved using a number of methods that are well known in the art.

For example, mutant host cell lines that no longer express a cell surface marker on the cell surface can be generated by somatic cell mutagenesis, using, for example, a chemical mutagen, gamma irradiation (e.g., the 58 α–/β– cell line described in Letourneur and Malissen Eur J Immunol. 1989; 19(12):2269-74, which is incorporated by reference herein in its entirety) or transposon-mediated insertional mutagenesis (described, for example, in U.S. Pat. Nos. 8,592,211 and 7,767,454, which are incorporated by reference herein in their entireties). The resulting mutant host cell lines can then be screened for defects in the expression of cell surface markers by FACS selection.

The expression of a targeted endogenous gene can also be abolished by conventional knockout via locus-specific homologous recombination (see, for example, U.S. Pat. No. 5,530,178 (CD8 knockout mouse) or U.S. Pat. No. 5,698,765 (CD4 knockout mouse), which are incorporated by reference herein in their entireties).

In addition, the expression of any selected endogenous target gene can be disrupted using a number of genome editing technologies, including, but not limited to, designer zinc fingers (described, for example, in U.S. Pat. No. 8,106,255 (general methodology) and U.S. Pat. No. 8,956,828 (targeted disruption of T cell receptor genes using engineered zinc finger protein nuclease, which are incorporated by reference herein in their entireties), transcription activator-like effector nucleases (TALENs; described, for example, in U.S. Pat. No. 8,614,092, which is incorporated by reference herein in its entirety), homing meganucleases (described, for example, in U.S. Pat. No. 7,842,489, which is incorporated by reference herein in its entirety) or CRISPR/cas genome editing systems (described, for example, in U.S. Pat. No. 8,697,359, which is incorporated by reference herein in its entirety).

In one embodiment, endogenous host cell gene expression can also be abolished using site-directed recombination technology, including, but not limited to, a Cre recombinase (described for example in U.S. Pat. No. 4,959,317, which is incorporated by reference herein in its entirety) or FLP recombinase (described, for example, in U.S. Pat. No. 5,885,836, which is incorporated by reference herein in its entirety).

In another embodiment, host cell expression of a targeted gene can be silenced by RNA interference (RNAi; described, for example, in U.S. Pat. No. 8,329,463, which is incorporated by reference herein in its entirety). For example, sequence-specific small-hairpin RNAs (shRNAs) have been shown to inhibit endogenous TCR genes and/or co-receptors (e.g., TCR-α and TCR-β, see for example, U.S. Patent Application Publication No. 2012/0321667, which is incorporated by reference herein in its entirety). By blocking expression of one or more of these proteins, the T cell is no longer able to produce one or more of the key components of the TCR complex, thereby destabilizing the TCR complex and preventing cell surface expression of a functional TCR.

In one embodiment, any one of the above-referenced methodologies is implemented to generate a T lymphocyte derived host cell line that does not express endogenous TCR on its cell surface.

In an embodiment, a T lymphocyte derived host cell line does not express endogenous TCR (i.e., TCRα and TCRβ) or endogenous CD4 on its cell surface (referred to herein as TCRα$^-$/β$^-$ CD4$^-$ host cell).

In another embodiment, a mouse T lymphocyte derived host cell line does not express mouse TCR (i.e., mTCRα and mTCRβ) or mouse CD4 on its cell surface (referred to herein as mTCRα$^-$/β$^-$ mCD4$^-$ host cell).

In another embodiment, a T lymphocyte derived host cell line does not express endogenous TCR (i.e., TCRα and TCRβ) or endogenous CD8 (e.g., CD8α and CD8β) on its cell surface (referred to herein as TCRα$^-$/β$^-$ CD8$^-$ host cell).

In another embodiment, a mouse T lymphocyte derived host cell line does not express mouse TCR (i.e., mTCRα and mTCRβ) or mouse CD8 (e.g., mCD8α and mCD8β) on its cell surface (referred to herein as mTCRα$^-$/β$^-$ mCD8$^-$ host cell).

In another embodiment, a T lymphocyte derived host cell line does not express endogenous TCR (i.e., TCRα and TCRβ) or endogenous MHC I on its cell surface (referred to herein as TCRα$^-$/β$^-$ MHC I$^-$ host cell).

In another embodiment, a mouse T lymphocyte derived host cell line does not express mouse TCR (i.e., mTCRα and mTCRβ) or mouse MHC I on its cell surface (referred to herein as mTCRα$^-$/β$^-$ mMHC I$^-$ host cell).

In another embodiment, a T lymphocyte derived host cell line does not express endogenous TCR (i.e., TCRα and TCRβ) or endogenous MHC II on its cell surface (referred to herein as TCRα$^-$/β$^-$ MHC II$^-$ host cell).

In another embodiment, a mouse T lymphocyte derived host cell line does not express mouse TCR (i.e., mTCRα and mTCRβ) or mouse MHC II on its cell surface (referred to herein as mTCRα$^-$/β$^-$ mMHC II$^-$ host cell).

3) Generation of a Host Cell Line Expressing a Recombinant T Cell Co-Receptor

The transmembrane glycoproteins CD8 and CD4 are characteristic of distinct populations of T lymphocytes whose antigen responses are restricted by Major Histocompatibility Complex class I and II proteins (MHC, also referred to as HLA in man), respectively. CD4 is expressed on the cell surface as a monomer whereas CD8 is expressed as a dimer. CD4 and CD8 act as co-receptors of the T cell receptor by binding to their cognate MHC, thereby facilitating the engagement of the T cell receptor with the MHC bound antigen peptide. CD4$^+$ T cells respond to antigen in association with MHC class II molecules, and CD8$^+$ T cells respond to antigen in association with MHC class I molecules. Studies in vitro (Laugel et al., J. Biol. Chem. 2007; 282(33):23799-810, which is incorporated by reference herein in its entirety) indicate that the CD8 co-receptor substantially enhances binding efficiency at suboptimal TCR/peptide-MHC I affinities through effects on both association and dissociation rates. The trimolecular interactions among TCR, peptide-MHC I, and CD8 has also been shown to be cooperative (Jiang et al., Immunity. 2011; 34(1): 13-23). The extent of co-receptor dependence was therefore found to be inversely correlated to TCR/peptide-MHC I affinity.

To evaluate the affinity of a T cell receptor for a peptide-MHC complex during a TCR cellular library screen, a TCRα$^-$/β$^-$ CD4$^-$ or CD8 negative CD3$^+$ host cell can be engineered to express a recombinant CD4 or CD8 co-receptor.

In an embodiment, a TCRα$^-$/β$^-$ CD4$^-$ CD3$^+$ host cell can be engineered to express a recombinant CD4 (e.g., Human CD4: UniProtKB-P01730; Mouse CD4: UniProtKB-P06332).

In another embodiment, a TCRα$^-$/β$^-$ CD4$^-$ CD3$^+$ host cell can be engineered to express a recombinant chimeric CD4.

In another embodiment, a human TCRα$^-$/β$^-$ CD4$^-$ CD3$^+$ host cell can be engineered to express the extracellular region of a recombinant mouse CD4 protein (e.g., residues 27-394 of UniProtKB-P06332).

In another embodiment, a mouse TCRα$^-$/β$^-$ CD4$^-$ CD3$^+$ host cell can be engineered to express the extracellular region of a recombinant human CD4 protein (e.g., residues 26-396 of UniProtKB-P01730).

In another embodiment, a human TCRα$^-$/β$^-$ CD4$^-$ CD3$^+$ host cell can be engineered to express a recombinant chimeric CD4 protein having the extracellular region of mouse CD4 polypeptide fused in frame with human CD4 transmembrane and cytoplasmic regions.

In another embodiment, a non-human TCRα$^-$/β$^-$ CD4$^-$ CD3$^+$ host cell can be engineered to express a recombinant chimeric CD4 protein having the extracellular region of the human CD4 polypeptide fused in frame with a non-human CD4 transmembrane and cytoplasmic regions.

In another embodiment, a mouse TCRα$^-$/β$^-$ CD4$^-$ CD3$^+$ host cell can be engineered to express a recombinant chimeric CD4 protein having the extracellular region of the human CD4 polypeptide fused in frame with mouse CD4 transmembrane and cytoplasmic regions.

The amino acid sequences encoding the human extracellular regions of the chimeric human/mouse CD4 can be at least 90% identical, optionally 91, 92, 93, 94, 95, 96, 97, 98, 99 or 100% identical, to the corresponding amino acid sequences of a wild type human CD4.

The amino acid sequences encoding the mouse transmembrane region and the cytoplasmic region of the chimeric human/mouse CD4 can be at least 90% identical, optionally 91, 92, 93, 94, 95, 96, 97, 98, 99 or 100% identical, to the corresponding amino acid sequences of a wild type mouse CD4.

In another embodiment, a TCRα−/β− CD8− CD3+ host cell can be engineered to express recombinant CD8α and CD8β.

Exemplary mouse CD8α and CD8β amino acid sequences are listed below.

```
Mouse CD8α polypeptide isoform 1(UniProtKB:
P01731-1):
                              (SEQ ID NO.: 21)
KPQAPELRIFPKKMDAELGQKVDLVCEVLGSVSQGCSWLFQNSSSKLPQP

TFVVYMASSHNKITWDEKLNSSKLFSAMRDTNNKYVLTLNKFSKENEGYY

FCSVISNSVMYFSSVVPVLQKVNSTTTKPVLRTPSPVHPTGTSQPQRPED

CRPRGSVKGTGLDFACDIYIWAPLAGICVALLLSLIITLICYHRSRKRVC

KCPRPLVRQEGKPRPSEKIV (bold: extracellular region; normal: transmem-
brane; italic: cytoplasmic region)

Mouse CD8β polypeptide (UniProtKB: P10300):
                              (SEQ ID NO.: 22)
LIQTPSSLLVQTNHTAKMSCEVKSISKLTSIYWLRERQDPKDKYFEFLAS

WSSSKGVLYGESVDKKRNIILESSDSRRPFLSIMNVKPEDSDFYFCATVG

SPKMVFGTGTKLTVVDVLPTTAPTKKTTLKMKKKQCPFPHPETQKGLTC

SLTTLSLLVVCILLLLAFLGVAVYFYCVRRRARIHFMKQFHK (bold: extracellular region; normal: transmem-
brane; italic: cytoplasmic region)
```

Exemplary human CD8α and CD8β amino acid sequences are listed below:

```
Human CD8α polypeptide isoform 1 (UniProtKB:
P01732-1):
                              (SEQ ID NO.: 23)
SQFRVSPLDRTWNLGETVELKCQVLLSNPTSGCSWLFQPRGAAASPTFLL

YLSQNKPKAAEGLDTQRFSGKRLGDTFVLTLSDFRRENEGYYFCSALSNS

IMYFSHFVPVFLPAKPTTTPAPRPPTPAPTIASQPLSLRPEACRPAAGGA

VHTRGLDFACDIYIWAPLAGTCGVLLLSLVITLYCNHRNRRRVCKCPRPV

VKSGDKPSLSARYV (bold: extracellular region; normal: transmem-
brane; italic: cytoplasmic region)

Human CD8β polypeptide isoform 1 (UniProtKB:
P10966-1):
                              (SEQ ID NO.: 24)
LQQTPAYIKVQTNKMVMLSCEAKISLSNMRIYWLRQRQAPSSDSHHEFLA

LWDSAKGTIHGEEVEQEKIAVFRDASRFILNLTSVKPEDSGIYFCMIVGS

PELTFGKGTQLSVVDFLPTTAQPTKKSTLKKRVCRLPRPETQKGPLCSPI

TLGLLVAGVLVLLVSLGVAIHLCCRRRRARLRFMKQFYK (bold: extracellular region; normal: transmem-
brane; italic: cytoplasmic region)
```

In another embodiment, a TCRα−/β− CD8− CD3+ host cell can be engineered to express recombinant human/mouse chimeric CD8α and human/mouse chimeric CD8β (chiCD8αβ+).

In another embodiment, a human TCRα−/β− CD8− CD3+ host cell can be engineered to express a recombinant chimeric CD8 protein having the extracellular region of mouse CD8α and mouse CD8β.

In another embodiment, a mouse TCRα−/β− CD8− CD3+ host cell can be engineered to express a recombinant chimeric CD8 protein having the extracellular region of human CD8α and human CD8β.

In other examples, recombinant chimeric human/mouse CD8α and human/mouse CD8β polypeptides can be engineered where a human CD8α extracellular region is fused in frame with a mouse CD8α transmembrane and cytoplasmic regions and a human CD8β extracellular region is fused in frame with a mouse CD8β transmembrane and cytoplasmic regions.

The amino acid sequences encoding the human extracellular regions of the chimeric human/mouse CD8α and human/mouse CD8β polypeptides can be at least 90% identical, optionally 91, 92, 93, 94, 95, 96, 97, 98, 99 or 100% identical, to the corresponding amino acid sequences of a wild type human CD8α and CD8β, respectively.

The amino acid sequences encoding the mouse transmembrane region and the cytoplasmic region of the chimeric human/mouse CD8α and human/mouse CD8β polypeptides can be at least 90% identical, optionally 91, 92, 93, 94, 95, 96, 97, 98, 99 or 100% identical, to the corresponding amino acid sequences of a wild type mouse CD8α and CD8β, respectively.

Identity of related polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds. Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., SIAM J. Applied Math, 48:1073 (1988), all the contents of which are incorporated by reference herein in their entireties. Methods of determining the relatedness or percent identity of two polypeptides are designed to give the largest match between the sequences tested. Preferred computer program methods to determine identity between two sequences include, but are not limited to, the GCG program package, including GAP (Devereux et al., Nucl. Acid. Res., 12:387 (1984), which is incorporated by reference herein in its entirety; Genetics Computer Group, University of Wisconsin, Madison, Wis., BLASTP, BLASTN, and FASTA (Altschul et al., J. Mol. Biol., 215: 403-410 (1990), which is incorporated by reference herein in its entirety). The BLASTX program is publicly available from the National Center for Biotechnology Information (NCBI) and other sources (BLAST Manual, Altschul et al. NCB/NLM/NIH Bethesda, Md. 20894; Altschul et al., supra (1990)). The well-known Smith Waterman algorithm may also be used to determine identity.

In one embodiment, the chimeric CD8α and CD8β comprise the amino acid sequences of SEQ ID NOs.: 1 and 2, respectively.

For expression in a TCRα−/β− CD8− CD3+ host cell, the selected CD8α and CD8β coding regions can be cloned downstream of a suitable promoter in an expression cassette, e.g., a retroviral or lentiviral expression cassette.

For expression in a TCRα−/β− CD4− CD3+ host cell, the selected CD4 coding region can be cloned downstream of a suitable promoter in an expression cassette, e.g., a retroviral or lentiviral expression cassette.

The promoter can be a constitutive or regulatable promoter depending on the design of the TCR cellular library screen.

Exemplary embodiments of constitutive promoters include, but are not limited to, viral promoters from polyoma, adenovirus, cytomegalovirus (CMV) and simian virus 40 (SV40). In an exemplary configuration, the protein coding sequences are flanked upstream (i.e., 5') by the human cytomegalovirus IE promoter and downstream (i.e., 3') by an SV40 poly(A) signal. The human cytomegalovirus IE promoter is described in Boshart et al. (1985) Cell 41:521 530, which is incorporated by reference herein in its entirety. Other ubiquitously expressing promoters which can be used include the HSV-TK promoter, β-actin promoters and the EF-1α promoter. In certain embodiments, the constitutive promoter can be T cell-specific, e.g., a CD3δ T cell-specific promoter.

Suitable regulatable expression systems should have, e.g., the following properties: a low level of basal expression in the non-induced state; inducers that do not promote pleiotropic effects; high levels of expression in the induced state; highly specific induction of expression of a candidate nucleic acid of interest; and modulation of the level of induced expression. Examples of regulatable expression systems having such properties include, but are not limited to: a Tet inducible system (see, e.g., Gossen et al. (1992) Proc. Natl. Acad. Sci. USA 89:5547 5551; Gossen et al. (1995) Science 268:1766 1769, which are incorporated by reference herein in their entireties); a FK506/rapamycin inducible system (see, e.g., Spencer et al. (1993) Science 262:1019 1024; Belshaw et al. (1996) Proc. Natl. Acad. Sci. USA 93:4604 4607, which are incorporated by reference herein in their entireties); a RU486/mifepristone inducible system (Wang et al. Proceedings of the National Academy of Sciences (1994) 91(17):8180-4, which is incorporated by reference herein in its entirety); a cumate inducible system (Mullick et al. BMC Biotechnol. 2006 Nov. 3; 6:43, which is incorporated by reference herein in its entirety) or an ecdysone inducible system (for review, see Rossi et al. (1989) Curr. Op. Biotech. 9:451 456, which is incorporated by reference herein in its entirety). Many constitutive, tissue-specific and inducible promoters are now commercially available from vendors such as Origene, Promega, Invitrogen, System Biosciences and Invivogen.

In certain embodiments, CD8α and CD8β are cloned into separate expression vectors.

In other embodiments, the expression of CD8α and CD8β can be linked on the same retroviral expression construct. This can be accomplished by, for example, expressing CD8α and CD8β, or fragments thereof, from one promoter and separating the coding regions for CD8α and CD8β, or fragments thereof, by an IRES element.

Alternatively, co-expression of the two chains of CD8 can be achieved by cloning two separate expression cassettes into a single retroviral backbone, such that the expression of each individual binding protein chain is separately controlled.

In another embodiment, CD8α and CD8β chains can be expressed from the same vector by the use of bi-directional promoters that confer transcriptional activities in opposite directions. This option has the advantage that promoter interference does not occur, which may negatively affect expression levels of promoters in close proximity.

Depending on the screening strategy, a co-receptor expression cassette can be designed to include site-specific recombination sequences flanking the co-receptor's coding region or a portion of the coding region. Thus, upon integration of the transduced co-receptor expression cassette into the TCR negative, co-receptor negative host cell, the nucleotide sequence located between two site-specific recombination sites can be excised by expressing the corresponding site-specific recombinase in the host cell.

In another embodiment, the co-receptor expression cassette comprises an intervening DNA sequence flanked by site-specific recombination sequences that are inserted to disrupt translation of the co-receptor's coding region. Co-receptor gene translation can then be restored by site-specific recombinase-mediated excision of the intervening DNA sequence located between the site-specific recombination sequences.

Exemplary site-specific recombination systems that may be used in the present invention include, but are not limited to, the CRE-LOX or FLP/FRT systems (reviewed in Ann. Rev. Biochem. (2006) 75: 567-605 and Gaj et al. Biotechnol Bioeng. 2014 January; 111(1): 1-15, which are incorporated herein by reference in their entireties).

Expression of the appropriate site-specific recombinase can be driven by a constitutive, T cell-specific or inducible promoter, as described above.

In other embodiments, a site-specific recombinase can be delivered to a TCRα$^-$/β$^-$ host cell as a fusion protein, e.g., a Tat-Cre fusion protein (Joshi et al. Genesis (2002) 33:48-54; Peitz et al., (2002) Proc. Natl. Acad. Sci. USA 99:4489-94, the contents of which are incorporated by reference herein in their entireties). A TAT-Cre has been shown to induce greater than 95% recombination efficiency in fibroblasts and murine embryonic stem cells in vitro.

In another embodiment, a Cre recombinase can be linked to the ligand-binding domain of an estrogen receptor (see, e.g., Feil et al., (1996) PNAS 93:10887-10890, which is incorporated herein by reference in its entirety). This allows for the nuclear translocation of Cre in response to treatment of cells with tamoxifen.

In another embodiment, a TCRα$^-$/β$^-$ mCD8$^-$ CD3$^+$ host cell is transduced with a co-receptor expression cassette that contains lox recombination sites flanking the mouse transmembrane and cytoplasmic regions of the chimeric human/mouse CD8α coding region and human/mouse CD8β coding regions (chiCD8αβ$^+$/flox$^+$).

In another embodiment, a TCRα$^-$/β$^-$ mCD4$^-$ CD3$^+$ host cell is transduced with a co-receptor expression cassette that contains lox recombination sites flanking the mouse transmembrane and cytoplasmic regions of the chimeric human/mouse CD4 coding region (chiCD4$^+$/flox$^+$). 4) Generation of a derivative host cell line having one or more reporter constructs for the measurement of antigen-MHC specific TCR signaling The T cell receptor complex is a multi-subunit assembly comprising a variable TCRαβ or TCRγδ heterodimer and non-variable signal transduction subunits that contain immunoreceptor tyrosine based activation motifs (ITAMs) within their cytoplasmic regions (e.g., CD3). TCR engagement by a peptide-MHC complex triggers the association of Lck, a Src type tyrosine kinase, with a CD4 or CD8 co-receptor and the phosphorylation of two Tyr within each ITAM motif of the intracellular region of CD3. ZAP70, a Syk type tyrosine kinase, then associates with the ITAM motifs activated by Lck. Thereafter, the signal is transmitted to serine/threonine protein phosphatases (for example, by calcium signaling via calmodulin-calcineurin), serine/threonine protein kinases (for example, PKC, MAPK super family) and the like via various adaptor proteins (for example, LAT and SLP-76). These events ultimately lead to the activation of three key transcription factors: NFκB, NFAT and AP-1, each of which play a pivotal role in the induction of early cytokine production (e.g., interleukins (such as IL-2, -4, -6, and -17), TNF-α, and IFN-γ), which is required for clonal expansion of the activated T lymphocyte.

By incorporating a peptide/MHC-TCR responsive reporter construct into a host cell, the interaction between a recombinantly expressed TCR and/or co-receptor with a peptide-MHC complex and the subsequently induced T cell signaling activity can be determined in real-time from a reporter readout.

Reporter proteins providing readout of signaling activity are well known in the art and include, but are not limited to, cell-surface markers and bioluminescent (luciferase) or fluorescent proteins (e.g., green fluorescent protein (GFP), enhanced green fluorescent protein (EGFP), yellow fluorescent protein (YFP), blue fluorescent protein (BFP) and red fluorescent protein (RFP), recently reviewed by Senutovitch et al. Exp. Biol. Med. (2015); 240(6): 795-808, which is incorporated by reference herein in its entirety).

In certain embodiments, each of the signaling events induced by TCR activation can be individually monitored using promoters having appropriate transcription response elements (TREs), for example, NFκB/Rel, NFAT or AP-1. An array of signal transduction pathway GFP or luciferase reporters are now commercially available from, e.g., Sambio Sciences/Qiagen, Addgene and Invitrogen. Individual TREs, or combinations thereof, can be expressed in host cells.

III. GENERATION OF A CELLULAR TCR DISPLAY LIBRARY

In order to provide a source of DNA containing TCR α variable region Vα and Jα genes, and TCR β variable region Vβ, Jβ and Dβ genes, poly A$^+$ RNA is prepared from, for example, human fetal thymus, cord blood, tumor infiltrating lymphocytes (from a patient), a vaccinated patient, such as one vaccinated for human papillomavirus (HPV), Epstein-Barr virus (EBV), or for a cancer, or a HLA-A2 transgenic mouse vaccinated with an antigen of interest.

cDNAs encoding TCR β chains can be generated from mRNA isolated, for example, from pre-T lymphocytes having completed V β and DJ β rearrangement. These T lymphocytes can be CD44$^{low}$ CD25$^+$ DN3 or DN4 CD44$^-$ CD25$^-$ T lymphocytes.

cDNAs encoding TCR α chains can be generated, for example, from mRNA isolated from immature double positive T lymphocytes having completed Vα and Jα rearrangement. These lymphocytes can be CD4$^+$ CD8$^+$ CD3$^{low}$ T lymphocytes.

cDNA is prepared and used as a template for polymerase chain reaction (PCR)-based amplification of the TCR variable regions. The isolated PCR products comprising the TCR α and TCR β variable region open reading frames (ORFs) are then cloned into expression systems that allow the gene product of the various variable region genes to be expressed in a functional form on the cell surface of a host cell that does not express endogenous TCR on the cell surface.

For the expression of TCRs encoded by separate expression constructs, it is preferable that expression of different polypeptide chains are linked to different selection markers, thereby allowing separate selection for the expression of corresponding expression constructs.

Selection markers conferring resistance to antibiotics useful for the selection of the transduced or transfected host cells include, e.g., genes for puromycin, neomycin, hygromycin B, mycophenolic acid, histidinol, bleomycin, and phleomycin resistance. Cell surface proteins and fluorescent proteins are also suitable for use as selection markers.

In one embodiment, cDNA sequences encoding the variable regions of human TCR α or TCR β are amplified by PCR and cloned into a chimeric TCR α or TCR β expression vector backbone.

Specifically, a TCR α expression cassette contains a promoter, a human TCR signal sequence, a cloning site followed by a nucleotide sequence encoding mouse TCR α non-variable region. Nucleotide sequences encoding human TCR α variable regions are amplified out of the TCR α cDNA library by PCR and cloned into the cloning site of the TCR α expression cassette so as to be in frame with the mouse TCR α non-variable region. The resulting library is then transformed into E. coli. and plasmid DNA is introduced into host cells to generate a recombinant chimeric human/mouse TCR α library.

In a similar manner, a TCR β expression cassette contains a promoter, a human TCR signal sequence, a cloning site followed by a nucleotide sequence encoding mouse TCR β non-variable region. Nucleotide sequences encoding human TCR β variable regions are amplified out of the TCR β cDNA library by PCR and cloned into the cloning site of the TCR β expression cassette so as to be in frame with the mouse TCR β non-variable region. The resulting library is then transformed into E. coli. and plasmid DNA is introduced into host cells to generate a recombinant chimeric human/mouse TCR β library.

In one embodiment, cDNA sequences encoding the extracellular regions of human TCR α or TCR β are amplified by PCR and cloned into a chimeric TCR α or TCR β expression vector backbone.

Specifically, a TCR α expression cassette contains a promoter, a human TCR signal sequence, a cloning site followed by a nucleotide sequence encoding mouse TCR α transmembrane and cytoplasmic regions. Nucleotide sequences encoding human TCR α extracellular regions are amplified out of the TCR α cDNA library by PCR and cloned into the cloning site of the TCR α expression cassette so as to be in frame with the mouse TCR α transmembrane and cytoplasmic regions. The resulting library is then transformed into E. coli. and plasmid DNA is introduced into host cells to generate a recombinant chimeric human/mouse TCR α library.

In a similar manner, a TCR β expression cassette contains a promoter, a human TCR signal sequence, a cloning site followed by a nucleotide sequence encoding mouse TCR β transmembrane and cytoplasmic regions. Nucleotide sequences encoding human TCR β extracellular regions are amplified out of the TCR β cDNA library by PCR and cloned into the cloning site of the TCR β expression cassette so as to be in frame with the mouse TCR β transmembrane and cytoplasmic regions. The resulting library is then transformed into E. coli. and plasmid DNA is introduced into host cells to generate a recombinant chimeric human/mouse TCR β library.

In certain embodiments, the signaling region of a co-stimulatory molecule is fused to the C terminal end of a TCR α and/or TCR β cytoplasmic region. The co-stimulatory molecule can be selected from the group consisting of CD27, CD28, 4-1BB, OX40, CD30, CD40, ICOS, lymphocyte function-associated antigen-1 (LFA-1), CD2, CD7, LIGHT, NKG2C, NKG2D, B7-H3, a ligand that specifically binds with CD8β, TCR ζ chain or any combination thereof. T In one embodiment, a TCRα⁻/β⁻ CD8⁻ CD3⁺ chiCD8αβ⁺/flox⁺ TRE-GFP host cell line is transduced or transfected with the TCR α gene library followed by selection for stable transformants. Expression of TCR α in the transformants can be confirmed by RT-PCR analysis. The resulting clones are pooled and then transduced or transfected with the TCR β gene library followed by selection of the stable double transformants.

In other embodiments, a TCRα⁻/β⁻ CD8⁻ CD3⁺ chiCD8α3+/flox⁺ TRE-GFP host cell line is first transduced or transfected with the TCR β gene library followed by the TCR α gene library.

In another embodiment, a TCRα⁻/β⁻ CD4⁻ CD3⁺ chiCD4+/flox⁺ TRE-GFP host cell line is transduced or transfected with the TCR α gene library followed by selection for stable transformants. Expression of TCR α in the transformants can be confirmed by RT-PCR. The resulting clones are pooled and then transduced or transfected with the TCR β gene library followed by selection of the stable double transformants.

In other embodiments, a TCRα⁻/β⁻ CD4⁻ CD3⁺ chiCD4+/flox⁺ TRE-GFP host cell line is first transduced or transfected with the TCR β gene library followed by the TCR α gene library.

In certain embodiments, the TCR gene library is introduced into a host cell line by retroviral transduction. Retroviral transduction can be controlled to ensure that the majority of retrovirally transduced cells are genetically modified by only one recombinant retroviral construct, resulting in clonal expression of at least one TCR protein. In one embodiment, the retroviral transduction is controlled by exploiting multiplicity of infection (MOI). The MOI can be 10, 1, 0.5, 0.1 or less. In another embodiment, retroviral transduction is controlled to ensure that after transduction less than 5-6% of cells express the recombinant protein that is encoded by the retroviral expression vector.

The separate expression of TCR α and TCR β chains from different expression vectors offers the advantage that collections of expression vectors encoding a diverse collection of TCR α chains can randomly be combined with collections of expression vectors encoding a diverse collection of TCR β chains. This TCR α and TCR β chain shuffling can create a large degree of diversity of different binding specificities, even when the total number of TCR α and TCR β chain collections are limited (e.g., $10^4$ different TCR α chains, randomly combined with $10^4$ different TCR β chains, theoretically result in $10^8$ TCRs, each of which may have distinct specificities).

TCRα⁻/β⁻ CD8⁻ CD3⁺ chiCD8αβ⁺/flox⁺ TRE-GFP or TCRα⁻/β⁻ CD4⁻ CD3⁺ chiCD4⁺/flox⁺ TRE-GFP reporter host cells receiving recombinant complementary TCR α and TCR β chains express functional TCRs on the cell surface which can then be enriched by fluorescence-activated cell sorting (FACS) or magnetic activated cell sorting (MACS) to generate a highly diverse cellular TCR display library.

IV. SCREENING OF A CELLULAR TCR DISPLAY LIBRARY

Disclosed herein are methods for the isolation and identification of a T cell receptor (TCR) with a desired characteristic comprising transducing or transfecting host cells that do not express endogenous TCR with a library of expression constructs encoding different recombinant TCRs to generate a recombinant TCR cellular library in which cells express different recombinant TCRs on their cell surface, selecting cells within the cellular library for a desired characteristic in the presence of a desired peptide-MHC complex and isolating and identifying the expression construct encoding the recombinant TCR with the desired characteristic.

Examples of a desired characteristic include, but are not limited to, high selectivity for the desired peptide-MHC complex, high affinity for the desired peptide-MHC complex, and demonstration of a positive functional readout in the presence of the desired peptide-MHC complex.

1) Screening Cellular TCR Display Libraries in the Presence or Absence of Co-Receptor Cell Surface Expression Disclosed herein are methods for the isolation and identification of at least one nucleic acid encoding a T cell receptor (TCR) that specifically binds to a desired peptide-MHC complex in the presence and absence of the cell surface expression of a co-receptor, e.g., CD4 or CD8.

In one embodiment, mouse TCRα⁻/β⁻ co-receptor CD3⁺ host cells expressing a recombinant co-receptor are transduced or transfected with a gene library of recombinant TCR α and TCR β, as disclosed herein. Transformants having TCRα/β surface expression are then selected. Host cells expressing cell surface recombinant TCR proteins that bind to a desired peptide-MHC complex with the desired affinity or selectivity (herein referred to as co-receptor dependent binders) are enriched by FACS or MACS from the non-binding host cell population. Nucleotide sequences encoding TCRs that bind the desired peptide-MHC complex in the presence of the co-receptor with the desired affinity or selectivity can then be isolated by PCR and sequenced.

In certain embodiments, the polynucleotide encoding the recombinant co-receptor or a portion of the recombinant co-receptor is flanked by site-specific recombination sites. To identify host cell clones expressing high affinity TCR in the co-receptor dependent binder population, the recombinant co-receptor expression cassette is deleted using a cognate site-specific recombinase as disclosed herein and cells no longer expressing the recombinant co-receptor on their cell surface are enriched. This co-receptor negative cell population is then rescreened for cell surface recombinant TCR proteins that bind to a desired peptide-MHC complex (herein referred to as co-receptor independent binders). Nucleotide sequences encoding TCRs that bind the desired peptide-MHC complex in the absence of the co-receptor can then be isolated by PCR and sequenced. In certain embodiments, a co-receptor independent binder is able to specifically bind to a cognate ligand (e.g., a peptide-MHC complex) in the absence of the co-receptor and/or able to mediate signaling in the presence of a cognate ligand (e.g., a peptide-MHC complex) in the absence of the co-receptor.

In one embodiment, an activity of a recombinant co-receptor can be modulated. In one embodiment, the cell surface expression of the recombinant co-receptor can be regulated using an inducible promoter. In another embodiment, the cell surface expression of the recombinant co-receptor can be regulated using the Cre/loxP system. The TCR library can then be screened for binding to the desired peptide-MHC complex as a function of decreasing expression of the recombinant co-receptor as described above.

Any T cell antigen that can be associated with the MHC class I or II protein and presented to T cells may be used to screen a cellular TCR display library. The peptide antigen can be chemically synthesized or derived from a natural source. In one embodiment, the peptide antigen is derived from a tumor cell.

The methods and compositions disclosed herein are broadly applicable to the expression, screening and identification of TCRs that specifically bind to an antigen of interest. However, any (functional) fragment of a TCR with any naturally occurring or artificially engineered modification may be used. With regard to full-length TCRs, any kind of artificially engineered or designed modifications of TCR binding regions can be exploited, for example, those generated by site-, or region-directed mutagenesis, fusion of naturally occurring sequences from different TCRs, randomization of CDR sequences, DNA shuffling, and error-prone PCR.

a) CD8 Dependent TCR Activation

In one embodiment, the TCRα$^-$/β$^-$ CD8$^-$ CD3$^+$ chiCD8αβ$^+$/flox$^+$ TRE-GFP host cell library expressing recombinant TCRs is assayed for binding to any T cell epitope of interest in the context of various MHC class I alleles in the form of specific 9- to 11-mer peptides complexed to MHC tetramers, dimers, or other multimeric complexes either directly or indirectly fluorescently labeled.

In one embodiment, the cells bearing an appropriate TCR can be captured and enriched by FACS and the α and β chains recovered and characterized.

In other embodiments, peptide-MHC class I engagement by the cell surface expression of an individual TCR can be determined by the expression of activation marker (e.g., CD69 or CD137), triggering of signaling pathway (e.g., NFAT signaling, IL-2 signaling, activator protein-1 signaling, or NFκB/Rel signaling), production of cytokine (e.g., IL-2, TNF-α, or IFN-γ), calcium flux, cell proliferation (e.g., proliferation of T cells), and activation of reporter system (e.g., IL-2-EGFP reporter system).

As a co-receptor, CD8 can also bind to the α3 domain of the same MHC class I molecules as the TCR to facilitate TCR signaling. Mutagenesis data indicate that residues 223-229 of the human MHC class I α chain are essential for CD8-MHC class I interaction (Salter et al. Nature 345:41-46 1990).

The role of the CD8-α3 interaction in T cell engagement of a desired peptide-MHC class I complex can be investigated using the TCR cellular library screen disclosed herein.

In one embodiment, a mouse TCRα$^-$/β$^-$ CD8$^+$ CD3$^+$ TRE-GFP host cell library expressing recombinant TCRs can be contacted with a desired peptide-human/mouse chimeric MHC class I protein having one or more amino acid mutations at residues 223-229 of the human MHC class I α3 domain. TCR activation is assessed by the reporter readout, i.e., GFP production. GFP$^+$ cells are then isolated by FACS and the variable region of the recombinant TCR is amplified by PCR and sequenced.

In another embodiment, the peptide-human/mouse chimeric MHC class I protein having one or more amino acid mutations at residues 223-229 of the human MHC class I α3 domain is expressed on a cell, e.g., an antigen presenting cell.

b) CD8 Independent TCR Activation

In another embodiment, the TCRα$^-$/β$^-$ CD8$^-$ CD3$^+$ chiCD8αβ$^+$/flox$^+$ TRE-GFP host cell library expressing recombinant TCRs is subjected to a two round screening protocol.

In the first round, the TCR cell library is screened for peptide-MHC I activation in the presence of the cell surface expression of the chimeric human/mouse CD8. Positive TCR cell clones that engage the target peptide-MHC I complexes in the presence of the chimeric CD8 co-receptor are then identified.

In the second round, delivery of a Cre recombinase to the identified positive TCR cell clones results in the deletion of the recombinant chimeric CD8 co-receptor and the subsequent removal of the CD8 co-receptor from the cell surface.

FACS sorted positive TCR cell clones that no longer express chimeric CD8 on their cell surface are again screened for peptide-MHC I activation. Positive TCR cell clones that engage the target peptide-MHC I complexes in the absence of CD8 co-receptor are then identified as high affinity binders.

In another embodiment, high affinity TCRs are isolated that bind to a desired peptide-MHC I complex having one or more amino acid mutations at residues 223-229 of the MHC I α3 domain.

In one embodiment, a mouse TCRα$^-$/β$^-$ CD8$^-$ CD3$^+$ TRE-GFP host cell library expressing recombinant TCRs on the cell surface is contacted with a peptide-chiMHC I protein having one or more amino acid mutations at residues 223-229 of the MHC I α3 domain. TCR activation is assessed by the reporter readout, i.e., GFP production. GFP$^+$ cells are then isolated by FACS and the variable region of the recombinant TCRs is amplified by PCR and sequenced.

In another embodiment, the peptide-chiMHC I protein having one or more amino acid mutations at residues 223-229 of the MHC I α3 domain is expressed on a cell, e.g., an antigen presenting cell.

c) CD4 Dependent TCR Activation

In one embodiment, the TCRα$^-$/β$^-$ CD4$^-$ CD3$^+$ chiCD4$^+$/flox$^+$ TRE-GFP host cell library expressing recombinant TCRs is assayed for binding to any T cell epitope of interest in the context of various MHC class II alleles, either directly or indirectly fluorescently labeled.

In one embodiment, the cells bearing an appropriate TCR can be captured and enriched by FACS and the α and β chains recovered and characterized.

In other embodiments, peptide-MHC II engagement by the cell surface expression of an individual TCR can be determined by the expression of activation marker (e.g., CD69 or CD137), triggering of signaling pathway (e.g., NFAT signaling, IL-2 signaling, activator protein-1 signaling, or NFκB/Rel signaling), production of cytokine (e.g., IL-2, TNF-α, or IFN-γ), calcium flux, cell proliferation (e.g., proliferation of T cells), and activation of reporter system (e.g., IL-2-EGFP reporter system).

In another embodiment, TCRα$^-$/β$^-$ CD4$^+$ CD3$^+$ TRE-GFP host cell library expressing recombinant TCRs can be screened for TCR activation after presentation with peptide-chiMHC II protein in which the human β-chain β2 domain comprises one or more mutations that attenuate or abrogate binding of the variant MHC II to CD4 (Rolf Li-Yun KonigHuang & Ronald N. Germain (1992) Nature 356, 796-798, which is incorporated herein in its entirety).

In another embodiment, TCRα$^-$/β$^-$ CD4$^+$ CD3$^+$ TRE-GFP host cell library expressing recombinant TCRs can be screened for TCR activation after presentation with a peptide-chiMHCII expressed on the surface of a cell.

d) CD4 Independent TCR Activation

In another embodiment, the TCRα$^-$/β$^-$ CD4$^-$ CD3$^+$ chiCD4/flox$^+$ TRE-GFP host cell library expressing recombinant TCRs is subjected to a two round screening protocol.

In the first round, the TCR cell library is screened for peptide-MHC II activation in the presence of the cell surface expression of the chimeric human/mouse CD4. Positive TCR cell clones that engage the target peptide-MHC II complexes in the presence of the chimeric CD4 co-receptor are then identified.

In the second round, delivery of a Cre recombinase to the identified positive TCR cell clones results in the deletion of the recombinant chimeric CD4 co-receptor and the subsequent removal of the CD4 co-receptor from the cell surface.

FACS sorted positive TCR cell clones that no longer express CD4 on their cell surface are again screened for peptide-MHC II activation. Positive TCR cell clones that engage the target peptide-MHC II complexes in the absence of CD4 co-receptor are then identified.

e) In Vitro Evolution of a TCR Variable Region

Directed protein evolution is a very powerful tool to generate TCRs for a specific peptide-MHC complex. The process involves engineering or modifying a TCR so that mutants of the TCR exhibit different characteristics (e.g., increased affinity and/or enhanced signaling capability) for the cognate peptide-MHC complex (the original antigen that the wild-type TCR cells was specific for). Thus, the wild-type TCR can be used as a template for producing mutagenized libraries in one or more of the CDRs, and mutants with different characteristics (e.g., higher affinity and/or enhanced signaling capability) can be selected by binding to the cognate peptide-MHC complex.

In one embodiment, variable regions of TCR α/β can be mutated by somatic hypermutation in the presence of Activation-induced cytidine deaminase (AID), an enzyme that deaminates cytosine base to produce uracil, which is recognized as a thymine. Exemplary methods of using AID for in vitro mutagenesis are disclosed in, for example, U.S. Pat. Nos. 8,685,897 and 8,603,950, which are incorporated by reference herein in their entireties). In vivo methods of AID mutagenesis are disclosed, for example, in U.S. Patent Application No. 2012/0309011, which is incorporated herein in its entirety.

Some examples of high affinity include an equilibrium binding constant for a target ligand of between about $10^{-4}$ M and $10^{-12}$ M and all individual values and ranges therein. This range encompasses affinities between those reported to be wild type affinities ($10^{-4}$ to $10^{-6}$M), and those which have been isolated by directed evolution (about $10^{-12}$ M).

Those of skill in the art, through standard mutagenesis techniques, in conjunction with the assays described herein, can obtain altered TCR sequences and test them for particular binding affinity and/or specificity. Useful mutagenesis techniques known in the art include, without limitation, de novo gene synthesis, oligonucleotide-directed mutagenesis, region-specific mutagenesis, linker-scanning mutagenesis, and site-directed mutagenesis by PCR (see, e.g., Sambrook et al. (1989) and Ausubel et al. (1999)).

In obtaining variant TCR coding sequences, those of ordinary skill in the art will recognize that TCR-derived proteins may be modified by certain amino acid substitutions, additions, deletions, and post-translational modifications, without loss or reduction of biological activity. In particular, it is well known that conservative amino acid substitutions, that is, substitution of one amino acid for another amino acid of similar size, charge, polarity and conformation, are unlikely to significantly alter protein function.

Additional mutations in any region or regions of the variable region may result in a stabilized protein. In one embodiment, one or more additional mutations are in one or more of CDR1, CDR2, HV4, CDR3, FR2, and FR3 of a TCR α chain or β chain. The regions used for mutagenesis can be determined by directed evolution, where crystal structures or molecular models are used to generate regions of the TCR which interact with the ligand of interest (antigen, for example). In other examples, the variable region can be reshaped, by adding or deleting amino acids to engineer a desired interaction between the TCR and the ligand.

2) Screening Cellular TCR Display Libraries in the Presence or Absence of Peptide-Variant MHC Complexes Disclosed herein are methods for the isolation and identification of a T cell receptor (TCR) with a desired characteristic comprising transducing or transfecting host cells that do not express endogenous TCR with a library of expression constructs encoding different recombinant TCRs to generate a recombinant TCR cellular library in which cells express different recombinant TCRs on their cell surface, selecting cells expressing the TCRs for the desired characteristic in the presence of an MHC molecule complexed with a peptide of interest, where the MHC molecule comprises an MHC chain that is a variant of a wild type MHC chain, and where the variant MHC chain binds to a co-receptor with reduced affinity compared to the affinity of the wild type MHC chain for the co-receptor, and isolating and identifying the expression construct encoding the recombinant TCR with the desired characteristic.

Examples of a desired characteristic include, but are not limited to, high selectivity for the desired peptide-variant MHC complex, high affinity for the desired peptide-variant MHC complex, and demonstration of a positive functional readout in the presence of the desired peptide-variant MHC complex.

a) TCR Activation by Peptide-Variant MHC I Complexes

In one embodiment, a T cell receptor (TCR) with a desired characteristic is isolated and identified by a method comprising transducing or transfecting host cells that do not express endogenous TCR with a library of expression constructs encoding different recombinant TCRs to generate a recombinant TCR cellular library in which cells express different recombinant TCRs on their cell surface, selecting cells within the cellular library for a desired characteristic in the presence of a desired peptide-variant MHC I complex, where the MHC I molecule comprises an MHC I α chain that is a variant of a wild type MHC I α chain, and where the variant MHC I α chain binds to the CD8 co-receptor with reduced affinity compared to the affinity of the wild type MHC I α chain for the CD8 co-receptor, and isolating and identifying the expression construct encoding the recombinant TCR with the desired characteristic.

Examples of a desired characteristic include, but are not limited to, a T cell receptor (TCR) having high selectivity or high affinity for the desired peptide-variant MHC complex.

In one embodiment, recombinant TCRs are selected in the presence of a desired peptide-variant MHC I complex by measuring a functional readout of TCR activation, for example, the activation of one or more reporter systems.

In one embodiment, the desired peptide-MHC I complex is a cell free peptide-MHC I complex. In one embodiment, the desired peptide-MHC I complex comprises a dimer, a tetramer, or a multimer. In one embodiment, the desired peptide-MHC I complex is expressed on the surface of a cell, e.g., a mammalian cell, a yeast cell, or an insect cell. In one embodiment, the mammalian cell is a T2 cell.

In one embodiment, the variant MHC I α chain is a variant of HLA-A2 α chain. In one embodiment, the variant MHC I molecule comprises one or more mutations within the α3 region of the MHC I α chain that attenuates or prevents binding to the CD8 co-receptor. For example, the variant MHC I molecule can have an A245V mutation or a D227K/T228A mutation, numbered according to the mature protein sequence.

Examples of α3 region mutations are described, for example, in Pittet et al. J Immunol. 2003 171(4):1844-9; Dutoit et al. J Immunol. 2003 170(10):5110-7 and U.S.

Patent Publication No. 2004/0146520, which are incorporated by reference herein in their entireties.

In one embodiment, the desired peptide-variant MHC I complex is a cell free peptide-variant MHC I complex. In one embodiment, the desired peptide-variant MHC I complex comprises a dimer, a tetramer, or a multimer. In one embodiment, the desired peptide-variant MHC I complex is expressed on the surface of a cell, e.g., a mammalian cell, a yeast cell, or an insect cell.

b) TCR Activation by Peptide-Variant MHC II Complexes

In one embodiment, a T cell receptor (TCR) with a desired characteristic is isolated and identified by a method comprising transducing or transfecting host cells that do not express endogenous TCR with a library of expression constructs encoding different recombinant TCRs to generate a recombinant TCR cellular library in which cells express different recombinant TCRs on their cell surface, selecting cells within the cellular library for a desired characteristic in the presence of a desired peptide-variant MHC II complex, where the MHC II molecule comprises an MHC II β chain that is a variant of a wild type MHC II β chain, and where the variant MHC II β chain binds to the CD4 co-receptor with reduced affinity compared to the affinity of the β chain of a wild type MHC II for the CD4 co-receptor, and isolating and identifying the expression construct encoding the recombinant TCR with the desired characteristic.

In one embodiment, a variant MHC class II β-chain comprises one or mutations in the β2 domain that attenuate or abrogate binding of the variant MHC II to CD4 (Rolf Li-Yun KonigHuang & Ronald N. Germain (1992) Nature 356, 796-798, which is incorporated herein in its entirety).

Examples of a desired characteristic include, but are not limited to, a T cell receptor (TCR) having high selectivity or high affinity for the desired peptide-variant MHC II complex.

In one embodiment, recombinant TCRs are selected in the presence of a desired peptide-variant MHC II complex by measuring a functional readout of TCR activation, for example, the activation of one or more reporter systems.

In one embodiment, the desired peptide-variant MHC II complex is a cell free peptide-MHC II complex. In one embodiment, the desired peptide-variant MHC II complex comprises a dimer, a tetramer, or a multimer. In one embodiment, the desired peptide-variant MHC II complex is expressed on the surface of a cell, e.g., a mammalian cell, a yeast cell, or an insect cell. In one embodiment, the mammalian cell is an antigen-presenting cell (APC).

V. EXAMPLES

Examples have been set forth below for the purpose of illustration and to describe certain specific embodiments of the invention. However, the scope of the claims is not to be in any way limited by the examples set forth herein. Various changes and modifications to the disclosed embodiments will be apparent to those skilled in the art and such changes and modifications including, without limitation, those relating to the packaging vectors, cell lines and/or methods of the invention may be made without departing from the spirit of the invention and the scope of the appended claims.

The practice of the invention employs, unless otherwise indicated, conventional molecular biological and immunological techniques within the skill of the art. Such techniques are well known to the skilled worker, and are explained fully in the literature. See, e.g., Bailey, J. E. and Ollis, D. F., Biochemical Engineering Fundamentals, McGraw-Hill Book Company, N Y, 1986; Current Protocols in Immunology, John Wiley & Sons, Inc., NY, N.Y. (1991-2015), including all supplements; Current Protocols in Molecular Biology, John Wiley & Sons, Inc., NY, N.Y. (1987-2015), including all supplements; Sambrook, et al., Molecular Cloning: A Laboratory Manual, 2nd Edition, Cold Spring Harbor, N.Y. (1989); and Harlow and Lane, Antibodies, a Laboratory Manual, Cold Spring Harbor, N.Y. (1989), all the contents of which are incorporated by reference herein in their entireties.

Example 1: Generation of a Murine T Cell Line Suitable for TCR Display

To develop a T cell line for TCR display, a murine thymoma derived TCR negative mouse CD8 positive cell line ("MTCD8") was used as a starting point. MTCD8 cells were cultured in SF-IMDM medium (Amimed) supplemented with 2% fetal calf serum (FCS, Amimed) and 0.1% β-mercaptoethanol in Erlenmeyer flasks (80 rpm in a Multitron Standard incubator, INFORS HT) or filter cap cell culture flasks (Cellstar) at 37° C. under 10% $CO_2$.

The cell line MTCD8 was modified as described below to generate a recipient cell line for mammalian TCR display.
1) Generation of MTCD8-Derived Cell Line Expressing a Human-Mouse Chimeric CD8

To facilitate the expression of human TCR in MTCD8 cells, CD8 α and β chains were expressed in MTCD8 cells as chimeric proteins comprising human CD8 extracellular region fused to mouse CD8 transmembrane and intracellular regions. The resulting chimeric CD8α (chiCD8α) and CD8β (chiCD8β) comprise the amino acid sequences of SEQ ID NOs.: 1 and 2, respectively.

Briefly, chiCD8α and chiCD8β genes were each packaged separately into replication-incompetent retroviral particles. HEK 293 cells (ATCC) were co-transfected with three different vectors: a pVPack vector encoding gag-pol genes (pVPack vector system, Stratagene), a second vector encoding the PVC 211 env gene, and a retroviral vector encoding chimeric CD8α or CD8β. Transfection was conducted using the FuGENE 6 Transfection Reagent (Roche Applied Science) according to the manufacturer's instructions. The resulting retroviral supernatant was harvested two or three days later and used directly to transduce MTCD8 cells.

MTCD8 cells expressing chimeric CD8α and CD8β (MTCD8 chiCD8αβ+) were enriched using anti-human CD8α FITC (eBioscience, Cat. No.: 11-0086) and anti-human CD8β APC (BD Biosciences, Cat. No.: 641058) by fluorescence-activated cell sorting (FACS). FACS was performed using BD FACSAria I or II with FACSDiva software (Becton-Dickinson). Each round of FACS enrichment was performed using a calibrated amount of FITC- or APC-labeled antibody per $1.0 \times 10^6$ cells for 30 minutes at 4° C. Fc receptor blocker (BD Biosciences, Cat. No.: 553142) was used to eliminate background binding of the Fc region of the detection antibodies to MTCD8 cells. MTCD8 cells that did not express chimeric CD8 were used to detect non-specific binders. All the washes between labeling reactions were conducted by centrifuging cells for 5 minutes at 300 g at 4° C. in PBS (PAA) with 2% FCS. After appropriate rounds of bulk enrichment, a population of MTCD8 chiCD8α3+ cells became detectable by flow cytometry.
2) Depletion of Mouse CD8 from MTCD8 Cells or Derivatives MTCD8 cells or MTCD8 cells expressing chimeric CD8 as generated above were sorted by Fluorescence-activated cell sorting (FACS) to enrich cells that did not express mouse CD8α or CD8β. The following antibodies were used:

anti-mouse CD8α APC (BD Biosciences, Cat. No.: 561093), anti-mouse CD8β PE (BD Biosciences, Cat. No.: 550798), anti-human CD8α PE (eBioscience, Cat. No.: 12-0086), and anti-human CD8β APC (BD Biosciences, Cat. No.: 641058). FACS was performed using FACSAria I or II with FACS-Diva software (Becton-Dickinson). Each round of FACS enrichment was performed using a calibrated amount of PE- or APC-labeled antibody per $1.0 \times 10^6$ cells for 30 minutes at 4° C. Fc receptor blocker (BD Biosciences, Cat. No.: 553142) was used to eliminate background binding of the Fc region of the detection antibodies to MTCD8 cells or derivatives. All the washes between labeling reactions were conducted by centrifuging cells for 5 minutes at 300 g at 4° C. in PBS (PAA) with 2% FCS.

After appropriate rounds of bulk enrichment, a population of MTCD8 cells that did not express mouse CD8 became detectable by flow cytometry (MTCD8 mCD8αβ– chiCD8αβ– and MTCD8 mCD8αβ– chiCD8αβ+) and single T cells were sorted in 96-well plates. These single T cells grew into T cell clones in about one week and cells in these clones did not express mouse CD8 on their surface anymore.

Subsequently, these single cell clones were analyzed by flow cytometry to confirm the lack of the surface expression of mouse CD8α and CD8β and wherever applicable, the positive surface expression of chimeric CD8α and CD8β. The flow cytometry analysis was performed in 96-well plates (Cellstar) on BD FACSCalibur. All the flow cytometer data were analyzed using the FlowJo software (Treestar).

3) Selection of Clones Based on Transduction Efficiency, APC Background, and Signaling Capability In this example, suitable clones of (i) MTCD8 mCD8αβ– chiCD8α3+ and (ii) MTCD8 mCD8αβ– chiCD8αβ– were selected that satisfied the following characteristics: (i) high transduction efficiency, (ii) low APC background, and (iii) strong TCR-mediated signaling capability.

Briefly, MTCD8 mCD8αβ– chiCD8αβ+ cells and MTCD8 mCD8αβ– chiCD8αβ– cells were replica plated and transduced to express the α and β chains of chimeric TCR C58 (MTCD8 mCD8αβ– chiCD8αβ+ chiC58αβ+ and MTCD8 mCD8αβ– chiCD8αβ– chiC58αβ+). C58, which refers to c58c61 in U.S. Pat. No. 8,367,804 (herein incorporated by reference in its entirety), is a TCR specific for a peptide derived from NY-ESO-1 in the context of HLA-A*0201. C58 was expressed as a chimeric TCR with human variable regions fused to murine non-variable regions to ensure proper anchoring and interaction with murine CD3 and proper triggering of murine signaling pathways. The α and β chains of chimeric C58 comprise the amino acid sequences of SEQ ID NOs: 7 and 8, respectively. The transduced cells were stained using a calibrated amount of anti-mouse TCR PE (BD Biosciences, Cat. No.: 553172) per $1.0 \times 10^6$ cells for 30 minutes at 4° C. Fc receptor blocker (BD Biosciences, Cat. No.: 553142) was used to eliminate background binding of the Fc region of the detection antibody to MTCD8 cell derivatives. To detect non-specific binders, TCR negative MTCD8 cells were used. All the washes were conducted by centrifuging cells for 5 minutes at 300 g at 4° C. in PBS (PAA) with 2% FCS. The flow cytometry was performed using a FACSCalibur (Becton Dickinson) and data were analyzed using the FlowJo software (Treestar). Most clones showed 0-30% positivity for TCR expression after transduction. The clones with high transduction efficiency (20-30% positivity for TCR expression) and low APC background staining were selected (data not shown).

The MTCD8 mCD8αβ– chiCD8αβ+ chiC58αβ+ and MTCD8 mCD8αβ– chiCD8αβ– chiC58αβ+ cells generated above were activated and tested for IL-2 expression to identify clones with strong TCR-mediated signaling capability. Briefly, the cells were activated with plate-bound anti-CD3 antibody (eBioscience, Cat. No.: 16-0032) and soluble anti-CD28 antibody (eBioscience, Cat. No.: 16-0281). The supernatant was harvested and tested for IL-2 expression using a mouse IL-2 ELISA kit (eBioscience, Cat. No.: 88-7024). FIG. 1 shows exemplary IL-2 production data of individual clones from one testing. Only clones that showed strong IL-2 production were selected.

The selected MTCD8 mCD8αβ– chiCD8αβ+ clone was named AK-D10 and the selected MTCD8 mCD8αβ– chiCD8αβ– clone was named LOT-D08.

4) Expression of Chimeric DMF4 and DMF5 in AK-D10 Cells

Next, chimeric DMF4 and DMF5, both of which are MART-1 reactive TCRs in the context of HLA-A*0201, were expressed in the AK-D10 cells (MTCD8 mCD8αβ– chiCD8αβ+) generated above. Both DMF4 and DMF5 TCRs are described in U.S. Pat. No. 8,088,379 (herein incorporated by reference in its entirety). To ensure proper interaction with murine CD3 and proper triggering of murine signaling pathways, both DMF4 and DMF5 were expressed as chimeric TCRs in which human variable regions were fused to murine non-variable regions. The α and β chains of chimeric DMF4 comprise the amino acid sequences of SEQ ID NOs: 9 and 10, respectively. The α and β chains of chimeric DMF5 comprise the amino acid sequences of SEQ ID NOs: 11 and 12, respectively. Chimeric DMF4 or DMF5 TCR α and β chain genes were each packaged separately into replication-incompetent retroviral particles. HEK 293 cells (ATCC) were co-transfected with three different vectors: a pVPack vector encoding gag-pol genes (pVPack vector system, Stratagene), a second vector encoding the PVC 211 env gene, and a retroviral vector encoding chimeric TCR α or β chains. Transfection was conducted using the FuGENE 6 Transfection Reagent (Roche Applied Science) according to the manufacturer's instructions. The resulting retroviral supernatant was harvested three days later and used directly to transduce AK-D10 cells.

AK-D10 cells expressing chimeric DMF4 or DMF5 (AK-D10 chiTCRαβ+) were enriched using HLA-A*0201 Mart-1 (ELAGIGILTV) (SEQ ID NO: 30) tetramer PE (MBL, Cat. No.: TO 01008) and hamster anti-mouse TCR β chain antibody APC (BD Biosciences, Cat. No.: 553174) by fluorescence-activated cell sorting (FACS) using BD FACSAria I or II with FACSDiva software (Becton-Dickinson). Each round of FACS enrichment was performed using a calibrated amount of PE-labeled antigen or APC-labeled antibody per $1.0 \times 10^6$ cells for 30 minutes at 4° C. Fc receptor blocker (BD Biosciences, Cat. No.: 553142) was used to eliminate background binding of the Fc region of the detection antibody to AK-D10 cells. TCR negative AK-D10 cells were used to detect non-specific binders. All the washes between labeling reactions were conducted by centrifuging cells for 5 minutes at 300 g at 4° C. in PBS (PAA) with 2% FCS.

Figure 2A:
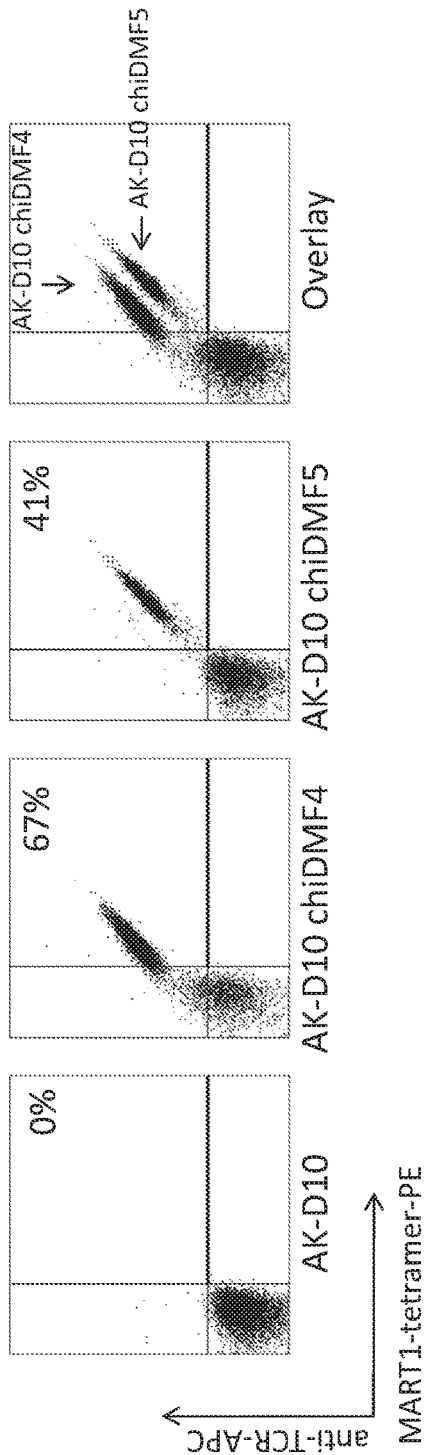
FIGS. 2A, 2B, 2C, 2D, and 2E.

After an appropriate number of bulk enrichment steps, a population of AK-D10 cells expressing chimeric DMF4 or DMF5 became detectable by flow cytometry. FIG. 2A shows co-staining of PE-labeled HLA-A*0201 Mart-1 (ELA-GIGILTV (SEQ ID NO: 30)) tetramer and APC-labeled anti-TCR β chain antibody. Consistent with the fact that DMF5 has higher affinity than DMF4, under similar TCR expression levels, the cells expressing chimeric DMF5 showed stronger binding to the peptide-MHC tetramer than the cells expressing chimeric DMF4 did.

5) Correlation of TCR Peptide-MHC Interaction and TCR-Mediated Signaling Strength In this example, AK-D10 cells expressing chimeric DMF4 or DMF5 as generated above were activated using peptide-MHC complexes and then tested for IL-2 production. DimerX (BD Biosciences, Cat. No.: 551263) is a HLA-A2:Ig fusion protein consisting of three extracellular major histocompatibility complex (MHC) class I HLA-A2 domains that are fused to the VH regions of mouse IgG$_1$. DimerX can be loaded with any peptide restricted to HLA-A2. Peptide loading was conducted by incubating DimerX and peptide of interest overnight at 37° C.

Figure 2B:
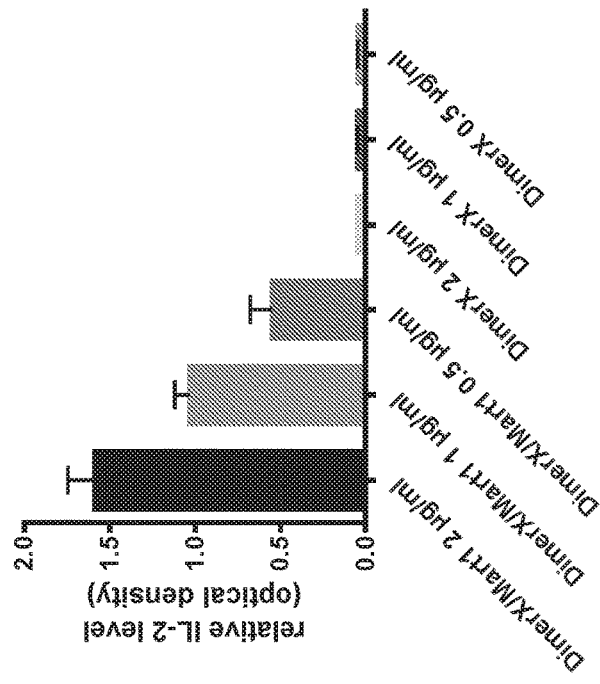
Figure 2C:
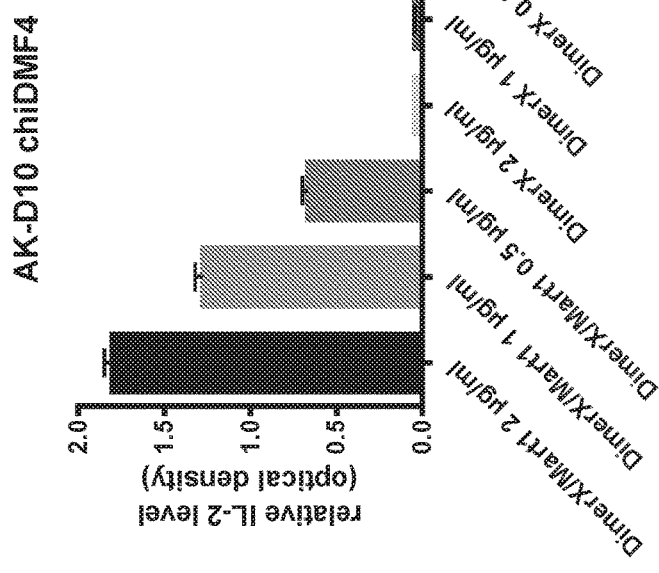

AK-D10 cells expressing chimeric DMF4 or DMF5 on the surface were activated using DimerX loaded with Mart-1 peptide ELAGIGILTV (SEQ ID NO: 30) at different concentrations (2 µg/ml, 1 µg/ml, and 0.5 µg/ml). Briefly, 96-well plates were coated with DimerX/peptide complexes and incubated for 3 hours at 37° C., followed by a wash with PBS. Subsequently, 1×10$^5$ AK-D10 cells expressing chimeric DMF4 or DMF5 were resuspended in 150 µl of SF-IMDM and added to 96-well plates. After overnight incubation, the supernatant was tested for IL-2 expression using a mouse L-2 ELISA kit (eBioscience, Cat. No.: 88-7024). DimerX/peptide complexes induced dose-dependent IL-2 production in AK-D10 cells expressing chimeric DMF4 (FIG. 2B) or chimeric DMF5 (FIG. 2C). DimerX alone without any peptide was used as a negative control.

Figure 2E:
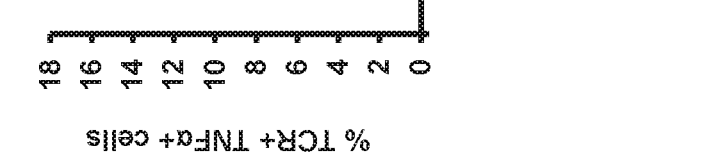
Figure 2D:
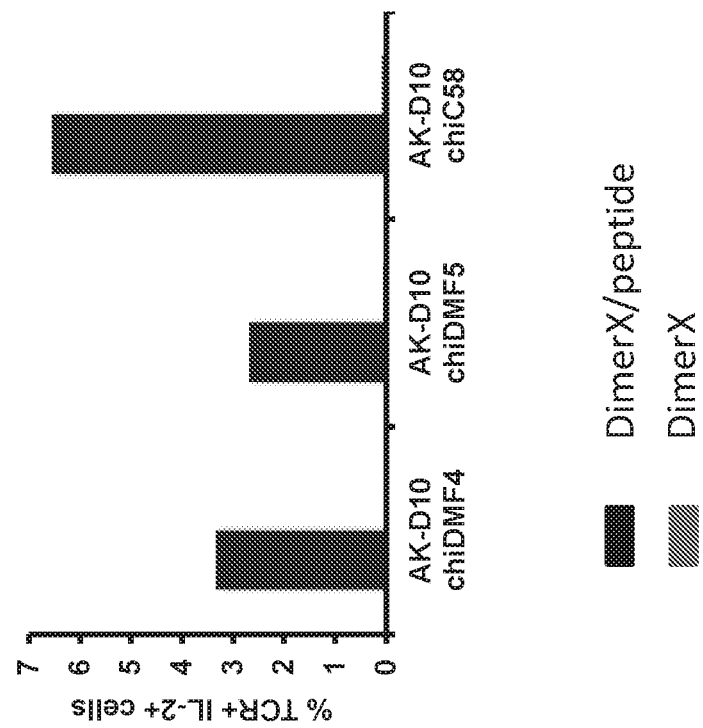

AK-D10 cells expressing chimeric DMF4, DMF5, or C58 were activated using DimerX/peptide complexes in an assay similar to the assay described above and tested for IL-2 and TNFα production using intracellular cytokine staining (ICS). Briefly, five hours before staining, the cells were treated with monensin (eBioscience, Cat. No.: 00-4505). The cells were then fixed and permeabilized with Cytofix-Cytoperm (BD Biosciences, Cat. No.: 554714) for intracellular staining according to the manufacturer's instructions. Flow cytometry staining was conducted using a calibrated amount of anti-mouse IL-2 PE (eBioscience, Cat. No.: 12-7021) or anti-mouse TNFα PE (eBioscience, Cat. No.: 12-7321) per 1.0×10$^6$ cells for 30 minutes at 4° C. Fc receptor blocker (BD Biosciences, Cat. No.: 553142) was used to eliminate background binding of the Fc regions of the detection antibodies to AK-D10 cells. AK-D10 cells expressing chimeric TCR without DimerX/peptide activation were used as negative controls. All the washes between labeling reactions were conducted by centrifuging cells for 5 minutes at 300 g at 4° C. in PBS (PAA) with 2% FCS. Cells were then subjected to flow cytometry analysis. TCR positive cells were gated and the percentage of TCR+IL-2+ and TCR+ TNFα+ cells was determined using the FlowJo software (Treestar). Consistent with IL-2 production detected by ELISA, the cells expressing chimeric TCR showed positive IL-2 (FIG. 2D) and TNFα (FIG. 2E) intracellular staining after activation using DimerX/peptide complexes.

Example 2: Generation of a Cellular TCR Display Library

The screening system described in the present Example is based on retroviral-mediated expression of full-length TCRs in mammalian cells, e.g., the MTCD8 cell or its derivatives. TCR α and β chain libraries are expressed from separate vectors by consecutive transduction. Retroviral transduction is an efficient method for the stable genetic modification of mammalian cells. The number of transduced α or β chains per cell can be regulated by modifying the multiplicity of infection (MOI) of viral titer, such that each cell produces on average, e.g., only one α and/or β chain, one α chain and multiple β chains, one β chain and multiple α chains, or multiple α and β chains. Separate retroviral expression vectors for TCR α or β chains are generated which transcriptionally couple the expression of a gene of interest (TCR α or β chains) via an internal ribosome entry site (IRES) to a reporter gene. Exemplary reporter genes include, but are not limited to, surface proteins such as human CD6 and CD7, and antibiotic resistance genes such as puromycin resistance genes.

1) Generation of a Human TCR Gene Library of High Diversity

CD4$^+$ or CD8$^+$ T cells separated by MACS (Miltenyi Biotec) or similar methods from leukapheresis materials from human donors were used to generate TCR α or β gene libraries. The source of the cells included healthy adult donors and cord blood. Additional sources can include fetal thymus, tumor infiltrating lymphocytes (TILs) isolated from cancer patients, and PBMCs from vaccinated patients.

Total mRNA was prepared from isolated T cells and cDNA was synthesized using SMARTer® RACE 5'/3' cDNA Synthesis Kit (Clontech Laboratories, Cat. No.: 634860). Library construction was performed separately per α chain or β chain family in order to achieve the desired high complexity of at least 1.0×10$^9$ colony-forming units. The variable regions of TCR α or β families were PCR amplified with family-specific primers, digested with restriction enzymes, and ligated into TCR α or β retroviral expression vector. Empty retroviral TCR α and β chain expression constructs contained the coding information for either α or β chain non-variable region and a restriction enzyme-flanked non-coding stuffer sequence upstream of the non-variable regions that can be replaced by cloned variable TCR α and β chain coding regions from human or synthetic origin. In cases where murine host cells were used to display human TCRs, the TCR expressing vectors were constructed to comprise human TCR variable regions fused to murine TCR non-variable regions to ensure proper anchoring and interaction with murine CD3 and proper triggering of murine signaling pathways. Single TCR α and β coding regions from selected TCRs were cloned to generate cells expressing a specific recombinant TCR on the cell surface. Furthermore, this method generated cells displaying diverse repertoires of TCR α and β chains isolated by RT-PCR from human T cell sources using TCR α and β chain specific primers, or generated by gene synthesis.

E. coli DH10B was transformed with the ligated TCR α or β chain library and plated on LB (Amp) agar plates. Bacteria colonies were collected and plasmid DNA was purified. DNA preparations of all TCR α or β families were pooled. The resultant TCR α or β chain library was quality controlled by performing next-generation sequencing (NGS). In NGS analysis, 1-3 µg of purified PCR product was used for sequencing reactions using MiSeq from Illumina in multiplexed runs. Sequence data obtained were filtered for complete TRAV-, TRAJ-, TRBV-, TRBD-, and TRBJ-reads, and cluster analyses were performed using the CD-HIT set of applications (www.cd-hit.org). Relative representation of TCR α or β families as percentage of total genes sequenced was analyzed.

2) Generation of a Human TCR Cellular Library of High Diversity

The murine thymoma derived TCR negative cell line MTCD8 and its derivatives (e.g., LOT-D08 and AK-D10 cells generated above) were selected as host cells for human TCR cellular libraries based in part on high permissiveness for transduction with ecotropic, MLV-enveloped retroviral particles. MTCD8 cells are deficient for endogenous mouse TCR expression and contain all necessary cellular components for expression, pairing, folding, signaling, and surface display of human TCRs. In addition, these cells grow in suspension and have a very short doubling time of approximately 10-12 hours, thus enabling fast expansion.

Illustrated in the following examples is the generation of a TCR cellular library in two phases: the TCR β chains were introduced in phase 1, and the TCR α chains were introduced in phase 2.

3) Retroviral Particle Production

TCR α and β chain gene libraries were each packaged separately into replication-incompetent retroviral particles. HEK 293 cells (ATCC) were co-transfected with three different vectors: a pVPack vector encoding gag-pol genes (pVPack vector system, Stratagene), a vector encoding the PVC 211 env gene, and a retroviral TCRα-IRES-human CD7 or TCRβ-IRES-human CD6 expression vector. Transfection was performed using FuGENE 6 Transfection Reagent (Roche Applied Science) according to the manufacturer's instructions. The resulting retroviral supernatant was harvested three days later and either used directly or kept frozen at −80° C. Retroviral particle titers of either TCR α or β chain retroviral particle stocks were determined experimentally by performing a test-transduction of MTCD8 cells and measuring human CD7 or human CD6 surface expression on the transduced population of MTCD8 cells. Based on the titration results, a dilution was calculated that yielded a desired average copy number of TCR α and β chains per transduced cell. Roughly, a 5% or less transduction rate gives >90% single copy integration of either the α or β chain. Subsequently, MTCD8 cells or derivatives were spin-transduced with retroviral supernatant for 3 hours at 30° C. TCR α and β chain gene libraries were transduced separately and sequentially. Transduction was performed in 6-well plates (Cellstar) with $1.5 \times 10^8$ cells per plate and in Eppendorf centrifuges. Following transduction, cells were transferred to Erlenmeyer flasks, with a cell concentration of $3.0 \times 10^6$ cells per 1 ml, and allowed to expand for 24 hours.

4) Transducing TCR β Chains (Phase 1)

In this example, TCR β chains were selected from a cord blood source (up to $3 \times 10^8$ different β chains), to: a) be 100% homologous to germline and b) represent all known functional β gene families in a ratio corresponding to their normal distribution in human peripheral blood. The TCRβ-IRES-human CD6 retroviral expression vectors were packaged into replication-deficient retroviral particles, which were then used to transduce MTCD8 cells or derivatives. Successful β chain gene transfer and subsequent expression were evidenced by the presence of human CD6 on the cell surface. After transduction, approximately 6% of the cells expressed human CD6, indicating successful integration and expression of single β chain genes. TCR β chain-expressing cells were isolated by enriching CD6 positive cells using fluorescence-activated cell sorting (FACS). Following sorting, TCR β chain-expressing cells were recovered and expanded for two days. The expanded TCR β chain cellular library was frozen in ready-to-use aliquots. Selection markers other than CD6 can also be used.

5) Transducing TCR α Chains (Phase 2)

The TCR α chain gene library was introduced in phase 2. Similar to the TCR β chain constructs, TCR α genes were co-expressed with an internal ribosome entry site (IRES)-coupled human CD7 marker gene. The human CD7 marker allows for titration of the retroviral particle-containing supernatant generated on empty MTCD8 cells, such that less than 5% of the transduced cells express TCR α chains. Under these conditions, approximately 90% of the cells contain a single integrated TCR α gene copy.

Following transduction of the TCR α-chain library, cells were stained for TCR expression using an anti-mouse TCRβ-PE antibody (BD Biosciences, Cat. No.: 553172) and analyzed by flow cytometry. TCR-expressing cells were then isolated by magnetic-activated cell sorting (MACS) using anti-Biotin Microbeads (Miltenyi Biotec, Cat. No.: 130-090-485). Around $3.0\text{-}5.0 \times 10^9$ live cells were recovered after FACS or MACS from each TCR α chain transduction. More than 85% of these cells expressed surface TCR. The cells were then recovered and expanded for two days.

6) Quality Control of Cellular Library

Finally, at the end of the expansion phase, all the cells were pooled and frozen at −80° C. in cryobags, each bag containing approximately $1.0 \times 10^9$ viable cells.

The percentage of cells that have integrated one TCR α or one TCR β gene copy per cell was analyzed by amplifying the integrated TCR α or β gene and its adjacent vector regions from genomic DNA from ten single cell clones per transduction, and directly sequencing the PCR product. If the PCR product yielded one single clearly readable TCR α or β gene sequence, it was concluded that there was only one gene copy present in the cell of origin. In the cases where an overlap of at least two different TCR α or β gene sequences appeared after the co-amplified common vector region, it was concluded that there are at least two TCR α or TCR β copies present in that cell. From this analysis, it was possible to determine the percentage of the cells in the TCR cellular library that contained only one TCR α and one TCR β gene copy integrated into the host cell.

7) Generation of a Murine TCR Gene Library of High Diversity

Alternatively, TCR α and β gene libraries can be generated based on TCRs isolated from animals (e.g., HLA-A2 transgenic mice immunized with a target of interest). Murine TCR gene libraries can be constructed similarly as described above for human TCR gene libraries. Subsequently, similar protocols can be followed to generate a cellular library containing cells that do not express TCR endogenously displaying murine TCRs on the cell surface.

Example 3: Screening of TCR Cellular Library Using Peptide-MHC Complexes

1) Screening Protocol

Recombinant peptide-MHC complexes were purchased or synthesized and quality-checked for function prior to use. The TCR cellular library generated above was screened using labeled (e.g., fluorescent-labeled) peptide-MHC complexes (e.g., MHC tetramers, MHC dextramers, or DimerX loaded with peptides) by Fluorescence-activated cell sorting (FACS) using BD FACSAria I or II with FACSDiva software (Becton-Dickinson). Fluorescent-labeled anti-TCR antibody was used to visualize TCR expression level. Fc receptor blocker (BD Biosciences, Cat. No.: 553142) was used to eliminate background binding. The TCR cellular library was first screened using a calibrated amount of fluorescent-labeled MHC tetramers or DimerX/peptide complexes per $1.0 \times 10^6$ cells for 30 minutes at 4° C. To deplete non-specific binders, the positive hits from the first screening were further incubated with a calibrated amount of MHC tetramers with a negative control peptide or DimerX without a peptide per $1.0 \times 10^6$ cells for 15 minutes at 4° C. The cells that bound to MHC tetramers with a negative control peptide or DimerX without a peptide were gated out. All the washes between labeling reactions were conducted by centrifuging cells for 10 minutes at 300 rpm at 4° C. in PBS (PAA) with 2% FCS.

After an appropriate number of bulk enrichment steps, a population of TCR-expressing MTCD8 cells or derivatives that clearly and specifically recognized the antigen of interest became visible in flow cytometry analysis, and single T cells were sorted in 96-well plates. These single T cells grew into T cell clones in about one week.

Subsequently, these single cell clones were analyzed by flow cytometry to verify that they bound the antigen of interest and did not show non-specific background binding. In addition, the TCRs expressed on the surface of these single cell clones were analyzed for other properties, such as signaling and cross-reactivity towards other peptide-MHC complexes.

In addition to screening TCR-expressing cells based on their binding to peptide-MHC complexes of interest, TCR-expressing cells can also be screened based on functional readouts (e.g., expression of activation marker, triggering of signaling pathway, production of cytokine, calcium flux, cell proliferation, and activation of reporter assay) in the presence of the peptide-MHC complexes of interest. Hits from the binding screening can be compared with hits from the functional screening to identify TCRs that bind specifically to peptide-MHC complexes of interest and initiate relevant signaling pathways.

It may be possible to identify TCRs directed against self-antigens in a TCR library derived from T cells from cord blood or fetal thymus, partially because of the presence of a large number of immature T cells. These cells express TCRs against a myriad of self-antigens and have yet to be removed in T cell tolerance checkpoints as part of immune system maturation. With a two-tiered screening approach based on binding to peptide-MHC complexes of interest and then counter-screening against MHC molecules without peptides or with negative control peptides, non-poly-reactive TCRs are enriched.

In addition to the natural occurrence of self-reactive TCRs, a second mechanism may contribute to the likelihood of isolating self-reactive TCRs from the TCR library. As described above, when the TCR library is generated, the original cognate TCR α and β pairs as present in the T cells from human donors are separated, and each α or β chain is re-paired with a large number of non-original complementary β chains or α chains, respectively. This strategy leads to the expression of novel TCRs possibly showing altered properties such as different affinity or specificity for self-antigens.

The highly-diverse TCR library combined with stringent, antigen-specific screening methods allow for the isolation and identification of TCRs targeting human self-antigens or antigens that share high similarity with self-antigens.

2) TCR α and β Chain Gene Recovery

TCR α and β genes were recovered from individual T cell clones by plate-based PCR amplification: T cells were lysed and PCR for TCR α and β chain variable regions was performed separately, directly on the cell lysate, without prior isolation of genomic DNA. The amplified PCR product encoding either the TCR α or β chain was then cloned as a pool into appropriate expression vectors in a single restriction/ligation step using Type IIS restriction enzymes. In parallel, the PCR product was sequenced: if the T cell clone contained a single copy of α and β chain, reliable sequence information could be obtained at this stage. In cases where the T cell clones contained two or more integrated TCR α and/or β chains, individual chains were cloned into standard vectors and sequenced separately. The resulting ligated plasmid pool was transformed into *E. coli*, and DNA was recovered by bulk miniprep from the transformed cell-pool (no prior plating). The TCRs identified in this step were further analyzed for binding affinity, specificity, signaling capabilities, and/or other characteristics.

3) Alternative Cellular Library Compositions

The high efficiency of TCR gene transfer by retroviral transduction of MTCD8 derivatives as described herein allows generation of a variety of different types of cellular libraries customized for specific uses.

4) Multi-Copy TCR α and/or t Chain Libraries for De Novo Screens

By varying the multiplicity of infection, the average number of TCR α and β chain genes that are integrated into the genome of recipient MTCD8 cells or derivatives can be controlled. This strategy was used in the following variations.

To generate a cellular library that encompassed a maximal level of TCR diversity, libraries were constructed to express multiple different TCR α chains and multiple different TCR β chains per cell. Not all of the TCR α and β chains in a given cell would productively pair and thus many would fail to be presented on the surface. Still, by offering multiple options per cell, it was ensured that a much larger percentage of transduced cells expressed at least one functional TCR on the cell surface. This multi-copy library design offers two benefits: first, the library generation process is much more efficient (fewer drop-outs) and second, the TCR diversity in the resulting library may be substantially higher compared to using single-copy libraries. A potential further advantage is that the avidity effect caused by expressing many identical TCRs on the T cell surface is much reduced, which can in theory lead to the identification of higher affinity TCRs.

Using multi-copy libraries requires a second step to identify which TCR α chains pair with which β chains from a given T cell clone. A process was established as an exemplary approach to recovering α and β pairs: single T cells that demonstrated target-specific binding were sorted, positive T cell clones were pooled together, all TCR α and β chains from these pooled target-specific T cells were recovered using the recovery procedure described above (usually about 100-200 T cell clones), and a second cellular library was constructed by combining the now much smaller set of recovered TCR α and β chains in a single-copy format. A TCR screen was then repeated with this much smaller and more focused cellular library, and TCRs of interest were recovered following steps described above. In combination, these two steps would allow for coverage of much larger TCR diversity in comparison to using a single copy library from the beginning.

5) Guided Selection

Guided selection is a screening process that starts with an existing TCR with desired characteristics (for instance, a mouse TCR, a TCR isolated from a human patient, or a TCR isolated in a de novo screen) and sequentially replacing the individual chains. In an exemplary study, the original TCR β chain was replaced by screening the original TCR α chain in combination with a TCR β chain library, and then the selected TCR β chains were screened together with a diverse TCR α chain library to find a complementary new human TCR α chain (or vice versa). The high efficiency of the retroviral transduction process in combination with the fact that TCR α and β chain genes are in separate expression libraries allow for rapid generation of new libraries with any TCR composition.

Example 4: CD8-Dependent and -Independent Screening

CD8 forms a dimer, consisting of a pair of CD8 chains. The most common form of CD8 is composed of a CD8 α chain and a CD8 β chain. The extracellular IgV-like region of CD8 α chain interacts with the α3 portion of the MHC class I molecule. This interaction keeps the TCR of the cytotoxic T cell and the peptide-MHC complex of the target cell bound closely together during antigen-specific activation. The specificity of T cell activation depends on the interaction of peptide-MHC complexes and TCR. Other signals via co-receptors such as CD4 and CD8 or co-stimulatory interactions such as CD28 and CD8β/CD86 appear to act as amplifiers that increase the magnitude and/or duration of the TCR signals, and do not act independently. Different TCRs may show different levels of dependence on CD8 for binding and signaling. Generally speaking, TCRs that are CD8-independent tend to have higher-affinity towards peptide-MHC complexes. By enhancing the affinity of an existing TCR, it may be possible to change the T cell activation mediated by this TCR from CD8-dependent to CD8-independent. In addition, CD8-independence is a desired feature for developing soluble TCRs as therapeutics. Therefore, it is of significant interest to be able to interrogate the level of CD8-dependence of a TCR or a library of TCRs by modulating or abrogating the expression of CD8 on the display library/cell clone during library screening and clone characterization. This allows for a direct assessment in the same cell or cell population of the relative influence of CD8 on the binding strength and specificity, and the resulting intracellular signalling events of the interaction between TCR and the MHC-peptide complex.

Such a screening system can be achieved by using the Cre/loxP system. A Cre recombinase is a tyrosine recombinase enzyme derived from the P1 Bacteriophage. This enzyme uses a topoisomerase I like mechanism to catalyze site specific recombination events between two DNA recognition sites (loxP sites). The 34 base pair (bp) loxP recognition site consists of two 13 bp palindromic sequences, which flank an 8 bp spacer region. DNA between two loxP sites oriented in the same direction will be excised as a circular loop of DNA.

In this example, chimeric CD8α and CD8β comprising loxP sites flanking the transmembrane and cytoplasmic regions were expressed in LOT-D08 cells. Upon Cre-mediated recombination, the transmembrane and cytoplasmic regions of chimeric CD8α and CD8β are excised and consequently the host T cells do not express membrane-bound chimeric CD8.

1) Generation of LOT-D08 Cells Expressing Chimeric CD8 Flanked by loxP Sites

Chimeric CD8α and CD8β, which comprise human CD8 extracellular region fused to mouse CD8 transmembrane and cytoplasmic regions, were further modified to include two loxP sites flanking the mouse transmembrane and cytoplasmic regions (chiCD8α$^{flox}$ and chiCD8β$^{flox}$).

The chiCD8α$^{flox}$ and chiCD8β$^{flox}$ genes were each packaged separately into replication-incompetent retroviral particles. HEK 293 cells (ATCC) were co-transfected with three different vectors: a pVPack vector encoding gag-pol genes (pVPack vector system, Stratagene), a vector encoding the PVC 211 env gene, and a retroviral expression vector encoding chiCD8α$^{flox}$ or chiCD8β$^{flox}$. Transfection was performed using FuGENE 6 Transfection Reagent (Roche Applied Science) according to the manufacturer's instructions. The resulting retroviral supernatant was harvested three days later and used directly to transduce LOT-D08 cells.

LOT-D08 cells expressing chiCD8α$^{flox}$ and chiCD8β$^{flox}$ (LOT-D08 chiCD8α$^{flox}$+ chiCD8β$^{flox}$+) were enriched using anti-human CD8α FITC (eBioscience, Cat. No.: 11-0086) and anti-human CD8β APC (BD Biosciences, Cat. No.: 641058) by fluorescence-activated cell sorting (FACS). FACS was performed using BD FACSAria I or II with FACSDiva software (Becton-Dickinson). Each round of FACS enrichment was performed using a calibrated amount of FITC- or APC-labeled antibody per $1.0 \times 10^6$ cells for 30 minutes at 4° C. Fc receptor blocker (BD Biosciences, Cat. No.: 553142) was used to eliminate background binding of the Fc regions of detection antibodies to LOT-D08 cells. For detection of non-specific binders, LOT-D08 cells were used. All the washes between labeling reactions were conducted by centrifuging cells for 5 minutes at 300 g at 4° C. in PBS (PAA) with 2% FCS.

Subsequently, the LOT-D08 chiCD8α$^{flox}$+ chiCD8β$^{flox}$+ cells generated were analyzed by flow cytometry to verify the surface expression of chiCD8α$^{flox}$ and chiCD8β$^{flox}$. The flow cytometry analysis was performed using a BD FACSAria I or II with FACSDiva software (Becton-Dickinson). All the flow cytometer data were analyzed using the FlowJo software (Treestar).

2) Expressing Cre in LOT-D08 chiCD8α$^{flox}$+ chiCD8β$^{flox}$+ Cells

LOT-D08 chiCD8α$^{flox}$+ chiCD8β$^{flox}$+ cells generated above were transduced with an expression vector encoding a Cre recombinase. After expression of Cre, the cell clones were analyzed by flow cytometry to verify the lack of surface expression of chimeric CD8.

The Cre recombinase gene was packaged into replication-incompetent retroviral particles. HEK 293 cells (ATCC) were co-transfected with three different vectors: a pVPack vector encoding gag-pol genes (pVPack vector system, Stratagene), a vector encoding the PVC 211 env gene, and a retroviral vector encoding Cre-IRES-puromycin resistance gene. Transfection was performed using FuGENE 6 Transfection Reagent (Roche Applied Science) according to the manufacturer's instructions. The resulting retroviral supernatant was harvested three days later and either used directly or kept frozen at −80° C. Retroviral particle titers from Cre retroviral particle stocks were determined experimentally by performing a test-transduction of LOT-D08 cells and measuring puromycin resistance of the transduced population of LOT-D08 cells. The Cre recombinase was transduced in 1.5 ml Eppendorf tubes (Eppendorf) with $5 \times 10^5$ cells per tube. Following transduction, the cells were transferred to filter cap cell culture flasks (Cellstar), with a cell concentration of $1 \times 10^5$ cells per 1 ml, and allowed to expand for 24 hours at 37° C. under 10% $CO_2$ before puromycin was added to start selection.

Figure 3:
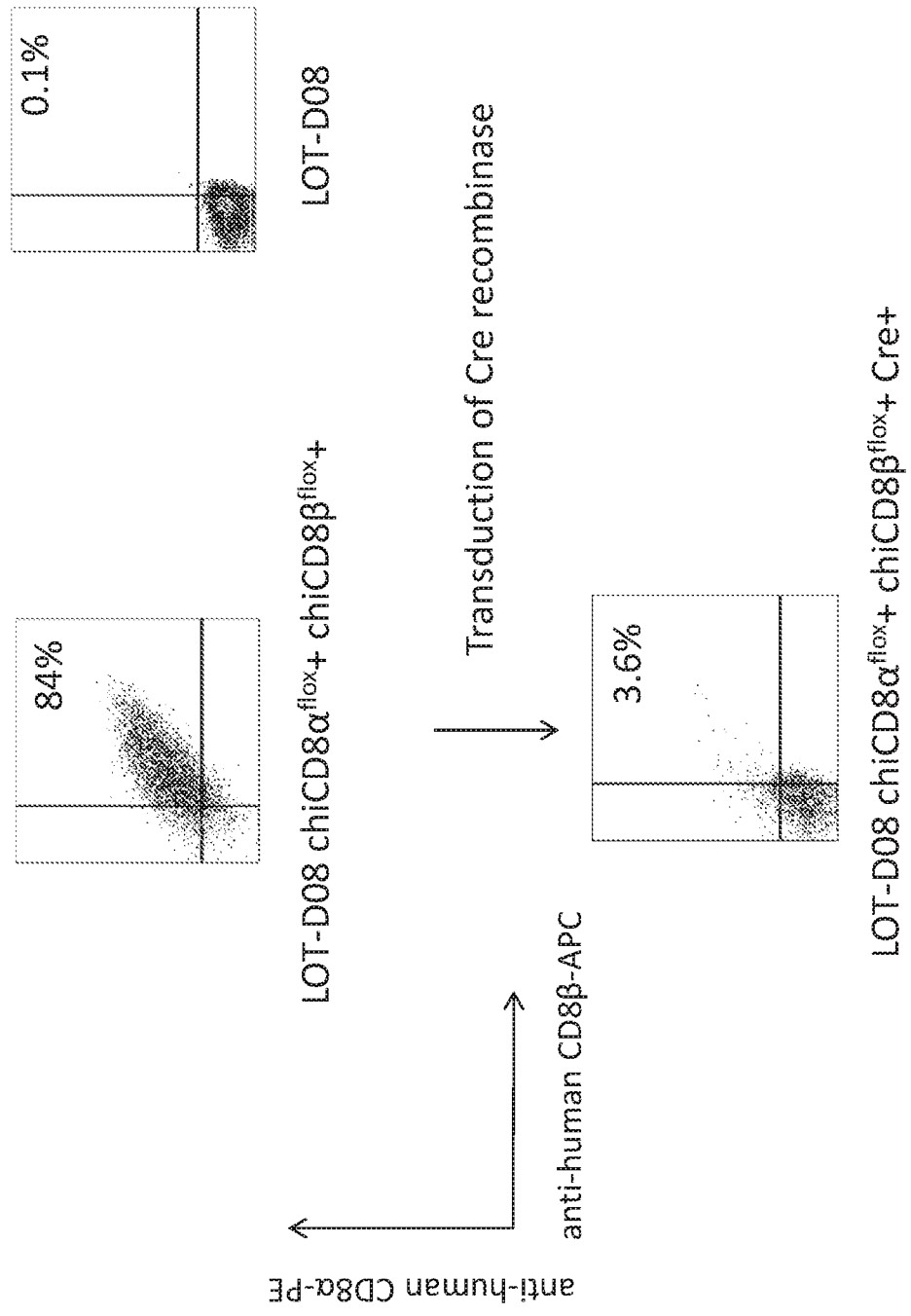
FIG. 3 is a set of flow cytometry plots showing the expression of chimeric CD8 on the surface of LOT-D08 chiCD8α$^{flox}$+ chiCD8β$^{flox}$+ cells and the subsequent elimination of chimeric CD8 from the cell surface following transduction with a Cre recombinase. The percentage of chiCD8α+ chiCD8β+ cells is indicated in each plot.

LOT-D08 chiCD8α$^{flox}$+ chiCD8β$^{flox}$+ cells expressing Cre (LOT-D08 chiCD8α$^{flox}$+ chiCD8β$^{flox}$+ Cre+) were analyzed by flow cytometry to confirm that these cells did not express chimeric CD8 on the cell surface using anti-human CD8α and anti-human CD8β antibodies. Fc receptor blocker (BD Biosciences, Cat. No.: 553142) was used to eliminate background binding of the Fc regions of detection antibodies to MTCD8 derivatives. All the washes between labeling reactions were conducted by centrifuging cells for 5 minutes at 300 g at 4° C. in PBS (PAA) with 2% FCS. The flow cytometer data were analyzed using the FlowJo software (Treestar). As shown in FIG. 3, transduction of the Cre recombinase effectively eliminated the expression of chimeric CD8 on the cell surface.

3) CD8 Dependence of TCR Binding to Peptide-MHC Complexes

Next, the impact of Cre recombinase-mediated CD8 deletion on the TCR/peptide-MHC interaction was examined. The display cells used in this example were LOT-D08 chiCD8αflox+ chiCD8β$^{flox}$+ cells transduced with a reporter construct comprising an IL-2 promoter and three NFAT binding sites operably linked to a nucleotide sequence encoding EGFP. These cells were named BB8 cells. See Example 5 for more details on the reporter construct. BB8 cells expressing chimeric TCR DMF4 or DMF5 were transduced to express the Cre recombinase as described above. The cells with or without Cre expression were stained using 0.2 µg/ml of iTag Tetramer/PE-HLA-A*02:01 Mart-1 (ELAGIGILTV) (SEQ ID NO: 30) (MBL, Cat. No.: T01008). TCR expression was examined using anti-mouse TCRβ antibody (BD Biosciences, Cat. No.: 553174). The presence or absence of surface CD8 expression was confirmed using anti-human CD8α-PE (eBioscience, Cat. No.: 12-0086). After staining, cells were washed and analyzed using FACSCalibur (BD Biosciences).

Figure 4A:
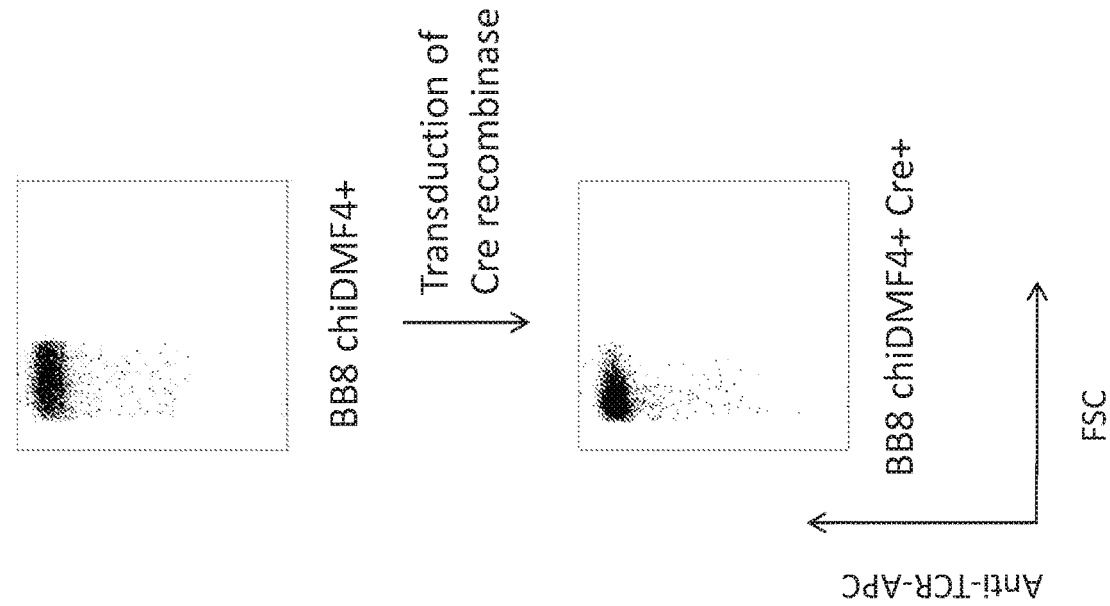
FIGS. 4A, 4B, and 4C are results from an assay testing binding of HLA-A*02:01 Mart-1 tetramer to BB8 cells (MTCD8 mCD8αβ− chiCD8α$^{flox}$+ chiCD8β$^{flox}$+IL-2-(NFAT)$_3$-EGFP+) expressing chimeric DMF4 (chiDMF4) or DMF5 (chiDMF5).
Figure 4B:
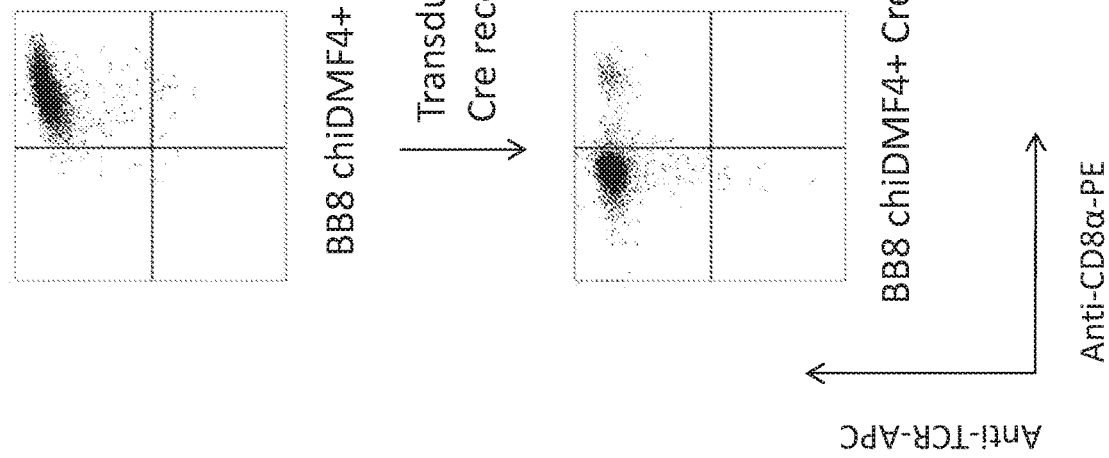
Figure 4C:
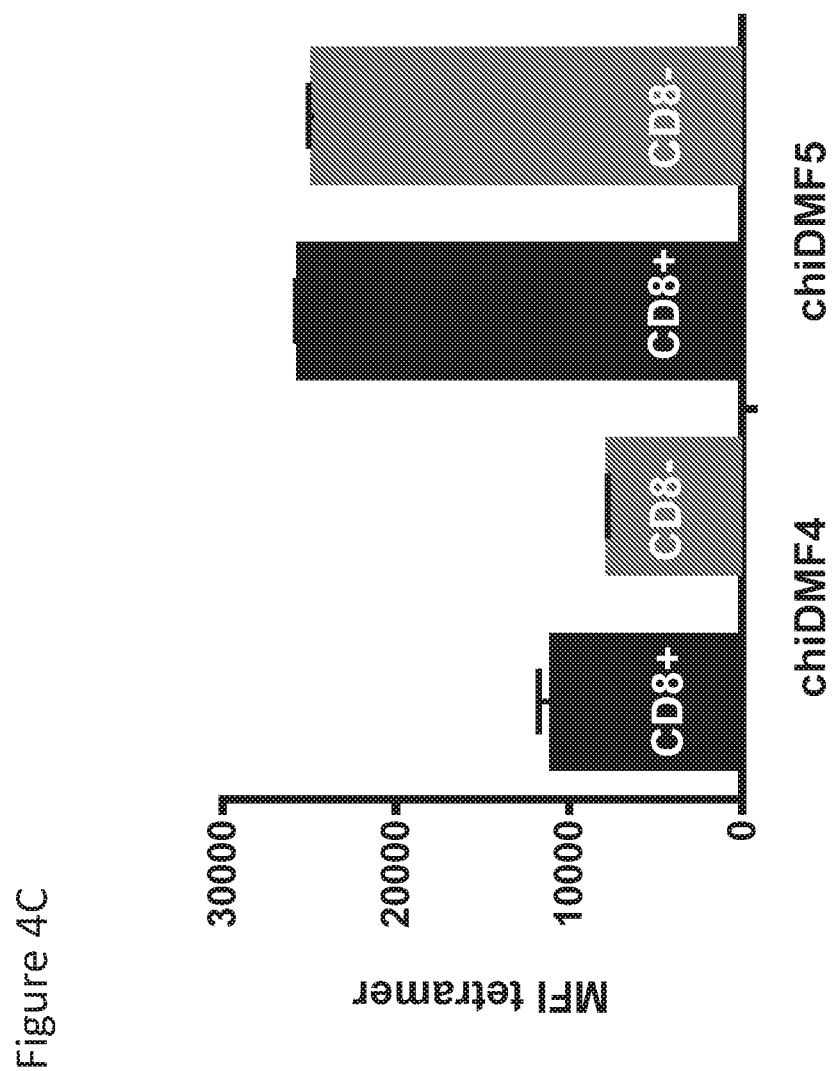

While Cre expression did not impact surface TCR levels (FIGS. 4A and 4B), the binding of chimeric DMF4 to Mart-1/HLA-A*0201 tetramer was reduced by 30% when CD8 expression was abolished by the Cre recombinase (FIG. 4C). In contrast, the high-affinity chimeric TCR DMF5 exhibited similar binding to tetramer in the presence or absence of CD8 (FIG. 4C). This study demonstrates that the display cells expressing loxP-flanked CD8 can be used to interrogate CD8-dependence of TCRs. The tetramer used in this study contains an A245V mutation in the MHC heavy chain α3 domain, which was shown to reduce overall binding strength of MHC to CD8 (see, e.g., Bodinier et al., Nat Med. 2000 June; 6(6):707-10, which is herein incorporated by reference in its entirety). Using wild type tetramer with stronger binding to CD8 may be able to increase sensitivity and allow for detection of even smaller differences between TCR/tetramer binding in the presence or absence of CD8.

4) CD8-Dependent and -Independent Screening Using the Cre/loxP System

LOT-D08 chiCD8α$^{flox}$+ chiCD8β$^{flox}$+ cells with or without reporter constructs are used to generate a diverse human TCR cellular library as described above. More specifically, TCR α and β chain gene libraries generated previously are each packaged separately into replication-incompetent retroviral particles and transduced into LOT-D08 chiCD8α$^{flox}$+ chiCD8β$^{flox}$+ cells sequentially. The resulting cellular library is quality-checked and then screened using peptide-MHC complexes of interest as described above.

Further, in order to identify CD8-independent TCRs, the cells that bind to peptide-MHC complexes in the screening above are transduced with a Cre-IRES-puromycin resistance gene construct as described previously. Upon expression of the Cre recombinase, the transmembrane and cytoplasmic regions of chiCD8α and chiCD8β are deleted and chimeric CD8 is no longer expressed on the cell surface.

After puromycin selection, TCR-expressing LOT-D08 chiCD8αflox+ chiCD8β$^{flox}$+ Cre+ cells are screened again using a calibrated amount of MHC-peptide complexes of interest followed by TCR α and β chain gene recovery using aforementioned methods.

With the ability to switch between CD8 positive and CD8 negative systems within a screening campaign, the display cell line LOT-D08 chiCD8α$^{flox}$+ chiCD8β$^{flox}$+ provides a versatile system that can be used readily to identify CD8-dependent low-to-intermediate affinity TCRs as well as CD8-independent high affinity TCRs.

5) CD8-Dependent and -Independent Screening Using Mutated MHC Molecules

Alternatively, when using cells constitutively expressing CD8, CD8-dependent and -independent screenings can be achieved by using wild type MHC class I molecules or MHC class I mutations that affect the CD8/MHC class I interaction. A number of such MHC class I mutants have been identified, including HLA-A2 A245V, which reduces, without completely abolishing, the binding of HLA-A2 to CD8 and HLA-A2 D227K/T228A, which abrogates CD8 binding without affecting the peptide-MHC/TCR interaction. A TCR cellular library can be screened directly against tetramers containing the HLA-A2 A245V mutant or the HLA-A2 D227K/T228A mutant loaded with peptides of interest. Alternatively, a two-step screening approach is employed. In this approach, a TCR cellular library expressing CD8 and TCRs on the cell surface is first screened using tetramers containing wild type HLA-A2 loaded with peptides of interest. The positive hits identified in this first step are then screened against tetramers containing the HLA-A2 A245V mutant or the HLA-A2 D227K/T228A mutant loaded with peptides of interest. CD8-independent high affinity TCRs can be isolated and identified.

Example 5: Screening TCR Cellular Library Using Reporter Assays

TCR cellular library can also be screened based on functional outcomes of interactions with peptide-MHC complexes. Possible readouts include expression of activation marker (e.g., CD69 or CD137), triggering of signaling pathway (e.g., NFAT signaling, IL-2 signaling, activator protein-1 signaling, or NFκB/Rel signaling), calcium fluxing, cell proliferation (e.g., proliferation of T cells), as well as production of cytokine (e.g., IL-2, TNF-α, or IFN-γ).

Alternatively, a derivative display cell line can be generated to express one or more reporter constructs. Commonly used reporter constructs encode a selectable marker (e.g., fluorescent or luminescent proteins, surface-expressed proteins, or antibiotic resistance markers) under the control of a target promoter (e.g., an IL-2 promoter comprising NFAT binding sites, an NFκB promoter comprising NFκB transcriptional response element, or an activator protein-1 promoter comprising TPA-induced transcriptional response element).

In this example, a derivative display cell line comprising an IL-2-EGFP reporter construct was generated. After activation of T cells and subsequent activation of the IL-2 signaling cascade, the IL-2 promoter is activated, leading to synthesis of EGFP. The readout, e.g., EGFP expression in this case, can be used to qualitatively or quantitatively measure the strength of IL-2 signaling using, e.g., flow cytometry analysis. The reporter construct was retrovirally transduced into the display cell line AK-D10 generated above.

Similar reporter constructs were also introduced into other display cells such as LOT-D08 cells and LOT-D08 cells expressing chiCD8α$^{flox}$ and chiCD8β$^{flox}$ generated above.

1) Generation of AK-D10 Cells Comprising an IL-2 Reporter Construct

A study was first conducted to examine the feasibility of using IL-2 production as a functional readout of T cell activation. Briefly, AK-D10 cells or AK-D10 cells expressing the chimeric TCR C58 were stimulated using anti-CD3 antibody or an anti-CD3/anti-CD28 antibody cocktail and then examined for activation by measuring IL-2 production. Anti-CD3 antibody (eBioscience, Cat. No.: 16-0032) or anti-CD3 and anti-CD28 (eBioscience, Cat. No.: 16-0281) antibodies were coated on a 96-well plate at a concentration of 5 µg/ml and incubated for 3 hours at 37° C. Subsequently, $1 \times 10^5$ cells resuspended in 200 µl of SF-IMDM were added to each well and incubated for 24 hours at 37° C. and 10% $CO_2$. IL-2 production in the culture supernatant of activated AK-D10 cells with or without C58 expression was examined using a mouse IL-2 ELISA kit (eBioscience, Cat. No.: 88-7024).

Figure 5:
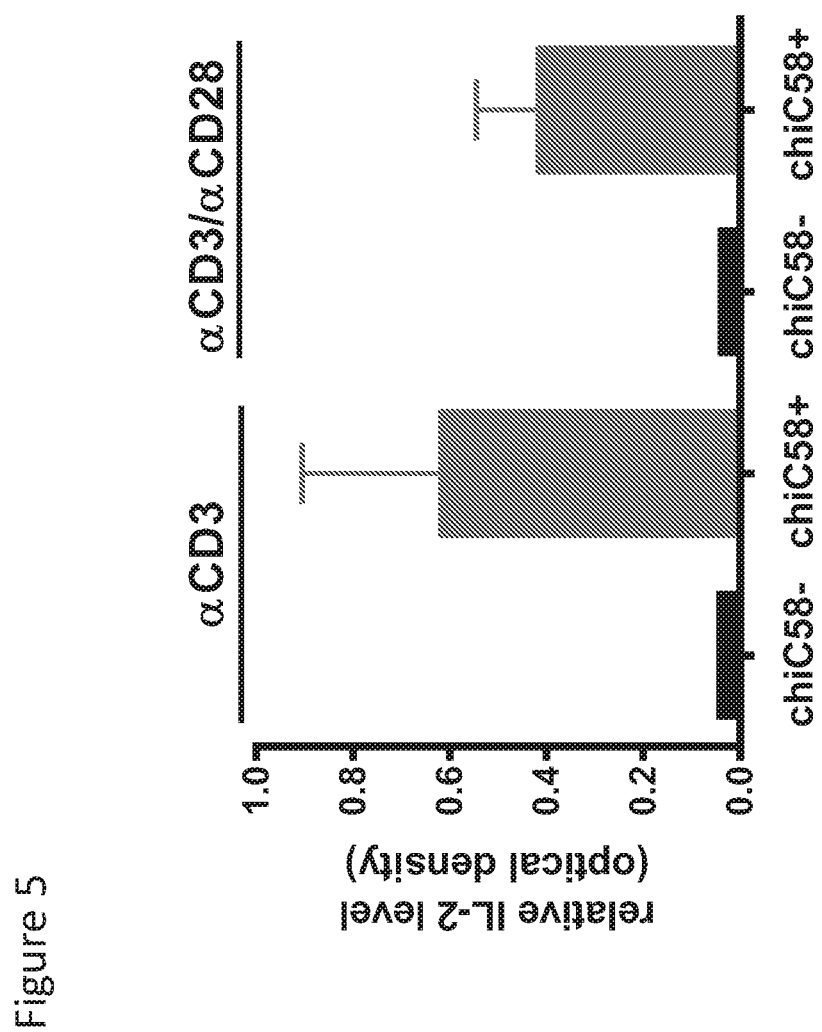
FIG. 5 is a bar graph showing relative IL-2 levels in culture supernatant produced by AK-D10 cells (marked as "chiC58−") or AK-D10 cells expressing both a reporter construct and chimeric TCR C58 (marked as "chiC58+") after incubation with either anti-CD3 antibody (left) or anti-CD3 and anti-CD28 antibodies (right), measured by ELISA. The y axis shows optical density (OD) signal.

Under anti-CD3 or anti-CD3/anti-CD28 antibody stimulation, only AK-D10 cells expressing the chimeric TCR C58, but not AK-D10 cells that lacked TCR expression, secreted IL-2 (FIG. 5).

After establishing that IL-2 production could serve as a useful functional readout of T cell activation, AK-D10 cells were transduced to express IL-2-EGFP reporter constructs, which provided a surrogate readout of IL-2 production. Three reporter constructs were generated, in which a minimal IL-2 promoter, an IL-2 promoter comprising three NFAT binding sites, or an IL-2 promoter comprising six NFAT binding sites was operably linked to a nucleotide sequence encoding EGFP (mIL-2-EGFP, IL-2-$(NFAT)_3$-EGFP, and IL-2-$(NFAT)_6$-EGFP, respectively). The reporter constructs comprised a hygromycin B resistance gene as a selection marker. The reporter construct genes were each packaged separately into replication-incompetent retroviral particles. HEK 293 cells (ATCC) were co-transfected with three different vectors: a pVPack vector encoding gag-pol genes (pVPack vector system, Stratagene), a vector encoding the PVC 211 env gene, and a retroviral vector encoding one of the three reporter constructs. Transfection was performed using FuGENE 6 Transfection Reagent (Roche Applied Science) according to the manufacturer's instructions. The resulting retroviral supernatant was harvested three days later and used directly to transduce AK-D10 cells generated above. The AK-D10 cells expressing the reporter constructs were selected using hygromycin B antibiotic at a working concentration of 800 µg/ml. After a selection time of 4 days, single T cells from a population of hygromycin-resistant AK-D10 cells were sorted in 96-well plates. These single T cells grew into T cell clones in about one week. Subsequently, these single cell clones were transduced with a TCR, activated with a cognate peptide-MHC complex or anti-CD3 antibody, and analyzed by flow cytometry to confirm that the reporter gene was turned on as evidenced by EGFP expression.

2) Activation of AK-D10 Cells Comprising an IL-2 Reporter Construct Using Anti-CD3 Antibody In this example, AK-D10 cells expressing an IL-2-$(NFAT)_3$-EGFP reporter construct and the chimeric TCR DMF4 (AK-D10 IL-2-$(NFAT)_3$-EGFP+ chiDMF4+) were activated in the presence or absence of plate-bound anti-CD3 antibody as described above and then EGFP expression was examined using flow cytometry. All flow cytometry data were analyzed using the FlowJo software (Treestar). AK-D10 cells expressing only the IL-2 reporter construct but not recombinant TCR were used as a negative control.

Figure 6A:
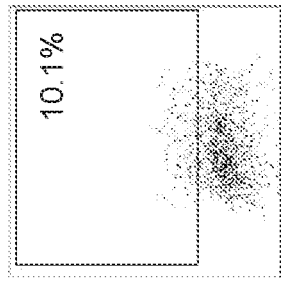
FIGS. 6A, 6B, and 6C are a set of flow cytometry plots showing EGFP expression. The cells tested are AK-D10 cells expressing an IL-2 reporter construct and chimeric TCR DMF4 (AK-D10 IL-2-(NFAT)$_3$-EGFP+ chiDMF4+) incubated in the presence (FIG. 6A) or absence (FIG. 6B) of anti-CD3 antibody or AK-D10 cells expressing only the IL-2 reporter construct (AK-D10 IL-2-(NFAT)$_3$-EGFP+) incubated with anti-CD3 antibody (FIG. 6C). The percentage of EGFP positive cells is indicated in each plot.
Figure 6B:
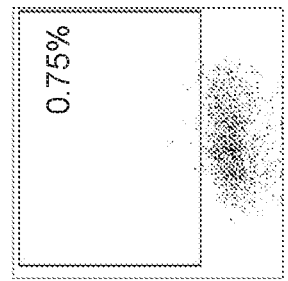
Figure 6C:
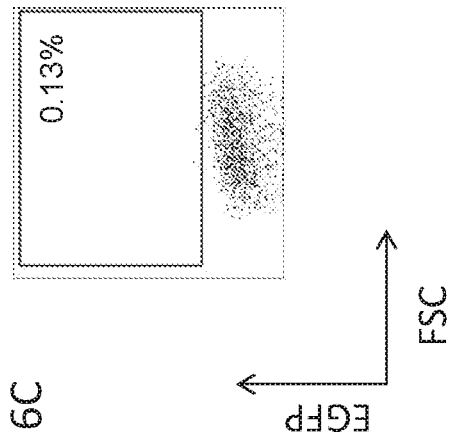
Figure 7A:
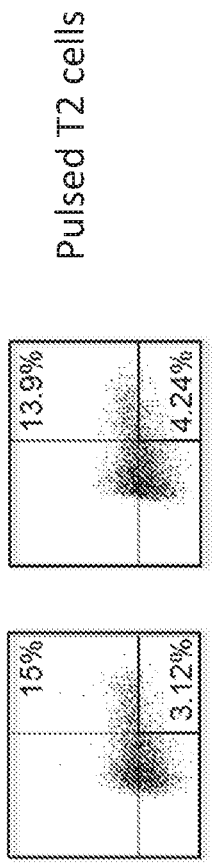
FIGS. 7A, 7B, and 7C are a set of flow cytometry plots from an assay in which AK-D10 cells expressing an IL-2 reporter construct and chimeric TCR C259 (AK-D10 IL-2-(NFAT)$_3$-EGFP+ chiC259+) were incubated with T2 cells pulsed with a NY-ESO-1 peptide SLLMWITQV (SEQ ID NO: 31) (FIG. 7A), incubated with non-pulsed T2 cells (FIG. 7B), or incubated in the absence of T2 cells (FIG. 7C) and measured for TCR and EGFP expression using flow cytometry. The percentage of TCR$^{high}$ EGFP+ cells is indicated in the upper right panel of each plot. The percentage of TCR$^{low}$ EGFP+ cells is indicated in the lower right panel of each plot.
Figure 7B:
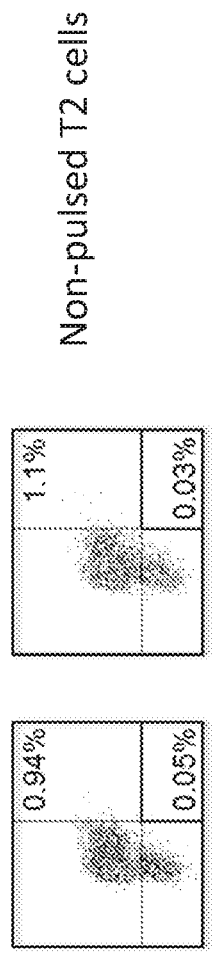
Figure 7C:
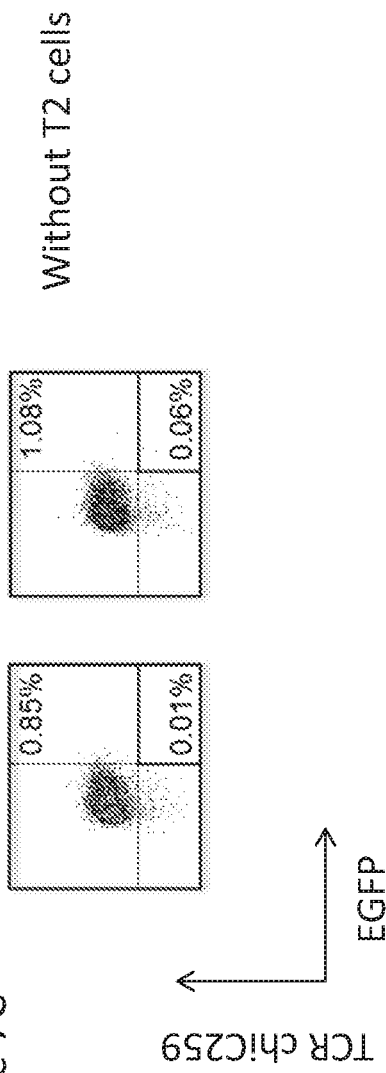

Activation of the IL-2 reporter construct, as evidenced by EGFP expression, was only observed in DMF4-expressing cells co-cultured with anti-CD3 antibody (FIG. 6A). In the absence of the anti-CD3 antibody (FIG. 6B), or in the absence of TCR expression (FIG. 6C), minimal reporter activation was detected.

3) Activation of AK-D10 Cells or BB8 Cells Comprising an IL-2 Reporter Construct Using T2 Cells Pulsed with Peptides Next, a series of studies were conducted to examine activation of AK-D10 cells or BB8 cells expressing an IL-2 reporter construct and a recombinant TCR by peptide-pulsed T2 cells.

In a first study, two NY-ESO-1 specific TCRs were tested: C58, which has been described above, and C259, which is a TCR specific for a peptide derived from NY-ESO-1 in the context of HLA-A*0201. See, e.g., Rapoport et al., Nat Med. 2015, 21(8): 914-921; Robbins et al., J Clin Oncol. 2011, 29(7): 917-924; Robbins et al., J Immunol. 2008, 180(9): 6116-6131; and U.S. Pat. No. 8,008,438, each of which is herein incorporated by reference in its entirety. C259 was expressed as a chimeric TCR with human variable regions fused to murine non-variable regions to ensure proper anchoring and interaction with murine CD3 and proper triggering of murine signaling pathways. The α and β chains of chimeric C259 comprise the amino acid sequences of SEQ ID NOs: 35 and 36, respectively.

T2 cells ($1.0 \times 10^6$ cells in 200 µl PBS) were pulsed with 50 µg/ml NY-ESO-1 antigen peptide SLLMWITQV (SEQ ID NO: 31) (IBA Lifesciences, Cat. No.: 6-7013-901) for 3 hours at 37° C. Next, $5.0 \times 10^4$ AK-D10 cells transduced to express an L-2 reporter construct and chimeric TCR C58 (AK-D10 IL-2-$(NFAT)_3$-EGFP+ chiC58+) or chimeric TCR C259 (AK-D10 IL-2-$(NFAT)_3$-EGFP+ chiC259+) were co-incubated with $5.0 \times 10^4$ pulsed T2 cells in 200 µl SF-IMDM media for 16 hours at 37° C. and 10% $CO_2$. As controls, AK-D10 derivatives were also incubated with non-pulsed T2 cells or incubated in the absence of T2 cells. After incubation, cells were stained for TCR expression using anti-mouse TCRβ antibody (BD Biosciences, Cat. No.: 553174). To assess expression of T cell activation markers CD69 and CD137, cells were stained using anti-mouse CD69-BV421 (Biolegend, Cat. No.: 104528) and anti-mouse CD137-APC (eBioscience, Cat. No.: 17-1371). Cells were then subjected to flow cytometry analysis. TCR positive cells were gated and the percentage of TCR+ EGFP+, TCR+CD69+, and TCR+CD137+ cells was determined using the FlowJo software (Treestar).

Figure 8:
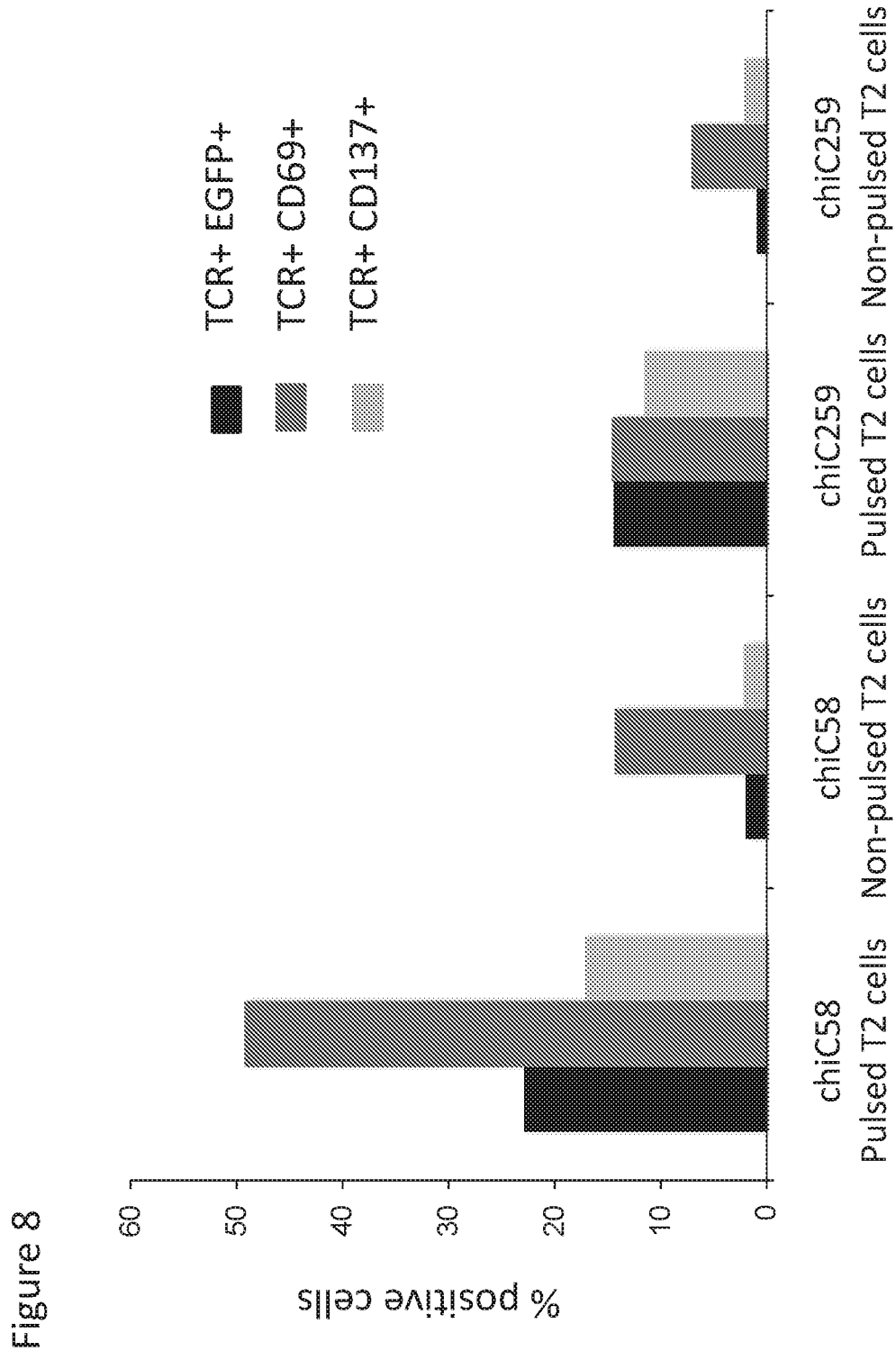
FIG. 8 is a bar graph showing results from an assay in which AK-D10 cells expressing a reporter construct IL-2-(NFAT)$_3$-EGFP and chimeric TCR C58 (marked as "chiC58") or C259 (marked as "chiC259") were co-cultured with T2 cells pulsed with a NY-ESO-1 peptide SLLMWITQV (SEQ ID NO: 31) or co-cultured with non-pulsed T2 cells and analyzed for the expression of TCR, EGFP, CD69, and CD137 using flow cytometry. The percentage (%) of TCR+ EGFP+ cells, TCR+CD69+ cells, or TCR+ CD137+ cells is shown.

Co-incubation with T2 cells pulsed with cognate peptides enhanced activation of the IL-2 reporter construct as evidenced by EGFP expression (FIGS. 7A-7C and FIG. 8). Consistently, co-culture with pulsed T2 cells also upregulated expression of T cell activation markers CD69 and CD137 (FIG. 8). Notably, surface TCR expression was down-regulated upon activation (FIGS. 7A-7C), highlighting that the IL-2 reporter assay developed here may be particularly useful in identifying TCRs with superior signaling capability. A binding based screening, e.g., using MHC tetramers, may be less informative if enhanced tetramer binding is more than offset by down-regulated surface TCR expression.

In a second study, the sensitivity of the IL-2-EGFP reporter construct was examined using T2 cells pulsed with a dose titration of cognate peptides. Briefly, $22.0 \times 10^6$ T2 cells were pulsed with a Mart-1 antigen peptide ELA-GIGILTV (SEQ ID NO: 30) (P&E, Cat. No.: EP04197) ranging from 0.125 µM to 256 µM for 3 hours at 37° C. For peptide pulsing, a negative control peptide ILLWQPIPV (SEQ ID NO: 34) (Genscript, custom order) was added to maintain a constant total peptide concentration of 512 µM. Subsequently, $5.0 \times 10^4$ AK-D10 cells transduced to express an IL-2 reporter construct and chimeric TCR DMF4 (AK-D10 IL-2-(NFAT)$_3$-EGFP+ chiDMF4+) or chimeric TCR DMF5 (AK-D10 IL-2-(NFAT)$_3$-EGFP+ chiDMF5+) were co-incubated with $5.0 \times 10^4$ pulsed T2 cells in 200 µl SF-IMDM media for 12 hours at 37° C. and 10% $CO_2$. Cells were stained for TCR expression using anti-human TCRα/β-APC (BD Biosciences, Cat. No.: 563826) and analyzed by flow cytometry. TCR positive cells were gated and the percentage of TCR+ EGFP+ cells was determined using the FlowJo software (Treestar).

Figure 9A:
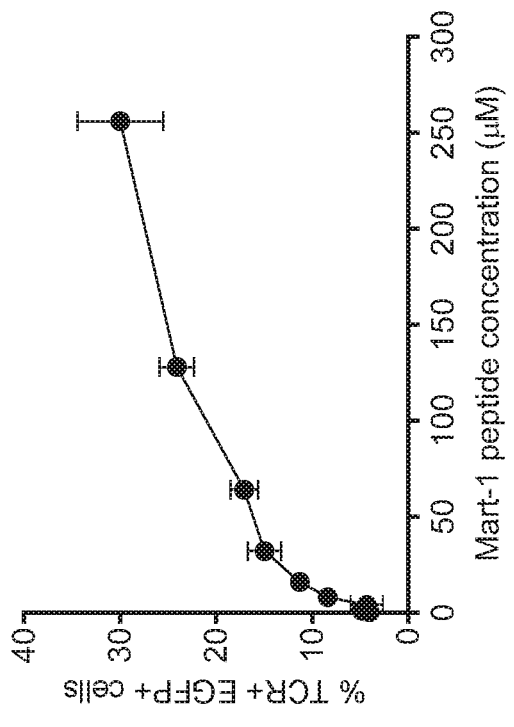
FIGS. 9A and 9B are graphs showing results from an assay in which AK-D10 cells expressing a reporter construct IL-2-(NFAT)$_3$-EGFP and chimeric TCR DMF4 (marked as "chiDMF4", FIG. 9A) or DMF5 (marked as "chiDMF5", FIG. 9B) were co-cultured with T2 cells pulsed with various concentrations of a Mart-1 peptide ELAGIGILTV (SEQ ID NO: 30) and measured for TCR and EGFP expression using flow cytometry. The percentage (%) of TCR+ EGFP+ cells is plotted against concentrations of the Mart-1 peptide.
Figure 9B:
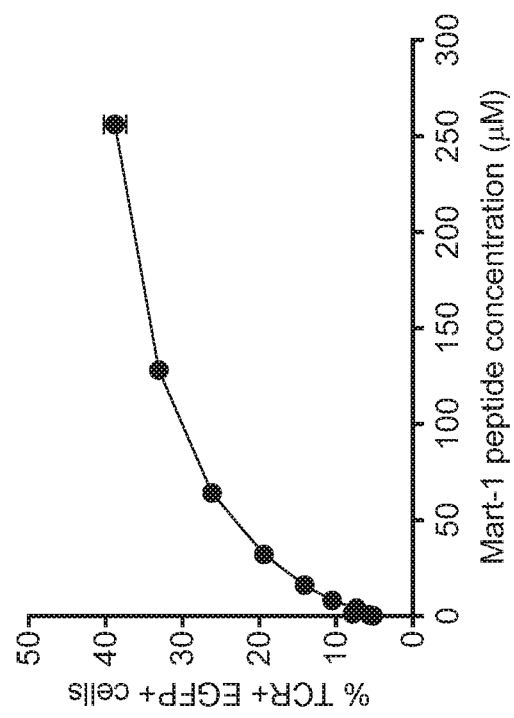

As shown in FIGS. 9A and 9B, T2 cells pulsed with cognate peptides activated the IL-2-EGFP reporter construct in a dose-dependent manner.

A third study looked at how activation of the IL-2-EGFP reporter construct was influenced by factors such as peptide concentrations used to pulse T2 cells, lengths of activation, and the presence or absence of CD8. T2 cells ($5.0 \times 10^5$ cells in 200 µl PBS) were pulsed with 50 µg/ml, 5 µg/ml, or 0.5 µg/ml of a Mart-1 antigen peptide ELAGIGILTV (SEQ ID NO: 30) (P&E, Cat. No.: EP04197) for 3 hours at 37° C. BB8 cells (MTCD8 mCD8αβ-chiCD8α$^{flox}$+ chiCD8β$^{flox}$+ IL-2-(NFAT)$_3$-EGFP+) expressing chimeric TCR DMF4 or DMF5 were transduced to express a Cre recombinase or were not transduced. Next, $5.0 \times 10^4$ BB8 derivatives were co-incubated with $5.0 \times 10^4$ pulsed T2 cells in 200 µl SF-IMDM media at 37° C. and 10% $CO_2$ over a time course of 0-25 hours. Cells were then stained for TCR and CD8 using anti-mouse TCRβ-APC (BD Biosciences, Cat. No.: 553174) and anti-human CD8-PE (BD Biosciences, Cat. No.: 555635) and analyzed by flow cytometry. TCR positive cells were gated and the percentage of TCR+ EGFP+ cells was determined using the FlowJo software (Treestar).

Figure 10A:
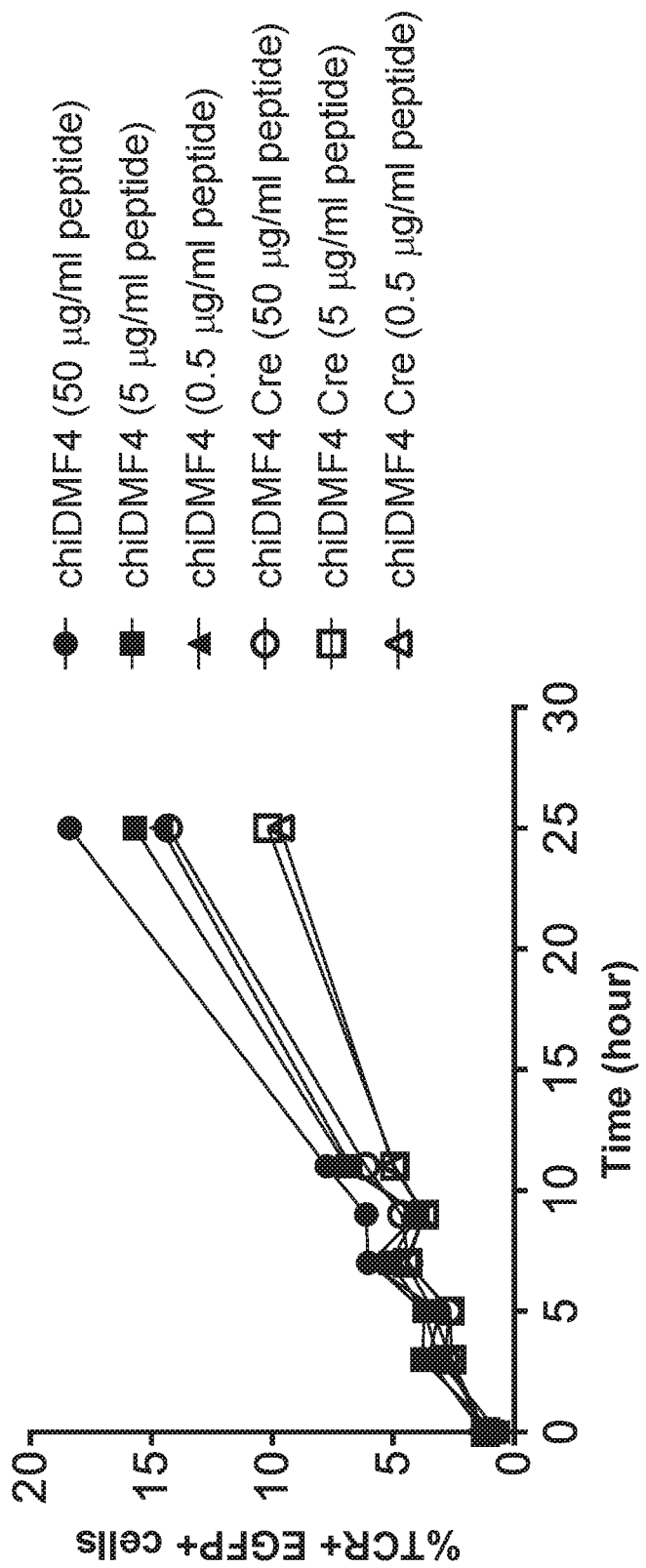
FIGS. 10A and 10B are graphs showing results from an assay in which BB8 cells expressing chimeric TCR DMF4 or DMF5 were transduced to express a Cre recombinase (marked as "chiDMF4 Cre" in FIG. 10A and "chiDMF5 Cre" in FIG. 10B) or not transduced (marked as "chiDMF4" in FIG. 10A and "chiDMF5" in FIG. 10B). The cells were then co-cultured with T2 cells pulsed with 50 μg/ml, 5 μg/ml, or 0.5 μg/ml of a Mart-1 peptide ELAGIGILTV (SEQ ID NO: 30) and measured for TCR, CD8, and EGFP expression using flow cytometry. The percentage (%) of TCR+ EGFP+ cells is plotted against lengths of activation.
Figure 10B:
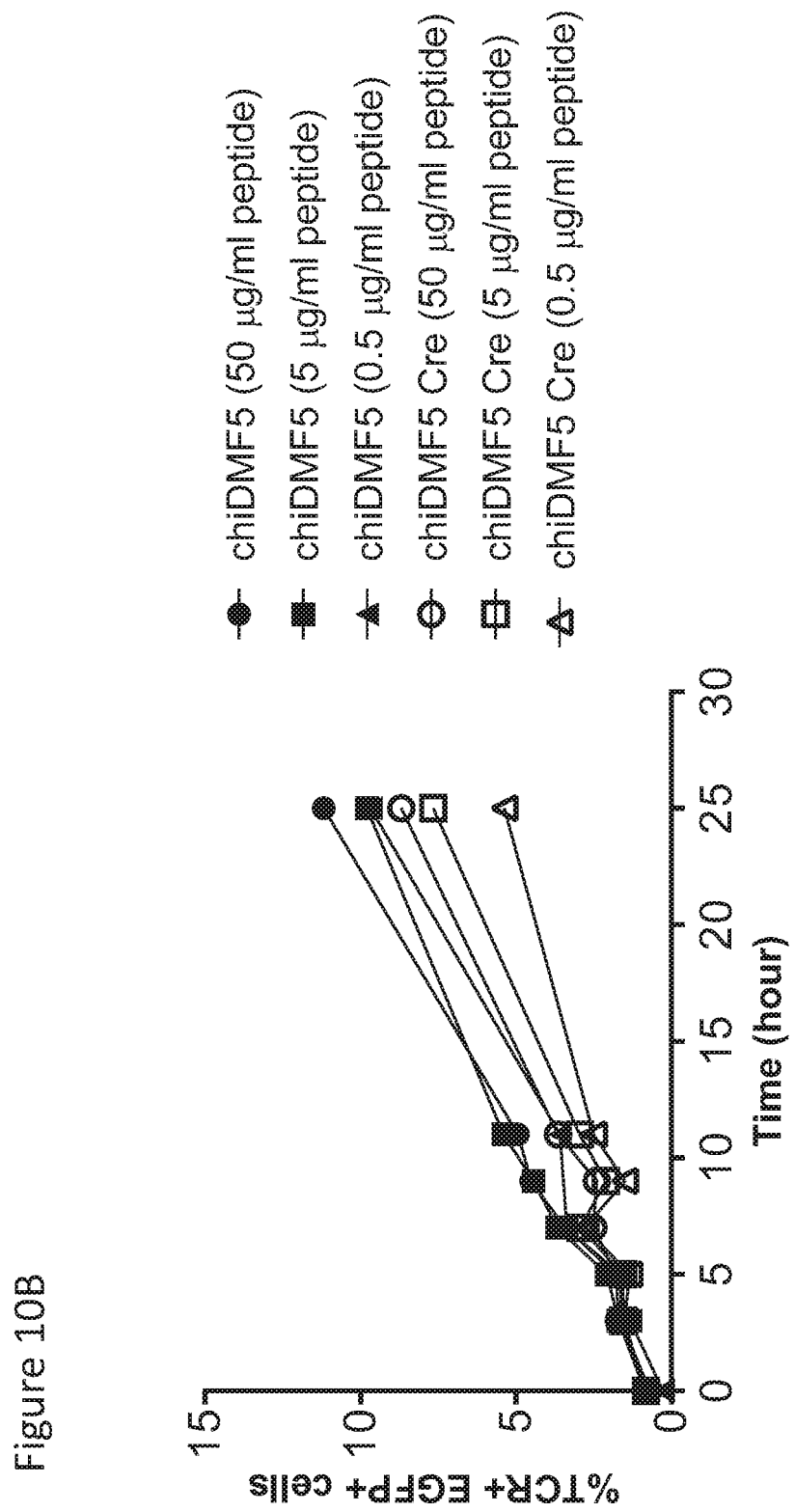

As shown in FIGS. 10A and 10B, activation of the IL-2-EGFP reporter construct is a function of time within the measured duration. The extent of activation increased as T2 cells were pulsed with increasing concentrations of cognate peptides. CD8 staining confirmed that transduction of the Cre recombinase successfully depleted surface CD8 expression (data not shown), which decreased Il-2 signaling activation induced by peptide-pulsed T2 cells.

Example 6: Isolating TCRs from Human Donors

In this example, T cells from human subjects were screened for TCRs specific for a target of interest. More specifically, TCRs specific for HPV E6 or E7 derived peptides were isolated from human donors. T cells from humans who have been vaccinated against E6 or E7 can also be used to isolate TCRs specific for E6 or E7 derived peptides.

1) Isolating TCRs from In Vitro Stimulated Human T Cells

Human T cells were isolated from PBMCs using standard methods. In order to identify TCRs specific for HPV E6 or E7 derived peptides, isolated T cells were activated with (i) autologous dendritic cells loaded with a peptide pool PepMix™ HPV 16 (protein E6 or E7) from JPT peptides, (ii) T2 cells loaded with HLA-A2 restricted peptides derived from HPV E6 or E7, or (iii) peptide-MHC complexes (DimerX loaded with E6 or E7 derived peptides). In the latter two cases, the E6-derived peptide KLPQLCTEL (SEQ ID NO: 31) and the E7-derived peptide GTLGIVCPI (SEQ ID NO: 32) were used to load T2 cells and DimerX. Alternatively, isolated T cells can also be activated using antigen-presenting cells transfected with in vitro-transcribed (IVT) RNA encoding the antigens of interest.

Subsequently, the activated cells were harvested, stained with a fluorescent-conjugated anti-IFNγ antibody (Secretion Assay Kit, Miltenyi Biotec) as well as a T cell specific antibody (anti-CD8 or anti-CD4 antibody), and bulk sorted or single cell sorted for cells that were double positive for IFNγ/CD8 or IFNγ/CD4. Sorting was conducted using a BD FACSAria flow cytometer (BD Biosciences). Alternatively, the activated cells can also be stained using anti-IL-2 antibody together with anti-CD8 or anti-CD4 antibody, and then sorted for IL-2/CD8 or IL-2/CD4 double positive cells.

Bulk or single cell sorted activated T cells are expanded using, e.g., recombinant IL-2, anti-CD3/anti-CD28 antibodies, or the cognate peptide-MHC complexes. TCR α and β chains are cloned directly from single cell sorted or bulk sorted antigen-specific CD8+ or CD4+T lymphocytes. The cloned TCRs are directly tested in functional assays or used for library generation.

2) Isolating TCRs from T Cells Sorted Using Peptide-MHC Complexes of Interest

Human T cells were isolated from PBMCs using standard methods. Isolated T cells were stained using DimerX loaded with an E6-derived peptide KLPQLCTEL (SEQ ID NO: 31) or an E7-derived peptide GTLGIVCPI (SEQ ID NO: 32) and bulk or single cell sorted using a BD FACSAria flow cytometer (BD Biosciences). No activation of T cells was conducted.

Bulk or single cell sorted T cells are expanded using, e.g., recombinant IL-2, anti-CD3/anti-CD28 antibodies, or the specific peptide-MHC complex used in sorting. TCR α and β chains are cloned directly from single cell sorted or bulk sorted antigen-specific CD8+ or CD4+T lymphocytes. The cloned TCRs are directly tested in functional assays or used for library generation.

TABLE 1

Amino acid sequences of exemplary co-receptors, TCRs, MHCs and peptide antigens

| SEQ ID NO: | Description (protein sequences unless otherwise indicated) | Sequence |
|---|---|---|
| 1 | Chimeric CD8α | SQFRVSPLDRTWNLGETVELKCQVLLSNPTSGCSWLFQPRGAAASP TFLLYLSQNKPKAAEGLDTQRFSGKRLGDTFVLTLSDFRRENEGYY FCSALSNSIMYFSHFVPVFLPAKPTTTPAPRPPTPAPTIASQPLSL RPEACRPAAGGAVHTRGLDFACDIWAPLAGICVALLLSLIITLICY HRSRKRVCKCPRPLVRQEGKPRPSEKIV |

TABLE 1-continued

Amino acid sequences of exemplary co-receptors, TCRs, MHCs and peptide antigens

| SEQ ID NO: | Description (protein sequences unless otherwise indicated) | Sequence |
|---|---|---|
| 2 | Chimeric CD8β | LQQTPAYIKVQTNKMVMLSCEAKISLSNMRIYWLRQRQAPSSDSHH EFLALWDSAKGTIHGEEVEQEKIAVFRDASRFILNLTSVKPEDSGI YFCMIVGSPELTFGKGTQLSVVDFLPTTAQPTKKSTLKKRVCRLPR PETQKGPLCSPLSLLVVCILLLLAFLGVAVYFYCVRRRARIHFMKQ FHK |
| 3 | Chimeric CD8α with loxp sites (nucleotide sequence) | AGCCAGTTCAGAGTGTCCCCCCTGGACAGAACCTGGAACCTGGGCG AGACAGTGGAACTGAAGTGCCAGGTGCTGCTGAGCAACCCCACCAG CGGCTGTAGCTGGCTGTTCCAGCCTAGAGGCGCCGCTGCCAGCCCT ACCTTTCTGCTGTACCTGAGCCAGAACAAGCCCAAGGCCGCCGAGG GCCTGGACACCCAGAGATTCAGCGGCAAGAGACTGGGCGACACCTT CGTGCTGACCCTGAGCGACTTCAGAAGAGAGAACGAGGGCTACTAC TTCTGCAGCGCCCTGAGCAACAGCATCATGTACTTCAGCCACTTCG TGCCCGTGTTTCTGCCCGCCAAGCCTACCACAACCCCTGCCCCTAG ACCTCCTACCCCAGCCCCTACAATCGCCAGCCAGCCTCTGTCTCTG AGGCCCGAGGCTTGTAGACCAGCTGCTGGCGGAGCCGTGCACACAA GAGGCCTGGACTTCGCCTGCGACATAACTTCGTATAGCATACATTA TACGAAGTTATCTATCTGGGCTCCACTGGCCGGCATTTGTGTGGCA CTGCTGCTGTCCCTGATCATCACCCTGATCTGCTACCACAGATCCC GGAAGCGCGTGTGCAAGTGCCCTAGACCACTCGTGCGGCAGGAAGG CAAGCCCAGACCCAGCGAGAAGATTGTCTGAATAACTTCGTATAGC ATACATTATACGAAGTTAT |
| 4 | Chimeric CD8β with loxp sites (nucleotide sequence) | CTGCAGCAGACCCCCGCCTACATCAAGGTGCAGACCAACAAGATGG TCATGCTGAGCTGCGAGGCCAAGATCAGCCTGAGCAACATGAGAAT CTACTGGCTGAGACAGAGACAGGCCCCCAGCAGCGACAGCCACCAC GAGTTTCTGGCCCTGTGGGACAGCGCCAAGGGCACCATCCATGGCG AGGAAGTGGAACAGGAAAAGATCGCCGTGTTCAGGGACGCCAGCAG ATTCATCCTGAACCTGACCAGCGTGAAGCCCGAGGACAGCGGAATC TACTTCTGCATGATCGTGGGCAGCCCCGAGCTGACCTTCGGCAAGG GAACACAGCTGAGCGTGGTGGACTTCCTGCCTACCACCGCCCAGCC CACCAAGAAGTCTACCCTGAAGAAAAGAGTGTGCAGACTGCCCAGA CCCGAGACACAGAAAGGCCCTCTGTGCAGCCCTATAACTTCGTATA GCATACATTATACGAAGTTATCTCTGAGCCTGCTGGTCGTGTGCAT CCTCCTGCTGCTGGCTTTTCTGGGCGTGGCCGTGTACTTCTACTGC GTGCGGAGAAGGGCCAGGATCCACTTTATGAAGCAGTTCCACAAAT GAATAACTTCGTATAGCATACATTATACGAAGTTAT |
| 5 | Chimeric CD8α with loxp sites (amino acid sequence) | SQFRVSPLDRTWNLGETVELKCQVLLSNPTSGCSWLFQPRGAAASP TFLLYLSQNKPKAAEGLDTQRFSGKRLGDTFVLTLSDFRRENEGYY FCSALSNSIMYFSHFVPVFLPAKPTTTPAPRPPTPAPTIASQPLSL RPEACRPAAGGAVHTRGLDFACDITSYSIHYTKLSIWAPLAGICVA LLLSLIITLICYHRSRKRVCKCPRPLVRQEGKPRPSEKIV |
| 6 | Chimeric CD8β with loxp sites (amino acid sequence) | LQQTPAYIKVQTNKMVMLSCEAKISLSNMRIYWLRQRQAPSSDSHH EFLALWDSAKGTIHGEEVEQEKIAVFRDASRFILNLTSVKPEDSGI YFCMIVGSPELTFGKGTQLSVVDFLPTTAQPTKKSTLKKRVCRLPR PETQKGPLCSPITSYSIHYTKLSLSLLVVCILLLLAFLGVAVYFYC VRRRARIHFMKQFHK |
| 7 | Chimeric C58 α chain | KQEVTQIPAALSVPEGENLVLNCSFTDSAIYNLQWFRQDPGKGLTS LLLITPWQREQTSGRLNASLDKSSGRSTLYIAASQPGDSATYLCAV RPLLDGTYIPTFGRGTSLIVHPYIQNPEPAVYQLKDPRSQDSTLCL FTDPDSQINVPKTMESGTFITDKTVLDMKAMDSKSNGAIAWSNQTS FTCQDIFKETNATYPSSDVPCDATLTEKSFETDMNLNFQNLSVMGL RILLLKVAGFNLLMTLRLWSS |
| 8 | Chimeric C58 β chain | NAGVTQTPKFQVLKTGQSMTLQCAQDMNHEYMSWYRQDPGMGLRLI HYSVAIQTTDQGEVPNGYNVSRSTIEDFPLRLLSAAPSQTSVYFCA SSYLGNTGELFFGEGSRLTVLEDLRNVTPPKVSLFEPSKAEIANKQ KATLVCLARGFFPDHVELSWWVNGKEVHSGVSTDPQAYKESNYSYC LSSRLRVSATFWHNPRNHFRCQVQFHGLSEEDKWPEGSPKPVTQNI SAEAWGRADCGITSASYHQGVLSATILYEILLGKATLYAVLVSGLV LMAMVKKNS |
| 9 | Chimeric DMF4 α chain | GQQLNQSPQSMFIQEGEDVSMNCTSSSIFNTWLWYKQDPGEGPVLL IALYKAGELTSNGRLTAQFGITRKDSFLNISASIPSDVGIYFCAGG TGNQFYFGTGTSLTVIPYIQNPEPAVYQLKDPRSQDSTLCLFTDFD SQINVPKTMESGTFITDKTVLDMKAMDSKSNGAIAWSNQTSFTCQD IFKETNATYPSSDVPCDATLTEKSFETDMNLNFQNLSVMGLRILLL KVAGFNLLMTLRLWSS |

TABLE 1-continued

Amino acid sequences of exemplary co-receptors, TCRs, MHCs and peptide antigens

| SEQ ID NO: | Description (protein sequences unless otherwise indicated) | Sequence |
| --- | --- | --- |
| 10 | Chimeric DMF4 β chain | DAGITQSPRHKVTETGTPVTLRCHQTENHRYMYWYRQDPGHGLRLI HYSYGVKDTDKGEVSDGYSVSRSKTEDFLLTLESATSSQTSVYFCA ISEVGVGQPQHFGDGTRLSILEDLRNVTPPKVSLFEPSKAEIANKQ KATLVCLARGFFPDHVELSWWVNGKEVHSGVSTDPQAYKESNYSYC LSSRLRVSATFWHNPRNHFRCQVQFHGLSEEDKWPEGSPKPVTQNI SAEAWGRADCGITSASYQQGVLSATILYEILLGKATLYAVLVSTLV VMAMVKRKNS |
| 11 | Chimeric DMF5 α chain | QKEVEQNSGPLSVPEGAIASLNCTYSDRGSQSFFWYRQYSGKSPEL IMFIYSNGDKEDGRETAQLNKASQYVSLLIRDSQPSDSATYLCAVN FGGGKLIFGQGTELSVKPYIQNPEPAVYQLKDPRSQDSTLCLFTDF DSQINVPKTMESGTFITDKTVLDMKAMDSKSNGAIAWSNQTSFTCQ DIFKETNATYPSSDVPCDATLTEKSFETDMNLNFQNLSVMGLRILL LKVAGFNLLMTLRLWSS |
| 12 | Chimeric DMF5 β chain | IAGITQAPTSQILAAGRRMTLRCTQDMRHNAMYWYRQDLGLGLRLI HYSNTAGTTGKGEVPDGYSVSRANTDDFPLTLASAVPSQTSVYFCA SSLSFGTEAFFGQGTRLTVVEDLRNVTPPKVSLFEPSKAEIANKQK ATLVCLARGFFPDHVELSWWVNGKEVHSGVSTDPQAYKESNYSYCL SSRLRVSATFWHNPRNHFRCQVQFHGLSEEDKWPEGSPKPVTQNIS AEAWGRADCGITSASYQQGVLSATILYEILLGKATLYAVLVSTLVV MAMVKRKNS |
| 13 | Mouse TCR α chain non-variable region (A0A075B662) | XIQNPEPAVYQLKDPRSQDSTLCLFTDFDSQINVPKTMESGTFITD KTVLDMKAMDSKSNGAIAWSNQTSFTCQDIFKETNATYPSSDVPCD ATLTEKSFETDMNLNFQNLSVMGLRILLLKVAGFNLLMTLRLWSS X can be any amino acid |
| 14 | Mouse TCR α chain transmembrane and cytoplasmic regions | SVMGLRILLLKVAGFNLLMTLRLWSS |
| 15 | Mouse TCR β chain non-variable region (Trbc1) (A0A0A6YWV4) | XDLRNVTPPKVSLFEPSKAEIANKQKATLVCLARGFFPDHVELSWW VNGKEVHSGVSTDPQAYKESNYSYCLSSRLRVSATFWHNPRNHFRC QVQFHGLSEEDKWPEGSPKPVTQNISAEAWGRADCGITSASYQQGV LSATILYEILLGKATLYAVLVSTLVVMAMVKRKNS X can be any amino acid |
| 16 | Mouse TCR β chain (Trbc1) transmembrane and cytoplasmic regions | EILLGKATLYAVLVSTLVVMAMVKRKNS |
| 17 | Mouse TCR β chain non-variable region (Trbc1) (A0A075B5J3) | XDLRNVTPPKVSLFEPSKAEIANKQKATLVCLARGFFPDHVELSWW VNGKEVHSGVSTDPQAYKESNYSYCLSSRLRVSATFWHNPRNHFRC QVQFHGLSEEDKWPEGSPKPVTQNISAEAWGRADCGITSASYQQGV LSATILYEILLGKATLYAVLVSTLVVMAMVRNR X can be any amino acid |
| 18 | Mouse TCR β chain (Trbc1) transmembrane and cytoplasmic regions | EILLGKATLYAVLVSTLVVMAMVRNR |
| 19 | Mouse TCR β chain non-variable region (Trbc2) (A0A075B5J4) | XDLRNVTPPKVSLFEPSKAEIANKQKATLVCLARGFFPDHVELSWW VNGKEVHSGVSTDPQAYKESNYSYCLSSRLRVSATFWHNPRNHFRC QVQFHGLSEEDKWPEGSPKPVTQNISAEAWGRADCGITSASYHQGV LSATILYEILLGKATLYAVLVSGLVLMAMVKKKNS X can be any amino acid |
| 20 | Mouse TCR β chain (Trbc2) transmembrane and cytoplasmic regions | EILLGKATLYAVLVSGLVLMAMVKKKNS |
| 21 | Mouse CD8α isoform 1 | KPQAPELRIFPKKMDAELGQKVDLVCEVLGSVSQGCSWLFQNSSSK LPQPTFVVYMASSHNKITWDEKLNSSKLFSAMRDTNNKYVLTLNKF SKENEGYYFCSVISNSVMYFSSVVPVLQKVNSTTTKPVLRTPSPVH PTGTSQPQRPEDCRPRGSVKGTGLDFACDIYIWAPLAGICVALLLS LIITLICYHRSRKRVCKCPRPLVRQEGKPRPSEKIV |

TABLE 1-continued

Amino acid sequences of exemplary co-receptors, TCRs, MHCs and peptide antigens

| SEQ ID NO: | Description (protein sequences unless otherwise indicated) | Sequence |
|---|---|---|
| 22 | Mouse CD8β | LIQTPSSLLVQTNHTAKMSCEVKSISKLTSIYWLRERQDPKDKYFE FLASWSSSKGVLYGESVDKKRNIILESSDSRRPFLSIMNVKPEDSD FYFCATVGSPKMVFGTGTKLTVVDVLPTTAPTKKTTLKMKKKQCP FPHPETQKGLTCSLTTLSLLVVCILLLLAFLGVAVYFYCVRRRARI HFMKQFHK |
| 23 | Human CD8α isoform 1 | SQFRVSPLDRTWNLGETVELKCQVLLSNPTSGCSWLFQPRGAAASP TFLLYLSQNKPKAAEGLDTQRFSGKRLGDTFVLTLSDERRENEGYY FCSALSNSIMYFSHFVPVFLPAKPTTTPAPRPPTPAPTIASQPLSL RPEACRPAAGGAVHTRGLDFACDIYIWAPLAGTCGVLLLSLVITLY CNHRNRRRVCKCPRPVVKSGDKPSLSARYV |
| 24 | Human CD8β isoform 1 | LQQTPAYIKVQTNKMVMLSCEAKISLSNMRIYWLRQRQAPSSDSHH EFLALWDSAKGTIHGEEVEQEKIAVFRDASRFILNLTSVKPEDSGI YFCMIVGSPELTFGKGTQLSVVDFLPTTAQPTKKSTLKKRVCRLPR PETQKGPLCSPITLGLLVAGVLVLLVSLGVAIHLCCRRRRARLRFM KQFYK |
| 25 | Chimeric CD8α with loxp sites (amino acid sequence) | SQFRVSPLDRTWNLGETVELKCQVLLSNPTSGCSWLFQPRGAAASP TFLLYLSQNKPKAAEGLDTQRFSGKRLGDTFVLTLSDERRENEGYY FCSALSNSIMYFSHFVPVFLPAKPTTTPAPRPPTPAPTIASQPLSL RPEACRPAAGGAVHTRGLDFACDITSYSIHYTKLXIWAPLAGICVA LLLSLIITLICYHRSRKRVCKCPRPLVRQEGKPRPSEKIV X is S, F, L, Y, C, or W |
| 26 | Chimeric CD8β with loxp sites (amino acid sequence) | LQQTPAYIKVQTNKMVMLSCEAKISLSNMRIYWLRQRQAPSSDSHH EFLALWDSAKGTIHGEEVEQEKIAVFRDASRFILNLTSVKPEDSGI YFCMIVGSPELTFGKGTQLSVVDFLPTTAQPTKKSTLKKRVCRLPR PETQKGPLCSPITSYSIHYTKLXLSLLVVCILLLLAFLGVAVYFYC VRRRARIHFMKQFHK X is S, F, L, Y, C, or W |
| 27 | HLA-A2 α chain | GSHSMRYFFTSVSRPGRGEPRFIAVGYVDDTQFVRFDSDAASQRME PRAPWIEQEGPEYWDGETRKVKAHSQTHRVDLGTLRGYYNQSEAGS HTVQRMYGCDVGSDWRFLRGYHQYAYDGKDYIALKEDLRSWTAADM AAQTTKHKWEAAHVAEQLRAYLEGTCVEWLRRYLENGKETLQRTDA PKTHMTHHAVSDHEATLRCWALSFYPAEITLTWQRDGEDQTQDTEL VETRPAGDGTFQKWAAVVVPSGQEQRYTCHVQHEGLPKPLTLRWEP SSQPTIPIVGIIAGLVLFGAVITGAVVAAVMWRRKSSDRKGGSYSQ AASSDSAQGSDVSLTACKV |
| 28 | HLA-A2 α chain A245V | GSHSMRYFFTSVSRPGRGEPRFIAVGYVDDTQFVRFDSDAASQRME PRAPWIEQEGPEYWDGETRKVKAHSQTHRVDLGTLRGYYNQSEAGS HTVQRMYGCDVGSDWRFLRGYHQYAYDGKDYIALKEDLRSWTAADM AAQTTKHKWEAAHVAEQLRAYLEGTCVEWLRRYLENGKETLQRTDA PKTHMTHHAVSDHEATLRCWALSFYPAEITLTWQRDGEDQTQDTEL VETRPAGDGTFQKWVAVVVPSGQEQRYTCHVQHEGLPKPLTLRWEP SSQPTIPIVGIIAGLVLFGAVITGAVVAAVMWRRKSSDRKGGSYSQ AASSDSAQGSDVSLTACKV |
| 29 | HLA-A2 α chain D227K/T228A | GSHSMRYFFTSVSRPGRGEPRFIAVGYVDDTQFVRFDSDAASQRME PRAPWIEQEGPEYWDGETRKVKAHSQTHRVDLGTLRGYYNQSEAGS HTVQRMYGCDVGSDWRFLRGYHQYAYDGKDYIALKEDLRSWTAADM AAQTTKHKWEAAHVAEQLRAYLEGTCVEWLRRYLENGKETLQRTDA PKTHMTHHAVSDHEATLRCWALSFYPAEITLTWQRDGEDQTQKAEL VETRPAGDGTFQKWAAVVVPSGQEQRYTCHVQHEGLPKPLTLRWEP SSQPTIPIVGIIAGLVLFGAVITGAVVAAVMWRRKSSDRKGGSYSQ AASSDSAQGSDVSLTACKV |
| 30 | Mart-1 peptide | ELAGIGILTV |
| 31 | E6 peptide | KLPQLCTEL |
| 32 | E7 peptide | GTLGIVCPI |
| 33 | NY-ESO-1 peptide | SLLMWITQV |
| 34 | peptide | ILLWQPIPV |
| 35 | Chimeric C259 α chain | QEVTQIPAALSVPEGENLVLNCSFTDSAIYNLQWFRQDPGKGLTS LLLIPFWQREQTSGRLNASLDKSSGRSTLYIAASQPGDSATYLCA VRPLYGGSYIPTFGRGTSLIVHPYIQNPEPAVYQLKDPRSQDSTL |

TABLE 1-continued

Amino acid sequences of exemplary co-receptors, TCRs, MHCs and peptide antigens

| SEQ ID NO: | Description (protein sequences unless otherwise indicated) | Sequence |
|---|---|---|
|  |  | CLFTDFDSQINVPKTMESGTFITDKTVLDMKAMDSKSNGAIAWSN QTSFTCQDIFKETNATYPSSDVPCDATLTEKSFETDMNLNFQNLS VMGLRILLLKVAGFNLLMTLRLWSS |
| 36 | Chimeric C259 β chain | AGVTQTPKFQVLKTGQSMTLQCAQDMNHEYMSWYRQDPGMGLRLI HYSVSVGMTDQGEVPNGYNVSRSTTEDFPLRLLSAAPSQTSVYFC ASSYVGNTGELFFGEGSRLTVLEDLRNVTPPKVSLFEPSKAEIAN KQKATLVCLARGFFPDHVELSWWVNGKEVHSGVSTDPQAYKESNY SYCLSSRLRVSATFWHNPRNHFRCQVQFHGLSEEDKWPEGSPKPV TQNISAEAWGRADCGITSASYQQGVLSATILYEILLGKATLYAVL VSTLVVMAMVKRKNS |

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Any patent, patent application, publication, or other disclosure material identified in the specification is hereby incorporated by reference in its entirety and for all purposes to the same extent as if each such individual reference (e.g., patent, patent application, publication, or other disclosure material) was specifically and individually indicated to be incorporated by reference in its entirety for all purposes. Any material, or portion thereof, that is said to be incorporated by reference herein, but which conflicts with existing definitions, statements, or other disclosure material set forth herein, is only incorporated by reference to the extent that no conflict arises between that incorporated by reference material and the present disclosure material.

Other embodiments are within the following claims.

What is claimed is:

1. An isolated cell derived from a mouse lymphocyte, the isolated cell expressing a chimeric CD8 on the cell surface, wherein the isolated cell comprises:
   (a) a first polynucleotide encoding a chimeric CD8α chain comprising an extracellular region of human CD8α and transmembrane and cytoplasmic regions of mouse CD8α,
   (b) a second polynucleotide encoding a chimeric CD8β chain comprising an extracellular region of human CD8β and transmembrane and cytoplasmic regions of mouse CD8β, wherein the isolated cell expresses CD3 but does not express endogenous TCR on the cell surface; and
   (c) one or more reporter system for measurement of TCR signaling;
   wherein the chimeric CD8α chain comprises the amino acid sequence of SEQ ID NO: 1, and/or the chimeric CD8β chain comprises the amino acid sequence of SEQ ID NO: 2.

2. The isolated cell of claim 1, wherein:
   (a) the one or more reporter systems provide a measurement of TCR signaling comprising one or more activities of the isolated cell selected from the group consisting of nuclear factor of activated T-cell (NFAT) signaling, IL-2 signaling, activator protein-I (API) signaling, NFKB/Rel signaling, and calcium flux; and
   (b) the one or more reporter systems comprise a polynucleotide comprising a promoter region operably linked to a polynucleotide sequence encoding a detectable marker.

3. The isolated cell of claim 1, wherein:
   (a) the isolated cell is derived from a single cell and wherein when the cell is expanded to a plurality of cells of at least I $0^5$ and transduced or transfected with separate polynucleotide vectors encoding a TCR α chain and a TCR β chain to express a recombinant TCR comprising the TCR α chain and the TCR β chain under conditions that maximize transduction or transfection efficiency, at least 20% of the plurality of cells express the recombinant TCR on the cell surface, optionally the cell has previously been subjected to one or more rounds of transduction or transfection;
   (b) the mouse lymphocyte is a T cell, B cell, or an NK cell;
   (c) the mouse lymphocyte is a T cell that is selected from the group consisting of a CD8+ cytotoxic T cell, a CD8+ regulatory T cell, a CD4+ cytotoxic T cell, a CD4+ helper T cell, and a CD4+ regulatory T cell; and/or
   (d) the mouse lymphocyte is selected from the group consisting of a RAG1 or RAG2 knockout murine cell, an immature murine T cell, a mouse DO-11.10.7 58 α-β- (5831 /-) cell, and a mouse Bw5147 cell.

4. The isolated cell of claim 1, wherein the cell further expresses a recombinant TCR on the cell surface, the recombinant TCR comprising a TCR a chain and a TCR β chain, wherein the TCR α chain and the TCR β chain each comprises a variable region and a non-variable region, each non-variable region comprising a constant region, a transmembrane region, and a cytoplasmic region, wherein for each chain, the variable region is linked to the constant region, the constant region is linked to the transmembrane region, and the transmembrane region is linked to the cytoplasmic region.

5. The isolated cell of claim 4, wherein the recombinant TCR is a fusion molecule comprising a co-stimulatory signaling region.

6. A cellular library comprising a plurality of the isolated cells of claim 1.

7. The isolated cell of claim 2, wherein the promoter region is an IL-2 promoter or a minimal IL-2 promoter.

8. The isolated cell of claim 7, wherein the IL-2 promoter comprises one or more transcriptional response elements comprising nuclear factor of activated T-cell (NFAT) response elements, activator protein-I (API) response elements, or NFKB/Rel response elements.

9. The isolated cell of claim 2, wherein the IL-2 promoter comprises three NFAT binding sites.

10. The isolated cell of claim 2, wherein the detectable marker is a fluorescent protein, a cell surface marker, or an antibiotic selection marker.

11. The isolated cell of claim 2, wherein the detectable marker is enhanced green fluorescent protein (EGFP).

12. The cellular library of claim 6, wherein the cellular library has a TCR diversity of at least $10^7$, $10^8$, or $10^9$.

* * * * *

UNITED STATES PATENT AND TRADEMARK OFFICE
CERTIFICATE OF CORRECTION

| | |
|---|---|
| PATENT NO. | : 11,898,165 B2 |
| APPLICATION NO. | : 15/759007 |
| DATED | : February 13, 2024 |
| INVENTOR(S) | : Marc Van Dijk et al. |

Page 1 of 1

It is certified that error appears in the above-identified patent and that said Letters Patent is hereby corrected as shown below:

On the Title Page

Item (71) Applicant:
"MiNk Therapeutics, Inc., New York, NY (US)"
Should read:
-- MiNK Therapeutics, Inc., New York, NY (US) --

In the Claims

At Column 102, Claim 3, Line 39:
"α–β– (5831 /–) cell, and a mouse Bw5147 cell."
Should read:
-- α-β - (58-/-) cell, and a mouse Bw5147 cell. --

Signed and Sealed this
Twenty-sixth Day of March, 2024

Katherine Kelly Vidal
*Director of the United States Patent and Trademark Office*

SEQUENCE LISTING

```
<160> NUMBER OF SEQ ID NOS: 36

<210> SEQ ID NO 1
<211> LENGTH: 212
<212> TYPE: PRT
<213> ORGANISM: Artificial Sequence
<220> FEATURE:
<223> OTHER INFORMATION: Chimeric CD8a

<400> SEQUENCE: 1

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
                20                  25                  30

Cys Ser Trp Leu Phe Gln Pro Arg Gly Ala Ala Ala Ser Pro Thr Phe
            35                  40                  45

Leu Leu Tyr Leu Ser Gln Asn Lys Pro Lys Ala Ala Glu Gly Leu Asp
        50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160
```

Asp Ile Trp Ala Pro Leu Ala Gly Ile Cys Val Ala Leu Leu Leu Ser
                165                 170                 175

Leu Ile Ile Thr Leu Ile Cys Tyr His Arg Ser Arg Lys Arg Val Cys
            180                 185                 190

Lys Cys Pro Arg Pro Leu Val Arg Gln Glu Gly Lys Pro Arg Pro Ser
        195                 200                 205

Glu Lys Ile Val
    210

<210> SEQ ID NO 2
<211> LENGTH: 187
<212> TYPE: PRT
<213> ORGANISM: Artificial Sequence
<220> FEATURE:
<223> OTHER INFORMATION: Chimeric CD8b

<400> SEQUENCE: 2

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His Glu Phe
        35                  40                  45

Leu Ala Leu Trp Asp Ser Ala Lys Gly Thr Ile His Gly Glu Glu Val
50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
            85                  90                  95

Ile Val Gly Ser Pro Glu Leu Thr Phe Gly Lys Gly Thr Gln Leu Ser
        100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro Leu Ser Leu Leu Val Val Cys Ile Leu Leu Leu
145                 150                 155                 160

Leu Ala Phe Leu Gly Val Ala Val Tyr Phe Tyr Cys Val Arg Arg Arg
                165                 170                 175

Ala Arg Ile His Phe Met Lys Gln Phe His Lys
            180                 185

<210> SEQ ID NO 3
<211> LENGTH: 709
<212> TYPE: DNA
<213> ORGANISM: Artificial Sequence
<220> FEATURE:
<223> OTHER INFORMATION: Chimeric CD8a with loxp sites (nucleotide
      sequence)

<400> SEQUENCE: 3
agccagttca gagtgtcccc cctggacaga acctggaacc tgggcgagac agtggaactg      60
aagtgccagg tgctgctgag caaccccacc agcggctgta gctggctgtt ccagcctaga     120
ggcgccgctg ccagccctac ctttctgctg tacctgagcc agaacaagcc caaggccgcc     180
gagggcctgg acacccagag attcagcggc aagagactgg cgacaccttc gtgctgacc      240 ctgagcgact tcagaagaga gaacgagggc tactacttct gcagcgccct gagcaacagc     300

```
atcatgtact tcagccactt cgtgcccgtg tttctgcccg ccaagcctac cacaacccct    360
gcccctagac ctcctacccc agcccctaca atcgccagcc agcctctgtc tctgaggccc    420
gaggcttgta gaccagctgc tggcggagcc gtgcacacaa gaggcctgga cttcgcctgc    480
gacataactt cgtatagcat acattatacg aagttatcta tctgggctcc actggccggc    540
atttgtgtgg cactgctgct gtccctgatc atcaccctga tctgctacca cagatcccgg    600
aagcgcgtgt gcaagtgccc tagaccactc gtgcggcagg aaggcaagcc agacccagc    660 gagaagattg tctgaataac ttcgtatagc atacattata cgaagttat                709
```

```
<210> SEQ ID NO 4
<211> LENGTH: 634
<212> TYPE: DNA
<213> ORGANISM: Artificial Sequence
<220> FEATURE:
<223> OTHER INFORMATION: Chimeric CD8b with loxp sites (nucleotide
      sequence)

<400> SEQUENCE: 4
```

```
ctgcagcaga ccccccgccta catcaaggtg cagaccaaca agatggtcat gctgagctgc    60
gaggccaaga tcagcctgag caacatgaga atctactggc tgagacagag acaggccccc   120
agcagcgaca gccaccacga gtttctggcc ctgtgggaca gcgccaaggg caccatccat   180
ggcgaggaag tggaacagga aaagatcgcc gtgttcaggg acgccagcag attcatcctg   240
aacctgacca gcgtgaagcc cgaggacagc ggaatctact tctgcatgat cgtgggcagc   300
cccgagctga ccttcggcaa gggaacacag ctgagcgtgg tggacttcct gcctaccacc   360
gcccagccca ccaagaagtc taccctgaag aaaagagtgt gcagactgcc cagacccgag   420
acacagaaag gccctctgtg cagccctata acttcgtata gcatacatta tacgaagtta   480
tctctgagcc tgctggtcgt gtgcatcctc ctgctgctgg cttttctggg cgtggccgtg   540
tacttctact gcgtgcggag aagggccagg atccacttta tgaagcagtt ccacaaatga   600
ataacttcgt atagcataca ttatacgaag ttat                                634
```

```
<210> SEQ ID NO 5
<211> LENGTH: 224
<212> TYPE: PRT
<213> ORGANISM: Artificial Sequence
<220> FEATURE:
<223> OTHER INFORMATION: Chimeric CD8a with loxp sites (amino acid
      sequence)

<400> SEQUENCE: 5
```

```
Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110
```

```
Pro Ala Lys Pro Thr Thr Thr Pro Ala Pro Arg Pro Pro Thr Pro Ala
            115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp Ile Thr Ser Tyr Ser Ile His Tyr Thr Lys Leu Ser Ile Trp Ala
                165                 170                 175

Pro Leu Ala Gly Ile Cys Val Ala Leu Leu Leu Ser Leu Ile Ile Thr
            180                 185                 190

Leu Ile Cys Tyr His Arg Ser Arg Lys Arg Val Cys Lys Cys Pro Arg
        195                 200                 205

Pro Leu Val Arg Gln Glu Gly Lys Pro Arg Pro Ser Glu Lys Ile Val
    210                 215                 220
```

<210> SEQ ID NO 6
<211> LENGTH: 199
<212> TYPE: PRT
<213> ORGANISM: Artificial Sequence
<220> FEATURE:
<223> OTHER INFORMATION: Chimeric CD8b with loxp sites (amino acid sequence)

<400> SEQUENCE: 6

```
Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
    130                 135                 140

Pro Leu Cys Ser Pro Ile Thr Ser Tyr Ser Ile His Tyr Thr Lys Leu
145                 150                 155                 160

Ser Leu Ser Leu Leu Val Val Cys Ile Leu Leu Leu Ala Phe Leu
                165                 170                 175

Gly Val Ala Val Tyr Phe Tyr Cys Val Arg Arg Arg Ala Arg Ile His
            180                 185                 190

Phe Met Lys Gln Phe His Lys
        195
```

<210> SEQ ID NO 7
<211> LENGTH: 251
<212> TYPE: PRT
<213> ORGANISM: Artificial Sequence
<220> FEATURE:
<223> OTHER INFORMATION: Chimeric C58 alpha chain

<400> SEQUENCE: 7

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Thr Pro Trp Gln Arg Glu Gln Thr Ser Gly Arg Leu Asn Ala
50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr Ile Gln Asn Pro Glu Pro Ala Val Tyr Gln Leu Lys Asp
        115                 120                 125

Pro Arg Ser Gln Asp Ser Thr Leu Cys Leu Phe Thr Asp Phe Asp Ser
130                 135                 140

Gln Ile Asn Val Pro Lys Thr Met Glu Ser Gly Thr Phe Ile Thr Asp
145                 150                 155                 160

Lys Thr Val Leu Asp Met Lys Ala Met Asp Ser Lys Ser Asn Gly Ala
                165                 170                 175

Ile Ala Trp Ser Asn Gln Thr Ser Phe Thr Cys Gln Asp Ile Phe Lys
            180                 185                 190

Glu Thr Asn Ala Thr Tyr Pro Ser Ser Asp Val Pro Cys Asp Ala Thr
        195                 200                 205

Leu Thr Glu Lys Ser Phe Glu Thr Asp Met Asn Leu Asn Phe Gln Asn
210                 215                 220

Leu Ser Val Met Gly Leu Arg Ile Leu Leu Leu Lys Val Ala Gly Phe
225                 230                 235                 240

Asn Leu Leu Met Thr Leu Arg Leu Trp Ser Ser
                245                 250

<210> SEQ ID NO 8
<211> LENGTH: 286
<212> TYPE: PRT
<213> ORGANISM: Artificial Sequence
<220> FEATURE:
<223> OTHER INFORMATION: Chimeric C58 beta chain

<400> SEQUENCE: 8

Asn Ala Gly Val Thr Gln Thr Pro Lys Phe Gln Val Leu Lys Thr Gly
1               5                   10                  15

Gln Ser Met Thr Leu Gln Cys Ala Gln Asp Met Asn His Glu Tyr Met
            20                  25                  30

Ser Trp Tyr Arg Gln Asp Pro Gly Met Gly Leu Arg Leu Ile His Tyr
        35                  40                  45

Ser Val Ala Ile Gln Thr Thr Asp Gln Gly Glu Val Pro Asn Gly Tyr
50                  55                  60

Asn Val Ser Arg Ser Thr Ile Glu Asp Phe Pro Leu Arg Leu Leu Ser
65                  70                  75                  80

Ala Ala Pro Ser Gln Thr Ser Val Tyr Phe Cys Ala Ser Ser Tyr Leu
                85                  90                  95

Gly Asn Thr Gly Glu Leu Phe Phe Gly Gly Ser Arg Leu Thr Val
            100                 105                 110

Leu Glu Asp Leu Arg Asn Val Thr Pro Pro Lys Val Ser Leu Phe Glu
115                 120                 125

Pro Ser Lys Ala Glu Ile Ala Asn Lys Gln Lys Ala Thr Leu Val Cys
130                 135                 140

Leu Ala Arg Gly Phe Phe Pro Asp His Val Glu Leu Ser Trp Trp Val
145                 150                 155                 160

Asn Gly Lys Glu Val His Ser Gly Val Ser Thr Asp Pro Gln Ala Tyr
                165                 170                 175

Lys Glu Ser Asn Tyr Ser Tyr Cys Leu Ser Ser Arg Leu Arg Val Ser
            180                 185                 190

Ala Thr Phe Trp His Asn Pro Arg Asn His Phe Arg Cys Gln Val Gln
        195                 200                 205

Phe His Gly Leu Ser Glu Glu Asp Lys Trp Pro Glu Gly Ser Pro Lys
210                 215                 220

Pro Val Thr Gln Asn Ile Ser Ala Glu Ala Trp Gly Arg Ala Asp Cys
225                 230                 235                 240

Gly Ile Thr Ser Ala Ser Tyr His Gln Gly Val Leu Ser Ala Thr Ile
                245                 250                 255

Leu Tyr Glu Ile Leu Leu Gly Lys Ala Thr Leu Tyr Ala Val Leu Val
            260                 265                 270

Ser Gly Leu Val Leu Met Ala Met Val Lys Lys Asn Ser
            275                 280                 285

<210> SEQ ID NO 9
<211> LENGTH: 246
<212> TYPE: PRT
<213> ORGANISM: Artificial Sequence
<220> FEATURE:
<223> OTHER INFORMATION: Chimeric DMF4 alpha chain

<400> SEQUENCE: 9

Gly Gln Gln Leu Asn Gln Ser Pro Gln Ser Met Phe Ile Gln Glu Gly
1               5                   10                  15

Glu Asp Val Ser Met Asn Cys Thr Ser Ser Ser Ile Phe Asn Thr Trp
            20                  25                  30

Leu Trp Tyr Lys Gln Asp Pro Gly Glu Gly Pro Val Leu Leu Ile Ala
        35                  40                  45

Leu Tyr Lys Ala Gly Glu Leu Thr Ser Asn Gly Arg Leu Thr Ala Gln
    50                  55                  60

Phe Gly Ile Thr Arg Lys Asp Ser Phe Leu Asn Ile Ser Ala Ser Ile
65                  70                  75                  80

Pro Ser Asp Val Gly Ile Tyr Phe Cys Ala Gly Gly Thr Gly Asn Gln
                85                  90                  95

Phe Tyr Phe Gly Thr Gly Thr Ser Leu Thr Val Ile Pro Tyr Ile Gln
            100                 105                 110

Asn Pro Glu Pro Ala Val Tyr Gln Leu Lys Asp Pro Arg Ser Gln Asp
        115                 120                 125

Ser Thr Leu Cys Leu Phe Thr Asp Phe Asp Ser Gln Ile Asn Val Pro
130                 135                 140

Lys Thr Met Glu Ser Gly Thr Phe Ile Thr Asp Lys Thr Val Leu Asp
145                 150                 155                 160

Met Lys Ala Met Asp Ser Lys Ser Asn Gly Ala Ile Ala Trp Ser Asn
                165                 170                 175

```
Gln Thr Ser Phe Thr Cys Gln Asp Ile Phe Lys Glu Thr Asn Ala Thr
            180                 185                 190

Tyr Pro Ser Ser Asp Val Pro Cys Asp Ala Thr Leu Thr Glu Lys Ser
        195                 200                 205

Phe Glu Thr Asp Met Asn Leu Asn Phe Gln Asn Leu Ser Val Met Gly
    210                 215                 220

Leu Arg Ile Leu Leu Leu Lys Val Ala Gly Phe Asn Leu Leu Met Thr
225                 230                 235                 240

Leu Arg Leu Trp Ser Ser
                245

<210> SEQ ID NO 10
<211> LENGTH: 286
<212> TYPE: PRT
<213> ORGANISM: Artificial Sequence
<220> FEATURE:
<223> OTHER INFORMATION: Chimeric DMF4 beta chain

<400> SEQUENCE: 10

Asp Ala Gly Ile Thr Gln Ser Pro Arg His Lys Val Thr Glu Thr Gly
1               5                   10                  15

Thr Pro Val Thr Leu Arg Cys His Gln Thr Glu Asn His Arg Tyr Met
            20                  25                  30

Tyr Trp Tyr Arg Gln Asp Pro Gly His Gly Leu Arg Leu Ile His Tyr
        35                  40                  45

Ser Tyr Gly Val Lys Asp Thr Asp Lys Gly Glu Val Ser Asp Gly Tyr
    50                  55                  60

Ser Val Ser Arg Ser Lys Thr Glu Asp Phe Leu Leu Thr Leu Glu Ser
65                  70                  75                  80

Ala Thr Ser Ser Gln Thr Ser Val Tyr Phe Cys Ala Ile Ser Glu Val
                85                  90                  95

Gly Val Gly Gln Pro Gln His Phe Gly Asp Gly Thr Arg Leu Ser Ile
            100                 105                 110

Leu Glu Asp Leu Arg Asn Val Thr Pro Pro Lys Val Ser Leu Phe Glu
        115                 120                 125

Pro Ser Lys Ala Glu Ile Ala Asn Lys Gln Lys Ala Thr Leu Val Cys
    130                 135                 140

Leu Ala Arg Gly Phe Phe Pro Asp His Val Glu Leu Ser Trp Trp Val
145                 150                 155                 160

Asn Gly Lys Glu Val His Ser Gly Val Ser Thr Asp Pro Gln Ala Tyr
                165                 170                 175

Lys Glu Ser Asn Tyr Ser Tyr Cys Leu Ser Ser Arg Leu Arg Val Ser
            180                 185                 190

Ala Thr Phe Trp His Asn Pro Arg Asn His Phe Arg Cys Gln Val Gln
        195                 200                 205

Phe His Gly Leu Ser Glu Glu Asp Lys Trp Pro Glu Gly Ser Pro Lys
    210                 215                 220

Pro Val Thr Gln Asn Ile Ser Ala Glu Ala Trp Gly Arg Ala Asp Cys
225                 230                 235                 240

Gly Ile Thr Ser Ala Ser Tyr Gln Gln Gly Val Leu Ser Ala Thr Ile
                245                 250                 255

Leu Tyr Glu Ile Leu Leu Gly Lys Ala Thr Leu Tyr Ala Val Leu Val
            260                 265                 270

Ser Thr Leu Val Val Met Ala Met Val Lys Arg Lys Asn Ser
        275                 280                 285
```

<210> SEQ ID NO 11
<211> LENGTH: 247
<212> TYPE: PRT
<213> ORGANISM: Artificial Sequence
<220> FEATURE:
<223> OTHER INFORMATION: Chimeric DMF5 alpha chain

<400> SEQUENCE: 11

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Phe Gly Gly Gly
                85                  90                  95

Lys Leu Ile Phe Gly Gln Gly Thr Glu Leu Ser Val Lys Pro Tyr Ile
            100                 105                 110

Gln Asn Pro Glu Pro Ala Val Tyr Gln Leu Lys Asp Pro Arg Ser Gln
        115                 120                 125

Asp Ser Thr Leu Cys Leu Phe Thr Asp Phe Asp Ser Gln Ile Asn Val
    130                 135                 140

Pro Lys Thr Met Glu Ser Gly Thr Phe Ile Thr Asp Lys Thr Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
            180                 185                 190

Thr Tyr Pro Ser Ser Asp Val Pro Cys Asp Ala Thr Leu Thr Glu Lys
        195                 200                 205

Ser Phe Glu Thr Asp Met Asn Leu Asn Phe Gln Asn Leu Ser Val Met
    210                 215                 220

Gly Leu Arg Ile Leu Leu Leu Lys Val Ala Gly Phe Asn Leu Leu Met
225                 230                 235                 240

Thr Leu Arg Leu Trp Ser Ser
            245

<210> SEQ ID NO 12
<211> LENGTH: 285
<212> TYPE: PRT
<213> ORGANISM: Artificial Sequence
<220> FEATURE:
<223> OTHER INFORMATION: Chimeric DMF5 beta chain

<400> SEQUENCE: 12

Ile Ala Gly Ile Thr Gln Ala Pro Thr Ser Gln Ile Leu Ala Ala Gly
1               5                   10                  15

Arg Arg Met Thr Leu Arg Cys Thr Gln Asp Met Arg His Asn Ala Met
            20                  25                  30

Tyr Trp Tyr Arg Gln Asp Leu Gly Leu Gly Leu Arg Leu Ile His Tyr
        35                  40                  45

Ser Asn Thr Ala Gly Thr Thr Gly Lys Gly Glu Val Pro Asp Gly Tyr
    50                  55                  60

Ser Val Ser Arg Ala Asn Thr Asp Asp Phe Pro Leu Thr Leu Ala Ser
 65                  70                  75                  80

Ala Val Pro Ser Gln Thr Ser Val Tyr Phe Cys Ala Ser Ser Leu Ser
             85                  90                  95

Phe Gly Thr Glu Ala Phe Phe Gly Gln Gly Thr Arg Leu Thr Val Val
        100                 105                 110

Glu Asp Leu Arg Asn Val Thr Pro Pro Lys Val Ser Leu Phe Glu Pro
    115                 120                 125

Ser Lys Ala Glu Ile Ala Asn Lys Gln Lys Ala Thr Leu Val Cys Leu
130                 135                 140

Ala Arg Gly Phe Phe Pro Asp His Val Glu Leu Ser Trp Trp Val Asn
145                 150                 155                 160

Gly Lys Glu Val His Ser Gly Val Ser Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Thr Leu Val Val Met Ala Met Val Lys Arg Lys Asn Ser
        275                 280                 285

<210> SEQ ID NO 13
<211> LENGTH: 137
<212> TYPE: PRT
<213> ORGANISM: Mus musculus
<220> FEATURE:
<221> NAME/KEY: VARIANT
<222> LOCATION: (1)..(1)
<223> OTHER INFORMATION: X can be any amino acid

<400> SEQUENCE: 13

Xaa Ile Gln Asn Pro Glu Pro Ala Val Tyr Gln Leu Lys Asp Pro Arg
 1               5                  10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
 50                  55                  60

Trp Ser Asn Gln Thr Ser Phe Thr Cys Gln Asp Ile Phe Lys Glu Thr
 65                  70                  75                  80

Asn Ala Thr Tyr Pro Ser Ser Asp Val Pro Cys Asp Ala Thr Leu Thr
             85                  90                  95

Glu Lys Ser Phe Glu Thr Asp Met Asn Leu Asn Phe Gln Asn Leu Ser
        100                 105                 110

Val Met Gly Leu Arg Ile Leu Leu Leu Lys Val Ala Gly Phe Asn Leu
    115                 120                 125

```
Leu Met Thr Leu Arg Leu Trp Ser Ser
    130                 135
```

<210> SEQ ID NO 14
<211> LENGTH: 26
<212> TYPE: PRT
<213> ORGANISM: Mus musculus

<400> SEQUENCE: 14

```
Ser Val Met Gly Leu Arg Ile Leu Leu Lys Val Ala Gly Phe Asn
1               5                   10                  15

Leu Leu Met Thr Leu Arg Leu Trp Ser Ser
            20                  25
```

<210> SEQ ID NO 15
<211> LENGTH: 173
<212> TYPE: PRT
<213> ORGANISM: Mus musculus
<220> FEATURE:
<221> NAME/KEY: VARIANT
<222> LOCATION: (1)..(1)
<223> OTHER INFORMATION: X can be any amino acid

<400> SEQUENCE: 15

```
Xaa Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Lys Arg Lys Asn Ser
                165                 170
```

<210> SEQ ID NO 16
<211> LENGTH: 28
<212> TYPE: PRT
<213> ORGANISM: Mus musculus

<400> SEQUENCE: 16

```
Glu Ile Leu Leu Gly Lys Ala Thr Leu Tyr Ala Val Leu Val Ser Thr
1               5                   10                  15

Leu Val Val Met Ala Met Val Lys Arg Lys Asn Ser
            20                  25
```

<210> SEQ ID NO 17
<211> LENGTH: 171

```
<212> TYPE: PRT
<213> ORGANISM: Mus musculus
<220> FEATURE:
<221> NAME/KEY: VARIANT
<222> LOCATION: (1)..(1)
<223> OTHER INFORMATION: X can be any amino acid

<400> SEQUENCE: 17

Xaa Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr Gln Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Thr Leu Val Val Met Ala Met Val Arg Asn Arg
                165                 170

<210> SEQ ID NO 18
<211> LENGTH: 26
<212> TYPE: PRT
<213> ORGANISM: Mus musculus

<400> SEQUENCE: 18

Glu Ile Leu Leu Gly Lys Ala Thr Leu Tyr Ala Val Leu Val Ser Thr
1               5                   10                  15

Leu Val Val Met Ala Met Val Arg Asn Arg
            20                  25

<210> SEQ ID NO 19
<211> LENGTH: 173
<212> TYPE: PRT
<213> ORGANISM: Mus musculus
<220> FEATURE:
<221> NAME/KEY: VARIANT
<222> LOCATION: (1)..(1)
<223> OTHER INFORMATION: X can be any amino acid

<400> SEQUENCE: 19

Xaa Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60
```

```
Glu Ser Asn Tyr Ser Tyr Cys Leu Ser Ser Arg Leu Arg Val Ser Ala
 65                  70                  75                  80

Thr Phe Trp His Asn Pro Arg Asn His Phe Arg Cys Gln Val Gln Phe
                 85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170

<210> SEQ ID NO 20
<211> LENGTH: 28
<212> TYPE: PRT
<213> ORGANISM: Mus musculus

<400> SEQUENCE: 20

Glu Ile Leu Leu Gly Lys Ala Thr Leu Tyr Ala Val Leu Val Ser Gly
1               5                   10                  15

Leu Val Leu Met Ala Met Val Lys Lys Lys Asn Ser
            20                  25

<210> SEQ ID NO 21
<211> LENGTH: 220
<212> TYPE: PRT
<213> ORGANISM: Mus musculus

<400> SEQUENCE: 21

Lys Pro Gln Ala Pro Glu Leu Arg Ile Phe Pro Lys Lys Met Asp Ala
1               5                   10                  15

Glu Leu Gly Gln Lys Val Asp Leu Val Cys Glu Val Leu Gly Ser Val
            20                  25                  30

Ser Gln Gly Cys Ser Trp Leu Phe Gln Asn Ser Ser Ser Lys Leu Pro
        35                  40                  45

Gln Pro Thr Phe Val Val Tyr Met Ala Ser Ser His Asn Lys Ile Thr
    50                  55                  60

Trp Asp Glu Lys Leu Asn Ser Ser Lys Leu Phe Ser Ala Met Arg Asp
65                  70                  75                  80

Thr Asn Asn Lys Tyr Val Leu Thr Leu Asn Lys Phe Ser Lys Glu Asn
                85                  90                  95

Glu Gly Tyr Tyr Phe Cys Ser Val Ile Ser Asn Ser Val Met Tyr Phe
            100                 105                 110

Ser Ser Val Val Pro Val Leu Gln Lys Val Asn Ser Thr Thr Thr Lys
        115                 120                 125

Pro Val Leu Arg Thr Pro Ser Pro Val His Pro Thr Gly Thr Ser Gln
    130                 135                 140

Pro Gln Arg Pro Glu Asp Cys Arg Pro Arg Gly Ser Val Lys Gly Thr
145                 150                 155                 160

Gly Leu Asp Phe Ala Cys Asp Ile Tyr Ile Trp Ala Pro Leu Ala Gly
                165                 170                 175

Ile Cys Val Ala Leu Leu Leu Ser Leu Ile Ile Thr Leu Ile Cys Tyr
            180                 185                 190
```

His Arg Ser Arg Lys Arg Val Cys Lys Cys Pro Arg Pro Leu Val Arg
        195                 200                 205

Gln Glu Gly Lys Pro Arg Pro Ser Glu Lys Ile Val
    210                 215                 220

<210> SEQ ID NO 22
<211> LENGTH: 192
<212> TYPE: PRT
<213> ORGANISM: Mus musculus

<400> SEQUENCE: 22

Leu Ile Gln Thr Pro Ser Ser Leu Leu Val Gln Thr Asn His Thr Ala
1               5                   10                  15

Lys Met Ser Cys Glu Val Lys Ser Ile Ser Lys Leu Thr Ser Ile Tyr
            20                  25                  30

Trp Leu Arg Glu Arg Gln Asp Pro Lys Asp Lys Tyr Phe Glu Phe Leu
        35                  40                  45

Ala Ser Trp Ser Ser Lys Gly Val Leu Tyr Gly Glu Ser Val Asp
    50                  55                  60

Lys Lys Arg Asn Ile Ile Leu Glu Ser Asp Ser Arg Arg Pro Phe
65                  70                  75                  80

Leu Ser Ile Met Asn Val Lys Pro Glu Asp Ser Asp Phe Tyr Phe Cys
                85                  90                  95

Ala Thr Val Gly Ser Pro Lys Met Val Phe Gly Thr Gly Thr Lys Leu
            100                 105                 110

Thr Val Val Asp Val Leu Pro Thr Thr Ala Pro Thr Lys Lys Thr Thr
        115                 120                 125

Leu Lys Met Lys Lys Lys Gln Cys Pro Phe Pro His Pro Glu Thr
130                 135                 140

Gln Lys Gly Leu Thr Cys Ser Leu Thr Thr Leu Ser Leu Leu Val Val
145                 150                 155                 160

Cys Ile Leu Leu Leu Leu Ala Phe Leu Gly Val Ala Val Tyr Phe Tyr
                165                 170                 175

Cys Val Arg Arg Arg Ala Arg Ile His Phe Met Lys Gln Phe His Lys
            180                 185                 190

<210> SEQ ID NO 23
<211> LENGTH: 214
<212> TYPE: PRT
<213> ORGANISM: Homo sapiens

<400> SEQUENCE: 23

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
        130                 135                 140

Pro Ala Ala Gly Gly Ala Val His Thr Arg Gly Leu Asp Phe Ala Cys
145                 150                 155                 160

Asp Ile Tyr Ile Trp Ala Pro Leu Ala Gly Thr Cys Gly Val Leu Leu
                165                 170                 175

Leu Ser Leu Val Ile Thr Leu Tyr Cys Asn His Arg Asn Arg Arg Arg
            180                 185                 190

Val Cys Lys Cys Pro Arg Pro Val Val Lys Ser Gly Asp Lys Pro Ser
        195                 200                 205

Leu Ser Ala Arg Tyr Val
        210

<210> SEQ ID NO 24
<211> LENGTH: 189
<212> TYPE: PRT
<213> ORGANISM: Homo sapiens

<400> SEQUENCE: 24

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110

Val Val Asp Phe Leu Pro Thr Thr Ala Gln Pro Thr Lys Lys Ser Thr
        115                 120                 125

Leu Lys Lys Arg Val Cys Arg Leu Pro Arg Pro Glu Thr Gln Lys Gly
        130                 135                 140

Pro Leu Cys Ser Pro Ile Thr Leu Gly Leu Leu Val Ala Gly Val Leu
145                 150                 155                 160

Val Leu Leu Val Ser Leu Gly Val Ala Ile His Leu Cys Cys Arg Arg
                165                 170                 175

Arg Arg Ala Arg Leu Arg Phe Met Lys Gln Phe Tyr Lys
            180                 185

<210> SEQ ID NO 25
<211> LENGTH: 224
<212> TYPE: PRT
<213> ORGANISM: Artificial Sequence
<220> FEATURE:
<223> OTHER INFORMATION: Chimeric CD8a with loxp sites (amino acid
      sequence)
<220> FEATURE:
<221> NAME/KEY: VARIANT
<222> LOCATION: (173)..(173)
<223> OTHER INFORMATION: X can be S, F, L, Y, C, or W

```
<400> SEQUENCE: 25

Ser Gln Phe Arg Val Ser Pro Leu Asp Arg Thr Trp Asn Leu Gly Glu
1               5                   10                  15

Thr Val Glu Leu Lys Cys Gln Val Leu Leu Ser Asn Pro Thr Ser Gly
            20                  25                  30

Cys Ser Trp Leu Phe Gln Pro Arg Gly Ala Ala Ala Ser Pro Thr Phe
        35                  40                  45

Leu Leu Tyr Leu Ser Gln Asn Lys Pro Lys Ala Ala Glu Gly Leu Asp
    50                  55                  60

Thr Gln Arg Phe Ser Gly Lys Arg Leu Gly Asp Thr Phe Val Leu Thr
65                  70                  75                  80

Leu Ser Asp Phe Arg Arg Glu Asn Glu Gly Tyr Tyr Phe Cys Ser Ala
                85                  90                  95

Leu Ser Asn Ser Ile Met Tyr Phe Ser His Phe Val Pro Val Phe Leu
            100                 105                 110

Pro Ala Lys Pro Thr Thr Thr Pro Ala Pro Arg Pro Pro Thr Pro Ala
        115                 120                 125

Pro Thr Ile Ala Ser Gln Pro Leu Ser Leu Arg Pro Glu Ala Cys Arg
    130                 135                 140

Pro Ala Ala Gly Gly Ala Val His Thr Arg Gly Leu Asp Phe Ala Cys
145                 150                 155                 160

Asp Ile Thr Ser Tyr Ser Ile His Tyr Thr Lys Leu Xaa Ile Trp Ala
                165                 170                 175

Pro Leu Ala Gly Ile Cys Val Ala Leu Leu Leu Ser Leu Ile Ile Thr
            180                 185                 190

Leu Ile Cys Tyr His Arg Ser Arg Lys Arg Val Cys Lys Cys Pro Arg
        195                 200                 205

Pro Leu Val Arg Gln Glu Gly Lys Pro Arg Pro Ser Glu Lys Ile Val
    210                 215                 220

<210> SEQ ID NO 26
<211> LENGTH: 199
<212> TYPE: PRT
<213> ORGANISM: Artificial Sequence
<220> FEATURE:
<223> OTHER INFORMATION: Chimeric CD8b with loxp sites (amino acid
      sequence)
<220> FEATURE:
<221> NAME/KEY: VARIANT
<222> LOCATION: (161)..(161)
<223> OTHER INFORMATION: X can be S, F, L, Y, C, or W

<400> SEQUENCE: 26

Leu Gln Gln Thr Pro Ala Tyr Ile Lys Val Gln Thr Asn Lys Met Val
1               5                   10                  15

Met Leu Ser Cys Glu Ala Lys Ile Ser Leu Ser Asn Met Arg Ile Tyr
            20                  25                  30

Trp Leu Arg Gln Arg Gln Ala Pro Ser Ser Asp Ser His His Glu Phe
        35                  40                  45

Leu Ala Leu Trp Asp Ser Ala Lys Gly Thr Ile His Gly Glu Glu Val
    50                  55                  60

Glu Gln Glu Lys Ile Ala Val Phe Arg Asp Ala Ser Arg Phe Ile Leu
65                  70                  75                  80

Asn Leu Thr Ser Val Lys Pro Glu Asp Ser Gly Ile Tyr Phe Cys Met
                85                  90                  95

Ile Val Gly Ser Pro Glu Leu Thr Phe Gly Lys Gly Thr Gln Leu Ser
            100                 105                 110
```

```
Val Val Asp Phe Leu Pro Thr Thr Ala Gln Pro Thr Lys Lys Ser Thr
            115                 120                 125

Leu Lys Lys Arg Val Cys Arg Leu Pro Arg Pro Glu Thr Gln Lys Gly
130                 135                 140

Pro Leu Cys Ser Pro Ile Thr Ser Tyr Ser Ile His Tyr Thr Lys Leu
145                 150                 155                 160

Xaa Leu Ser Leu Leu Val Val Cys Ile Leu Leu Leu Ala Phe Leu
            165                 170                 175

Gly Val Ala Val Tyr Phe Tyr Cys Val Arg Arg Ala Arg Ile His
            180                 185                 190

Phe Met Lys Gln Phe His Lys
            195

<210> SEQ ID NO 27
<211> LENGTH: 341
<212> TYPE: PRT
<213> ORGANISM: Homo sapiens

<400> SEQUENCE: 27

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
```

```
                275                 280                 285
Ala Gly Leu Val Leu Phe Gly Ala Val Ile Thr Gly Ala Val Val Ala
        290                 295                 300
Ala Val Met Trp Arg Arg Lys Ser Ser Asp Arg Lys Gly Gly Ser Tyr
305                 310                 315                 320
Ser Gln Ala Ala Ser Ser Asp Ser Ala Gln Gly Ser Asp Val Ser Leu
                325                 330                 335
Thr Ala Cys Lys Val
            340

<210> SEQ ID NO 28
<211> LENGTH: 341
<212> TYPE: PRT
<213> ORGANISM: Artificial Sequence
<220> FEATURE:
<223> OTHER INFORMATION: HLA-A2 alpha chain  A245V

<400> SEQUENCE: 28

Gly Ser His Ser Met Arg Tyr Phe Phe Thr Ser Val Ser Arg Pro Gly
1               5                   10                  15
Arg Gly Glu Pro Arg Phe Ile Ala Val Gly Tyr Val Asp Asp Thr Gln
            20                  25                  30
Phe Val Arg Phe Asp Ser Asp Ala Ala Ser Gln Arg Met Glu Pro Arg
        35                  40                  45
Ala Pro Trp Ile Glu Gln Glu Gly Pro Glu Tyr Trp Asp Gly Glu Thr
    50                  55                  60
Arg Lys Val Lys Ala His Ser Gln Thr His Arg Val Asp Leu Gly Thr
65                  70                  75                  80
Leu Arg Gly Tyr Tyr Asn Gln Ser Glu Ala Gly Ser His Thr Val Gln
                85                  90                  95
Arg Met Tyr Gly Cys Asp Val Gly Ser Asp Trp Arg Phe Leu Arg Gly
            100                 105                 110
Tyr His Gln Tyr Ala Tyr Asp Gly Lys Asp Tyr Ile Ala Leu Lys Glu
        115                 120                 125
Asp Leu Arg Ser Trp Thr Ala Ala Asp Met Ala Ala Gln Thr Thr Lys
    130                 135                 140
His Lys Trp Glu Ala Ala His Val Ala Glu Gln Leu Arg Ala Tyr Leu
145                 150                 155                 160
Glu Gly Thr Cys Val Glu Trp Leu Arg Arg Tyr Leu Glu Asn Gly Lys
                165                 170                 175
Glu Thr Leu Gln Arg Thr Asp Ala Pro Lys Thr His Met Thr His His
            180                 185                 190
Ala Val Ser Asp His Glu Ala Thr Leu Arg Cys Trp Ala Leu Ser Phe
        195                 200                 205
Tyr Pro Ala Glu Ile Thr Leu Thr Trp Gln Arg Asp Gly Glu Asp Gln
    210                 215                 220
Thr Gln Asp Thr Glu Leu Val Glu Thr Arg Pro Ala Gly Asp Gly Thr
225                 230                 235                 240
Phe Gln Lys Trp Val Ala Val Val Pro Ser Gly Gln Glu Gln Arg
                245                 250                 255
Tyr Thr Cys His Val Gln His Glu Gly Leu Pro Lys Pro Leu Thr Leu
            260                 265                 270
Arg Trp Glu Pro Ser Ser Gln Pro Thr Ile Pro Ile Val Gly Ile Ile
        275                 280                 285
Ala Gly Leu Val Leu Phe Gly Ala Val Ile Thr Gly Ala Val Val Ala
```

```
                290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Val
            340

<210> SEQ ID NO 29
<211> LENGTH: 341
<212> TYPE: PRT
<213> ORGANISM: Artificial Sequence
<220> FEATURE:
<223> OTHER INFORMATION: HLA-A2 alpha chain D227K/T228A

<400> SEQUENCE: 29

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gly Glu Thr
        50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Lys Ala Glu Leu Val Glu Thr Arg Pro Ala Gly Asp Gly Thr
225                 230                 235                 240

Phe Gln Lys Trp Ala Ala Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Thr Gly Ala Val Val Ala
    290                 295                 300

Ala Val Met Trp Arg Arg Lys Ser Ser Asp Arg Lys Gly Gly Ser Tyr
```

```
305                 310                 315                 320
Ser Gln Ala Ala Ser Ser Asp Ser Ala Gln Gly Ser Asp Val Ser Leu
                325                 330                 335

Thr Ala Cys Lys Val
            340

<210> SEQ ID NO 30
<211> LENGTH: 10
<212> TYPE: PRT
<213> ORGANISM: Artificial Sequence
<220> FEATURE:
<223> OTHER INFORMATION: Mart-1 peptide

<400> SEQUENCE: 30

Glu Leu Ala Gly Ile Gly Ile Leu Thr Val
1               5                   10

<210> SEQ ID NO 31
<211> LENGTH: 9
<212> TYPE: PRT
<213> ORGANISM: Human papillomavirus type 16

<400> SEQUENCE: 31

Lys Leu Pro Gln Leu Cys Thr Glu Leu
1               5

<210> SEQ ID NO 32
<211> LENGTH: 9
<212> TYPE: PRT
<213> ORGANISM: Human papillomavirus type 16

<400> SEQUENCE: 32

Gly Thr Leu Gly Ile Val Cys Pro Ile
1               5

<210> SEQ ID NO 33
<211> LENGTH: 9
<212> TYPE: PRT
<213> ORGANISM: Homo sapiens

<400> SEQUENCE: 33

Ser Leu Leu Met Trp Ile Thr Gln Val
1               5

<210> SEQ ID NO 34
<211> LENGTH: 9
<212> TYPE: PRT
<213> ORGANISM: Homo sapiens

<400> SEQUENCE: 34

Ile Leu Leu Trp Gln Pro Ile Pro Val
1               5

<210> SEQ ID NO 35
<211> LENGTH: 250
<212> TYPE: PRT
<213> ORGANISM: Artificial Sequence
<220> FEATURE:
<223> OTHER INFORMATION: Chimeric C259 alpha chain

<400> SEQUENCE: 35

Gln Glu Val Thr Gln Ile Pro Ala Ala Leu Ser Val Pro Glu Gly Glu
1               5                   10                  15

Asn Leu Val Leu Asn Cys Ser Phe Thr Asp Ser Ala Ile Tyr Asn Leu
```

```
            20                  25                  30
Gln Trp Phe Arg Gln Asp Pro Gly Lys Gly Leu Thr Ser Leu Leu Leu
        35                  40                  45
Ile Pro Phe Trp Gln Arg Glu Gln Thr Ser Gly Arg Leu Asn Ala Ser
    50                  55                  60
Leu Asp Lys Ser Ser Gly Arg Ser Thr Leu Tyr Ile Ala Ala Ser Gln
65                  70                  75                  80
Pro Gly Asp Ser Ala Thr Tyr Leu Cys Ala Val Arg Pro Leu Tyr Gly
                85                  90                  95
Gly Ser Tyr Ile Pro Thr Phe Gly Arg Gly Thr Ser Leu Ile Val His
            100                 105                 110
Pro Tyr Ile Gln Asn Pro Glu Pro Ala Val Tyr Gln Leu Lys Asp Pro
        115                 120                 125
Arg Ser Gln Asp Ser Thr Leu Cys Leu Phe Thr Asp Phe Asp Ser Gln
    130                 135                 140
Ile Asn Val Pro Lys Thr Met Glu Ser Gly Thr Phe Ile Thr Asp Lys
145                 150                 155                 160
Thr Val Leu Asp Met Lys Ala Met Asp Ser Lys Ser Asn Gly Ala Ile
                165                 170                 175
Ala Trp Ser Asn Gln Thr Ser Phe Thr Cys Gln Asp Ile Phe Lys Glu
            180                 185                 190
Thr Asn Ala Thr Tyr Pro Ser Ser Asp Val Pro Cys Asp Ala Thr Leu
        195                 200                 205
Thr Glu Lys Ser Phe Glu Thr Asp Met Asn Leu Asn Phe Gln Asn Leu
    210                 215                 220
Ser Val Met Gly Leu Arg Ile Leu Leu Leu Lys Val Ala Gly Phe Asn
225                 230                 235                 240
Leu Leu Met Thr Leu Arg Leu Trp Ser Ser
                245                 250

<210> SEQ ID NO 36
<211> LENGTH: 285
<212> TYPE: PRT
<213> ORGANISM: Artificial Sequence
<220> FEATURE:
<223> OTHER INFORMATION: Chimeric C259 beta chain

<400> SEQUENCE: 36

Ala Gly Val Thr Gln Thr Pro Lys Phe Gln Val Leu Lys Thr Gly Gln
1               5                   10                  15
Ser Met Thr Leu Gln Cys Ala Gln Asp Met Asn His Glu Tyr Met Ser
                20                  25                  30
Trp Tyr Arg Gln Asp Pro Gly Met Gly Leu Arg Leu Ile His Tyr Ser
            35                  40                  45
Val Ser Val Gly Met Thr Asp Gln Gly Glu Val Pro Asn Gly Tyr Asn
        50                  55                  60
Val Ser Arg Ser Thr Thr Glu Asp Phe Pro Leu Arg Leu Leu Ser Ala
65                  70                  75                  80
Ala Pro Ser Gln Thr Ser Val Tyr Phe Cys Ala Ser Ser Tyr Val Gly
                85                  90                  95
Asn Thr Gly Glu Leu Phe Phe Gly Glu Gly Ser Arg Leu Thr Val Leu
            100                 105                 110
Glu Asp Leu Arg Asn Val Thr Pro Pro Lys Val Ser Leu Phe Glu Pro
        115                 120                 125
Ser Lys Ala Glu Ile Ala Asn Lys Gln Lys Ala Thr Leu Val Cys Leu
```

-continued

```
            130                 135                 140
Ala Arg Gly Phe Phe Pro Asp His Val Glu Leu Ser Trp Trp Val Asn
145                 150                 155                 160

Gly Lys Glu Val His Ser Gly Val Ser Thr Asp Pro Gln Ala Tyr Lys
                165                 170                 175

Glu Ser Asn Tyr Ser Tyr Cys Leu Ser Ser Arg Leu Arg Val Ser Ala
                180                 185                 190

Thr Phe Trp His Asn Pro Arg Asn His Phe Arg Cys Gln Val Gln Phe
                195                 200                 205

His Gly Leu Ser Glu Glu Asp Lys Trp Pro Glu Gly Ser Pro Lys Pro
                210                 215                 220

Val Thr Gln Asn Ile Ser Ala Glu Ala Trp Gly Arg Ala Asp Cys Gly
225                 230                 235                 240

Ile Thr Ser Ala Ser Tyr Gln Gln Gly Val Leu Ser Ala Thr Ile Leu
                245                 250                 255

Tyr Glu Ile Leu Leu Gly Lys Ala Thr Leu Tyr Ala Val Leu Val Ser
                260                 265                 270

Thr Leu Val Val Met Ala Met Val Lys Arg Lys Asn Ser
            275                 280                 285
```